(12) United States Patent
Steinhagen et al.

(10) Patent No.: US 8,211,885 B2
(45) Date of Patent: Jul. 3, 2012

(54) CYCLIC INDOLE-3-CARBOXAMIDES, THEIR PREPARATION AND THEIR USE AS PHARMACEUTICALS

(75) Inventors: Henning Steinhagen, Sulzbach (DE); Bodo Scheiper, Frankfurt am Main (DE); Hans Matter, Frankfurt am Main (DE); Hans Ulrich Stilz, Frankfurt am Main (DE); Gary McCort, Paris (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/845,317

(22) Filed: Jul. 28, 2010

(65) Prior Publication Data

US 2011/0039830 A1    Feb. 17, 2011

Related U.S. Application Data

(63) Continuation of application No. PCT/EP2009/000281, filed on Jan. 17, 2009.

(30) Foreign Application Priority Data

Jan. 31, 2008 (EP) .................................. 08290093

(51) Int. Cl.
| | |
|---|---|
| A61K 31/551 | (2006.01) |
| A61K 31/496 | (2006.01) |
| C07D 209/42 | (2006.01) |
| C07D 401/04 | (2006.01) |
| C07D 401/06 | (2006.01) |
| C07D 405/04 | (2006.01) |
| C07D 409/04 | (2006.01) |

(52) U.S. Cl. .............. 514/218; 514/253.09; 514/254.09; 540/575; 544/364; 544/373

(58) Field of Classification Search .......................... None
See application file for complete search history.

(56) References Cited

U.S. PATENT DOCUMENTS

| | | | |
|---|---|---|---|
| 4,148,895 | A | 4/1979 | Lattrell et al. |
| 6,500,853 | B1 | 12/2002 | Seehra et al. |
| 2005/0054631 | A1 | 3/2005 | Jiang et al. |
| 2006/0160786 | A1 | 7/2006 | Brown et al. |

FOREIGN PATENT DOCUMENTS

| | | |
|---|---|---|
| EP | 0716077 | 6/1996 |
| EP | 1156045 | 11/2001 |
| EP | 1243268 | 9/2002 |
| EP | 1452525 | 9/2004 |
| WO | 99/43672 | 9/1999 |
| WO | WO 99/43654 | 9/1999 |
| WO | WO 2005/121175 | 12/2005 |

OTHER PUBLICATIONS

Scheiper et al. Bioorganic & Medicinal Chemistry Letters, vol.20, pp. 6268-6272 (2010).*
Sever et al. Journal of the Renin-Angiotensin-Aldosterone System,vol. 10 (2), pp. 65-76 (2009).*
Azizi, M., et al., Renin Inhibition With Aliskiren: Where are we Now, and Where are we going?, S. Hypertens. vol. 24, (2006), pp. 243-256.
Batey. R. A., et al., Synthesis and Cross-Coupling Reactions of Tetraalkylammonium Organotriflaoroborate Salts, Tetrahedron Letters, vol. 42, pp. 9099-9103, (2001).
Brewster, U. C., et al., The Renin-Angiotensin-Aldosterone System and the Kidney: Effects on Kidney Disease, Am. J. Med., vol. 116, pp. 263-272, (2004).
Chan, et al., New N- and O-Aryiations Wth Phenylboronic Acids and Cupric Acetate, Tetrahedron Letters, vol. 39, (1998), pp. 2933-2936.
Davisson, R. L., et al., Complementation of Reduced Survival, Hypotension, and Renal Abnormalities in Angiotensinogen-Deficient Mice by the Human Renin and Human Angiotensinogen Genes, J. Clin. Invest., vol. 99, (1997), pp. 1258-1264.
Gaedeke, J., et al.,, Pharmacological Management of Renal Fibrotic disease, Expert Opin. Pharmacother., vol. 7, pp. 377-386, (2006).
Humphrey, G. R., et al., Practical Methodologies for the Synthesis of Indoles, Chem. Rev. (2006), pp. 2875-2911, vol. 106.
Kleinert, H.D., et al., Renin Inhibition, Cardiovascular Drugs and Therapy, vol. 9, pp. 645-655, (1995).
Lavoie, J. L., et al., Transgenic Mice for Studies of the Renin-Angiotensin System in Hypertension, Acta Physiol Scand, (2004), vol. 181, pp. 571-577.
Lonn, E., et al., The Clinical Revelance of Pharmacological Blood Pressure Lowering Mechanisms, Can. J. Cardiol., vol. 20, Suppl. B., (2004), pp. 83B-88B.
Mailbaum, J., et al., Renin Inhibitors as Novel Treatments for Cardiovascular Disease, Expert Opinion Ther. Patents, vol. 13, (2003), pp. 589-603.
Marfat, A., et al., Oxidation of Indoles With Pyridinium Bromide Pebromide A Simple and Efficient Synthesis of 7-Azaoxindoles, Tetrahedron Letters, vol. 28, No. 35, pp. 4027-4030, (1987).
Mealy, N. E., et al., Aliskiren Fumarate, Drugs of the Future, vol. 26, No. 12, pp. 1139-1148, (2001).
Merrill, D. C., et al., Chronic Hypertension and Altered Baroreflex Responses in Transgenic Mice Containing the Human Renin and Human Angiotensinogen Genes, J. Clin. Invest., (1996), vol. 97, pp. 1047-1055.

(Continued)

Primary Examiner — Emily Bernhardt
(74) Attorney, Agent, or Firm — Ronald G. Ort

(57) ABSTRACT

The present invention relates to cyclic indole-3-carboxamides of the formula I,

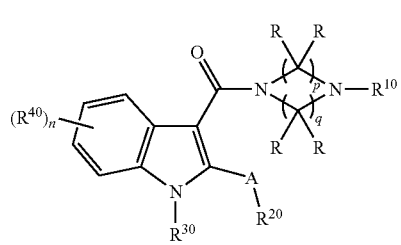

wherein A, R, $R^{10}$, $R^{20}$, $R^{30}$, $R^{40}$, n, p and q have the meanings indicated in the claims, which are valuable pharmaceutical active compounds. Specifically, they inhibit the enzyme renin and modulate the activity of the renin-angiotensin system, and are useful for the treatment of diseases such as hypertension, for example. The invention furthermore relates to processes for the preparation of the compounds of the formula I, their use and pharmaceutical compositions comprising them.

9 Claims, No Drawings

OTHER PUBLICATIONS

Mitsunobu, O., et al., The use of Diethyl Azadicarboxylate and Triphenylphosphine in Synthesis and Transformation of Natural Products, Synthesis., (1981), pp. 1-28.

Moser, M., et al., The use of Renin Inhibitors in the Management of Hypertension. J. Clin. Hypertension, vol. 9, (2007), pp. 701-705.

Old, et al., Efficient Palladium-Catalyzed N-Arylation of indoles, Organic Letters (2000) vol. 2, No. 10, 1403-1406.

Parrick, J., et al., A Convenient Conversion of Indoles to 3,3,-Dibromooxindoles and Then to Isatins, Tetrahedron Letters, vol. 25, No. 29, pp. 3099-3100, (1984).

Pilz, B., et al., Aliskiren, A Human Renin Inhibitor, Ameliorates Cardiac and Renal Damage in Double-Transgenic Rats, Hypertension, vol. 46, pp. 569-576. (2005).

Quach, T.D., et al., Ligand- and Base-Free Copper(II)-Catalyzed C-N Bond Formation: Cross-Coupling Reactions of Organoboron Compounds With Aliphatic Amines and Anilines, Organic Letters, vol. 5, No. 23, pp. 4397-4400, (2003).

Reid, I. A., et al., The Renin-Angiotensin System: Physiology, Pathophysiology, and Pharmacology, J. Physiol Advances in Physiology Education, vol. 20, (1998), pp. S236-S245.

Robinson, R. P., et al., Synthesis of 5-Azaoxindole, J. Org. Chem., (1991) vol. 56, pp. 4805-4806.

Sarges R., et al., A Novel Class of "GABAergic" Agents: 1-Aryl-3-(amincalkylidene)oxindoles, J. Med. Chem. 1989, vol. 32, pp. 437-444.

Scott, B. B., et al., Development of Inhibitors of the Aspartyl Protease Renin for the Treatment of Hypertension, Current Protein and Peptide Science, vol. 7, (2006), pp. 241-254.

Wood, J. M., et al., Aliskiren, a Novel, Orally Effective Renin Inhibitor, Lowers Blood Pressure in Marmosets and Spontaneously Hypertensive Rats, J. Hypertens., vol. 23, (2005), pp. 417-426.

* cited by examiner

CYCLIC INDOLE-3-CARBOXAMIDES, THEIR PREPARATION AND THEIR USE AS PHARMACEUTICALS

FIELD OF THE INVENTION

The present invention relates to cyclic indole-3-carboxamides of the formula I,

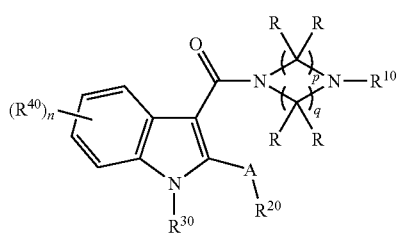

wherein A, R, $R^{10}$, $R^{20}$, $R^{30}$, $R^{40}$, n, p and q have the meanings indicated below, which are valuable pharmaceutical active compounds. Specifically, they inhibit the enzyme renin and modulate the activity of the renin-angiotensin system, and are useful for the treatment of diseases such as hypertension, for example. The invention furthermore relates to processes for the preparation of the compounds of the formula I, their use and pharmaceutical compositions comprising them.

BACKGROUND OF THE INVENTION

The renin-angiotensin system (RAS; also designated as renin-angiotensin aldosterone system, RAAS) is a key regulator of cardiovascular functions as well as for the balance of electrolytes and for maintaining body fluid volume, and a determinant of blood pressure (cf., for example, E. Lonn, Can. J. Cardiol. 20 (Suppl. B) (2004), 83B; I. A. Reid, Am. J. Physiol.: Advances in Physiology Education 20 (1998), S236). It acts via the effects of angiotensin II, an octapeptide hormone, which binds to angiotensin receptors. The formation of angiotensin II involves two main steps. In the first step, renin (EC 3.4.23.15; formerly EC 3.4.99.19 and EC 3.4.4.15), a 340 amino acid aspartyl proteinase, cleaves angiotensinogen to form the biologically inactive decapeptide angiotensin I. In the second step, angiotensin I is converted into angiotensin II by the zinc-dependent protease angiotensin-converting enzyme (ACE).

Renin is produced in the juxtaglomerular cells of the kidney primarily in the form of the biologically inactive prorenin. Its release from the kidney and activation and subsequent RAS activation in normotensive humans is stimulated by sodium or volume depletion, or by a reduction in blood pressure.

RAS activity is the principal determinant of several pathological states since angiotensin II, the major effector molecule of this system, increases blood pressure both directly by arterial vasoconstriction and indirectly by liberating the sodium-retaining hormone aldosterone from the adrenal glands, accompanied by an increase in extracellular fluid volume, as well as having growth-promoting effects on vascular, cardiac and renal tissues which contribute to end-organ damage.

Pharmacological blockade of the RAS is an established way of treating various diseases, for example hypertension (cf., for example, Handbook of Hypertension, W. H. Birkenhäger et al. (ed.), Elsevier Science Publishers, Amsterdam (1986), vol. 8, 489). However, the therapeutic response achieved with the currently used types of RAS blockers, ACE inhibitors and angiotensin receptor blockers, although efficacious, is limited. This may be due to the rise in renin which is induced by these agents and results in an increase in angiotensin I which can be converted into angiotensin II via other pathways than by means of ACE. An inhibition of renin, which controls the initial and rate-limiting step in the RAS by catalyzing the cleavage of the Leu10-Val11 peptide bond of angiotensinogen resulting in the formation of the angiotensin peptides, would inhibit the complete RAS and thus be more efficient. Furthermore, whereas inhibition of ACE also affects the level of other peptides which are cleaved by ACE such as bradykinin, for example, which is associated with side effects of ACE inhibitors like cough or angioedema, renin is specific in that angiotensinogen is its only natural substrate. Inhibition of renin thus offers a specific and powerful way of lowering blood pressure (cf. M. Moser et al., J. Clin. Hypertension, 9 (2007), 701) as well as providing organ protection of organs such as the heart, kidney and brain and, besides for treating hypertension, thus is useful for treating disorders of the cardiovascular system, such as heart failure, cardiac insufficiency, cardiac failure, cardiac infarction, cardiac hypertrophy, vascular hypertrophy, left ventricular dysfunction, in particular left ventricular dysfunction after myocardial infarction, restenosis and angina pectoris; renal diseases, such as renal fibrosis, renal failure and kidney insufficiency; diabetes complications, such as nephropathy and retinopathy; glaucoma; and cerebral afflictions, such as cerebral hemorrhage, for example (with respect to the effect of the RAS on renal diseases and cardiac damage, cf., for example, U. C. Brewster, Am. J. Med. 116 (2004), 263; J. Gaedeke et al., Expert Opin. Pharmacother. 7 (2006), 377; B. Pilz et al., Hypertension 46 (2005), 569).

A large number of peptidic and peptidomimetic inhibitors of human renin with various stable transition-state analogues of the scissile peptide bond have been developed since about 1980 and contributed to the validation of renin as a therapeutic target (cf., for example, B. B. Scott et al., Curr. Protein Pept. Sci. 7 (2006), 241; J. Maibaum et al., Expert Opin. Ther. Patents 13 (2003), 589). However, these compounds generally suffer from deficiencies such as insufficient bioavailability (cf. H. D. Kleinert, Cardiovasc. Drugs Therapy 9 (1985), 645) or duration of action, or high cost of production. Recently, an orally active renin inhibitor, aliskiren (cf. Drugs Fut. 26 (2001), 1139; J. Wood et al., J. Hypertens. 23 (2005), 417; M. Azizi et al., J. Hypertens. 24 (2006), 243) has been marketed. But the property profile of aliskiren is not yet ideal, for example with respect to oral bioavailability, and a particular drawback of aliskiren is its complex molecular structure with four chiral centers and its multistep synthesis. Thus, there is still a great need for new, non-peptidic small molecule renin inhibitors which exhibit favorable properties, for example with respect to oral bioavailability or low molecular complexity and simple synthetic access. The present invention satisfies this need by providing the renin-inhibiting cyclic indole-3-carboxamides of the formula I.

Various indole derivatives have already been described. For example, in US 2005/0054631 and U.S. Pat. No. 4,148, 895 certain indole derivatives are described which comprise an amino group in the 2-position of the indole ring and which are inhibitors of poly(adenosine 5'-diphosphate ribose)polymerase (PARP) useful for the treatment of a variety of diseases including diseases associated with the central nervous system and cardiovascular disorders, or exhibit hypotensive and especially antiarrhythmic activity, respectively. In EP 1452525 indole derivatives are described which, among others, can contain in the 3-position of the indole ring a carboxamide group wherein the amide nitrogen atom is a ring member of a diazacycloalkane which carries on the second ring nitrogen atom a pyridine, pyrazine, pyridazine or pyrimidine group, and which are inhibitors of transforming growth factor β (TGF-β) useful for the treatment of fibroproliferative disorders, for example. Similar indole-3-carboxamide derivatives which are inhibitors of TGF-β and are useful for the treatment of fibroproliferative disorders or specifically for the treatment of nephritis, are described in EP 1156045 and EP 1243268. WO 2005/121175 relates to CD4 mimetic compounds, among them indole derivatives which can contain a carboxamide group the amide nitrogen atom of which is a member of a ring, which complex with envelope proteins of human immunodeficiency virus and are useful for eliciting an immune response. WO 99/43672, WO 99/43654 and U.S. Pat. No. 6,500,853 relate in a very broad manner to derivatives of indole, indoline and other heterocycles, among them indolecarboxamides, which are phospholipase $A_2$ inhibitors and are useful for the treatment of inflammatory conditions. The indole-3-carboxamides of the present invention, wherein the amide nitrogen atom is a ring member of a 1,4- or 1,5-diazacycloalkane ring system, the nitrogen atom in position 1 of the indole ring system carries a cyclic group, and the carbon atom in position 2 of the indole ring system is linked to a (hetero)aromatic group, have not yet been disclosed.

DESCRIPTION OF THE INVENTION

Thus, a subject of the present invention are the compounds of the formula I, in any of their stereoisomeric forms or a mixture of stereoisomeric forms in any ratio, and the physiologically acceptable salts thereof, and the physiologically acceptable solvates of any of them,

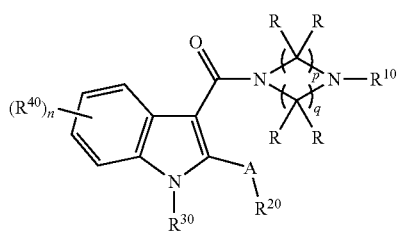

wherein
A is chosen from O, S, N(($C_1$-$C_4$)-alkyl) and C($R^a$)$_2$;
$R^a$ is chosen from hydrogen, fluorine and ($C_1$-$C_4$)-alkyl, wherein the two groups $R^a$ are independent of each other and can be identical or different, or the two groups $R^a$ together are a divalent ($C_2$-$C_8$)-alkyl group;
R is chosen from hydrogen, fluorine, ($C_1$-$C_4$)-alkyl, hydroxy-($C_1$-$C_4$)-alkyl-, ($C_1$-$C_4$)-alkyl-O—($C_1$-$C_4$)-alkyl-, phenyl-($C_1$-$C_4$)-alkyl-, heteroaryl-($C_1$-$C_4$)-alkyl-, ($C_1$-$C_4$)-alkyl-O—CO—$C_uH_{2u}$—, $R^1$—NH—CO—$C_uH_{2u}$— and ($C_1$-$C_4$)-alkyl-O—, wherein all groups R are independent of each other and can be identical or different;
$R^1$ is chosen from hydrogen, ($C_1$-$C_4$)-alkyl, hydroxy-($C_1$-$C_4$)-alkyl- and $H_2N$—CO—($C_1$-$C_4$)-alkyl-;
$R^{10}$ is chosen from hydrogen, ($C_1$-$C_6$)-alkyl-O—CO— and ($C_3$-$C_7$)-cycloalkyl-$C_vH_{2v}$—O—CO—;
$R^{20}$ is chosen from phenyl and heteroaryl which are optionally substituted by one or more identical or different substituents chosen from halogen, ($C_1$-$C_4$)-alkyl, ($C_1$-$C_4$)-alkyl-O—, ($C_1$-$C_4$)-alkyl-S(O)$_m$—, hydroxy and cyano;

$R^{30}$ is chosen from ($C_3$-$C_7$)-cycloalkyl, ($C_5$-$C_7$)-cycloalkenyl, tetrahydropyranyl, phenyl and heteroaryl, wherein cycloalkyl and cycloalkenyl are optionally substituted by one or more identical or different substituents chosen from fluorine, ($C_1$-$C_4$)-alkyl and hydroxy, and phenyl and heteroaryl are optionally substituted by one or more identical or different substituents chosen from halogen, ($C_1$-$C_6$)-alkyl, ($C_3$-$C_7$)-cycloalkyl-$C_vH_{2v}$—, hydroxy-($C_1$-$C_6$)-alkyl-, ($C_1$-$C_4$)-alkyl-O—($C_1$-$C_6$)-alkyl-, ($C_3$-$C_7$)-cycloalkyl-$C_vH_{2v}$—O—($C_1$-$C_6$)-alkyl-, ($C_1$-$C_4$)-alkyl-CO—NH—($C_1$-$C_6$)-alkyl-, hydroxy, ($C_1$-$C_6$)-alkyl-O—, ($C_3$-$C_7$)-cycloalkyl-$C_vH_{2v}$—O—, hydroxy-($C_1$-$C_6$)-alkyl-O—, ($C_1$-$C_4$)-alkyl-O—($C_1$-$C_6$)-alkyl-O—, ($C_3$-$C_7$)-cycloalkyl-$C_vH_{2v}$—O—($C_1$-$C_6$)-alkyl-O—, ($C_1$-$C_4$)-alkyl-CO—NH—($C_1$-$C_6$)-alkyl-O—, ($C_1$-$C_6$)-alkyl-S(O)$_m$— and cyano;
$R^{40}$ is chosen from halogen, ($C_1$-$C_4$)-alkyl, ($C_3$-$C_7$)-cycloalkyl-$C_vH_{2v}$—, phenyl-($C_1$-$C_4$)-alkyl-, heteroaryl-($C_1$-$C_4$)-alkyl-, hydroxy-($C_1$-$C_4$)-alkyl-, ($C_1$-$C_4$)-alkyl-O—($C_1$-$C_4$)-alkyl-, ($C_3$-$C_7$)-cycloalkyl-$C_vH_{2v}$—O—($C_1$-$C_4$)-alkyl-, phenyl-O—($C_1$-$C_4$)-alkyl-, heteroaryl-O—($C_1$-$C_4$)-alkyl-, di(($C_1$-$C_4$)-alkyl)N—($C_1$-$C_4$)-alkyl-, HO—CO—($C_1$-$C_4$)-alkyl-, ($C_1$-$C_4$)-alkyl-O—CO—($C_1$-$C_4$)-alkyl-, $H_2N$—CO—($C_1$-$C_4$)-alkyl-, hydroxy, ($C_1$-$C_4$)-alkyl-O—, ($C_3$-$C_7$)-cycloalkyl-$C_vH_{2v}$—O—, phenyl-($C_1$-$C_4$)-alkyl-O—, heteroaryl-($C_1$-$C_4$)-alkyl-O—, hydroxy-($C_1$-$C_4$)-alkyl-O—, ($C_1$-$C_4$)-alkyl-O—($C_1$-$C_4$)-alkyl-O—, ($C_3$-$C_7$)-cycloalkyl-$C_vH_{2v}$—O—($C_1$-$C_4$)-alkyl-O—, phenyl-O—($C_1$-$C_4$)-alkyl-O—, heteroaryl-O—($C_1$-$C_4$)-alkyl-O—, di(($C_1$-$C_4$)-alkyl)N—($C_1$-$C_4$)-alkyl-O—, HO—CO—($C_1$-$C_4$)-alkyl-O—, ($C_1$-$C_4$)-alkyl-O—CO—($C_1$-$C_4$)-alkyl-O—, $H_2N$—CO—($C_1$-$C_4$)-alkyl-O—, ($C_1$-$C_4$)-alkyl-CO—O—, ($C_3$-$C_7$)-cycloalkyl-$C_vH_{2v}$—CO—O—, ($C_1$-$C_4$)-alkyl-NH—CO—O—, ($C_3$-$C_7$)-cycloalkyl-$C_vH_{2v}$—NH—CO—O—, ($C_1$-$C_4$)-alkyl-S(O)$_m$—, nitro, amino, ($C_1$-$C_4$)-alkylamino, di(($C_1$-$C_4$)-alkyl)amino, ($C_1$-$C_4$)-alkyl-CO—NH—, ($C_3$-$C_7$)-cycloalkyl-$C_vH_{2v}$—CO—NH—, ($C_1$-$C_4$)-alkyl-S(O)$_2$—NH—, HO—CO—, ($C_1$-$C_4$)-alkyl-O—CO—, $H_2N$—CO—, (($C_1$-$C_4$)-alkyl)-NH—CO—, di(($C_1$-$C_4$)-alkyl)N—CO—, cyano, HO—S(O)$_2$—, $H_2N$—S(O)$_2$—, (($C_1$-$C_4$)-alkyl)-NH—S(O)$_2$— and di(($C_1$-$C_4$)-alkyl)N—S(O)$_2$—, wherein all substituents $R^{40}$ are independent of each other and can be identical or different;
heteroaryl is an aromatic monocyclic, 5-membered or 6-membered, heterocyclic group which comprises 1, 2 or 3 identical or different ring heteroatoms chosen from N, O and S, wherein one of the ring nitrogen atoms can carry a hydrogen atom or a ($C_1$-$C_4$)-alkyl group, and wherein the heteroaryl group is bonded via a ring carbon atom;
m is chosen from 0, 1 and 2, wherein all numbers m are independent of each other and can be identical or different;
n is chosen from 0, 1, 2, 3 and 4;
p and q, which are independent of each other and can be identical or different, are chosen from 2 and 3;
u is chosen from 0, 1 and 2, wherein all numbers u are independent of each other and can be identical or different;
v is chosen from 0, 1 and 2, wherein all numbers v are independent of each other and can be identical or different;
wherein all alkyl groups, independently of each other, are optionally substituted by one or more fluorine atoms;
wherein all cycloalkyl groups, independently of each other, are optionally substituted by one or more identical or different substituents chosen from fluorine and ($C_1$-$C_4$)-alkyl, unless specified otherwise;
wherein all phenyl and heteroaryl groups present in R and $R^{40}$, independently of each other, are optionally substituted by one or more identical or different substituents chosen from halogen, $(C_1-C_4)$-alkyl, $(C_1-C_4)$-alkyl-O—, $(C_1-C_4)$-alkyl-S(O)$_2$— and cyano.

If structural elements such as groups, substituents or numbers can occur several times in the compounds of the formula I, they are all independent of one another and can in each case have any of the indicated meanings, and can in each case be identical to or different from any other such element.

Alkyl groups, i.e. saturated hydrocarbon residues, can be straight-chain (linear) or branched. This also applies if these groups are substituted or are part of another group, for example an alkyl-O— group (alkyloxy group, alkoxy group) or an alkyl-S(O)$_m$— group. Depending on the respective definition, the number of carbon atoms in an alkyl group can be 1, 2, 3, 4, 5, 6, 7 or 8. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, hexyl including n-hexyl, 3,3-dimethylbutyl and isohexyl, heptyl including n-heptyl, and octyl including n-octyl. Examples of alkyl-O— are methoxy, ethoxy, n-propoxy, isopropoxy, n-butoxy, isobutoxy, tert-butoxy and n-pentoxy. Examples of alkyl-S(O)$_m$— are methanesulfanyl-(CH$_3$—S—, methylsulfanyl), methanesulfinyl-(CH$_3$—S(O)—), methanesulfonyl-(CH$_3$—S(O)$_2$—), ethanesulfanyl-(CH$_3$—CH$_2$—S—, ethylsulfanyl-), ethanesulfinyl-(CH$_3$—CH$_2$—S(O)—), ethanesulfonyl-(CH$_3$—CH$_2$—S(O)$_2$—), 1-methylethanesulfanyl-((CH$_3$)$_2$CH—S—, 1-methylethylsulfanyl-), 1-methylethanesulfinyl-((CH$_3$)$_2$CH—S(O)—) and 1-methylethanesulfonyl-((CH$_3$)$_2$CH—S(O)$_2$—). In one embodiment of the invention the number m is chosen from 0 and 2, wherein all numbers m are independent of each other and can be identical or different.

A substituted alkyl group can be substituted in any positions, provided that the resulting compound is sufficiently stable and is suitable as a pharmaceutical active compound. The prerequisite that a specific group and a compound of the formula I are sufficiently stable and suitable as a pharmaceutical active compound, applies in general with respect to all groups in the compounds of the formula I. If an alkyl group can be monosubstituted or polysubstituted by fluorine, it can be unsubstituted, i.e. not carry fluorine atoms, or substituted, for example by 1, 2, 3, 4, 5, 6, 7, 8, 9, 10 or 11 fluorine atoms, preferably by 1, 2, 3, 4 or 5 fluorine atoms, which can be present in any positions. For example, in a fluoro-substituted alkyl group one or more methyl groups can carry three fluorine atoms each and be present as trifluoromethyl groups, and/or one or more methylene groups (CH$_2$) can carry two fluorine atoms each and be present as difluoromethylene groups. The explanations with respect to the substitution of a group by fluorine also apply if the group additionally carries other substituents and/or is part of another group, for example of an alkyl-O— group. Examples of fluoro-substituted alkyl groups are trifluoromethyl, 2-fluoroethyl, 1,1-difluoroethyl, 2,2,2-trifluoroethyl, pentafluoroethyl, 3,3,3-trifluoropropyl, 2,2,3,3,3-pentafluoropropyl, 4,4,4-trifluorobutyl and heptafluoroisopropyl. Examples of fluoro-substituted alkyl-O— groups are trifluoromethoxy, 2,2,2-trifluoroethoxy, pentafluoroethoxy and 3,3,3-trifluoropropoxy. Examples of fluoro-substituted alkyl-S(O)$_m$— groups are trifluoromethanesulfanyl-(CF$_3$—S—, trifluoromethylsulfanyl-), trifluoromethanesulfinyl-(CF$_3$—S(O)—) and trifluoromethanesulfonyl-(CF$_3$—S(O)$_2$—).

If applicable, the above explanations with respect to alkyl groups apply correspondingly to divalent alkyl groups (alkanediyl groups) including the divalent alkyl groups $C_uH_{2u}$ and $C_vH_{2v}$, which groups can also be regarded as the alkyl part of a substituted alkyl group. Thus, divalent alkyl groups including the divalent alkyl groups $C_uH_{2u}$ and $C_vH_{2v}$ can also be straight-chain or branched, the bonds to the adjacent groups can be present in any positions and can start from the same carbon atom or from different carbon atoms, and they can be substituted by fluorine. Examples of divalent alkyl groups are —CH$_2$—, —CH$_2$—CH$_2$—, —CH$_2$—CH$_2$—CH$_2$—, —CH$_2$—CH$_2$—CH$_2$—CH$_2$—, —CH$_2$—CH$_2$—CH$_2$—CH$_2$—CH$_2$—, —CH$_2$—CH$_2$—CH$_2$—CH$_2$—CH$_2$—CH$_2$—, —CH(CH$_3$)—, —C(CH$_3$)$_2$—, —CH(CH$_3$)—CH$_2$—, —CH$_2$—CH(CH$_3$)—, —C(CH$_3$)$_2$—CH$_2$— and —CH$_2$—C(CH$_3$)$_2$—. Examples of fluoro-substituted divalent alkyl groups which can contain 1 2, 3, 4, 5 or 6 fluorine atoms, for example, are —CHF—, —CF$_2$—, —CF$_2$—CH$_2$—, —CH$_2$—CF$_2$—, —CF$_2$—CF$_2$—, —CF(CH$_3$)—, —C(CF$_3$)$_2$—, —C(CH$_3$)$_2$—CF$_2$— and —CF$_2$—C(CH$_3$)$_2$—. If the number u in a divalent alkyl group $C_uH_{2u}$ or the number v in a divalent alkyl group $C_vH_{2v}$ is 0 (zero), the two adjacent groups which are bonded to this group are directly bonded to one another through a single bond. For example, if the group $R^{40}$ is the group $(C_3-C_7)$-cycloalkyl-$C_vH_{2v}$—, which group is bonded to the remainder of the molecule via the $C_vH_{2v}$ moiety as is symbolized by the terminal line (hyphen) next to the $C_vH_{2v}$ moiety representing the free bond, and the number v therein is 0, the $(C_3-C_7)$-cycloalkyl group is bonded directly through a single bond to the carbon atom which carries the group $R^{40}$. In one embodiment of the invention the number v is chosen from 0 and 1, wherein all numbers v are independent of each other and can be identical or different.

The number of ring carbon atoms in a cycloalkyl group can be 3, 4, 5, 6 or 7. The number of ring carbon atoms in a cycloalkenyl group can be 5, 6 or 7. Examples of cycloalkyl are cyclopropyl, cyclobutyl, cyclopentyl, cyclohexyl and cycloheptyl, examples of cycloalkenyl are cyclopentenyl, cyclohexenyl and cycloheptenyl. The double bond in a cycloalkenyl group can be present in any position with respect to the carbon atom in position 1 via which the group is bonded to the indole ring, and cycloalkenyl can thus be cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, for example. In preferred embodiments of the present invention, a cycloalkyl group, such as $(C_3-C_7)$-cycloalkyl, in the definition of any group is chosen from a subgroup of any two or more of the said specific cycloalkyl groups, for example from cyclopropyl and cyclobutyl, or from cyclopropyl, cyclobutyl and cyclopentyl, or from cyclopropyl, cyclopentyl and cyclohexyl, or from cyclopentyl and cyclohexyl, or from cyclopentyl, cyclohexyl and cycloheptyl. Similarly, in preferred embodiments a cycloalkenyl group is chosen from a subgroup of any two or more of the said specific cycloalkenyl groups, for example from cyclopentenyl and cyclohexenyl, or from cyclohexenyl and cycloheptenyl, or from cyclopent-1-enyl, cyclopent-2-enyl, cyclohex-1-enyl, cyclohex-2-enyl, cyclohept-1-enyl and cyclohept-2-enyl, or from cyclopent-2-enyl, cyclopent-3-enyl, cyclohex-2-enyl, cyclohex-3-enyl, cyclohept-2-enyl, cyclohept-3-enyl and cyclohept-4-enyl, or from cyclopent-2-enyl and cyclohex-2-enyl, or from cyclopent-2-enyl, cyclohex-2-enyl and cyclohept-2-enyl. In one embodiment of the invention, the carbon atom via which the cycloalkenyl group representing $R^{30}$ is bonded to the indole ring, is not part of the double bond, i.e., the cycloalkenyl group is not a cycloalk-1-enyl group. Cycloalkyl groups and cycloalkenyl groups generally are optionally substituted by one or more $(C_1-C_4)$-alkyl substituents. I.e., they are unsubstituted, i.e. do not carry alkyl substituents, or substituted, for example by 1, 2, 3 or 4 identical or different $(C_1-C_4)$-alkyl substituents, for example by methyl groups and/or ethyl groups and/or isopropyl groups and/or tert-butyl groups, in particular by methyl groups, which substituents can be present in any positions. Examples of alkyl-substituted cycloalkyl groups are 1-methyl-cyclopropyl, 2,2-dimethyl-cyclopropyl, 1-methyl-cyclopentyl, 2,3-dimethyl-cyclopentyl, 1-methyl-cyclohexyl, 4-methyl-cyclohexyl, 4-isopropyl-cyclohexyl, 4-tert-butyl-cyclohexyl and 3,3,5,5-tetramethyl-cyclohexyl. Examples of alkyl-substituted cycloalkenyl groups are 1-methyl-cyclopent-2-enyl, 2-methyl-cyclopent-2-enyl, 3-methyl-cyclopent-2-enyl, 3,4-dimethyl-cyclopent-3-enyl, 1-methyl-cyclohex-2-enyl, 2-methyl-cyclohex-2-enyl, 3-methyl-cyclohex-2-enyl, 4-methyl-cyclohex-2-enyl, 2-methyl-cyclohex-3-enyl, 3-methyl-cyclohex-3-enyl, 4-methyl-cyclohex-3-enyl, 2,3-dimethyl-cyclohex-2-enyl, 4,4-dimethyl-cyclohex-2-enyl, 3,4-dimethyl-cyclohex-3-enyl. Cycloalkyl groups and cycloalkenyl groups generally also are optionally substituted by one or more fluorine atoms. I.e., they are unsubstituted, i.e. do not carry fluorine atoms, or substituted, for example by 1, 2, 3, 4, 5, 6, 7, 8, 9, 10 or 11 fluorine atoms, preferably by 1, 2, 3, 4, 5 or 6 fluorine atoms. Cycloalkyl groups and cycloalkenyl groups can also be substituted simultaneously by fluorine and alkyl. The fluorine atoms can be present in any positions and can also be present in an alkyl substituent. Examples of fluoro-substituted cycloalkyl groups are 1-fluoro-cyclopropyl, 2,2-difluoro-cyclopropyl, 3,3-difluoro-cyclobutyl, 1-fluoro-cyclohexyl, 4,4-difluoro-cyclohexyl and 3,3,4,4,5,5-hexafluoro-cyclohexyl. Examples of fluoro-substituted cycloalkenyl groups are 1-fluoro-cyclopent-2-enyl, 1-fluoro-cyclohex-2-enyl, 4-fluoro-cyclohex-2-enyl, 4,4-difluoro-cyclohex-2-enyl. In one embodiment of the invention, cycloalkyl groups are not optionally substituted by substituents chosen from fluorine and $(C_1-C_4)$-alkyl. If a cycloalkyl group or cycloalkenyl group can be substituted by further substituents like hydroxy, as in the case of a cycloalkyl group or cycloalkenyl group representing $R^{30}$, it can be substituted by one or more such further substituents like hydroxy only and not by substituents chosen from fluorine and $(C_1-C_4)$-alkyl, or by one or more such further substituents and simultaneously by one or more substituents chosen from fluorine and $(C_1-C_4)$-alkyl. The number of such further substituents like hydroxy which can be present on a cycloalkyl or cycloalkenyl group, preferably is 1, 2 or 3, more preferably 1 or 2, for example 1. The total number of all substituents in a cycloalkyl group or cycloalkenyl group preferably is 1, 2, 3, 4, 5, 6, 7 or 8, more preferably 1, 2, 3, 4 or 5, for example 1, 2 or 3. Such further substituents like hydroxy can be present in any positions, provided that the resulting compound is sufficiently stable and is suitable as a subgroup in a pharmaceutical active compound. Preferably, a hydroxy substituent is not present in position 1 of a cycloalkenyl group or cycloalkyl group representing $R^{30}$, and in a cycloalkenyl group a hydroxy substituent is not present on a carbon atom which is part of the double bond. Examples of hydroxy-substituted cycloalkyl groups are 3-hydroxy-cyclobutyl, 2-hydroxy-cyclopentyl, 3-hydroxy-cyclopentyl, 3,4-dihydroxy-cyclopentyl, 2-hydroxy-cyclohexyl, 3-hydroxy-cyclohexyl, 4-hydroxy-cyclohexyl, 2,3-dihydroxy-cyclohexyl, 2,4-dihydroxy-cyclohexyl, 3,4-dihydroxy-cyclohexyl, 3,5-dihydroxy-cyclohexyl, 3,4,5-trihydroxy-cyclohexyl, 2-hydroxy-cycloheptyl, 3-hydroxy-cycloheptyl, 4-hydroxy-cycloheptyl. Examples of hydroxy-substituted cycloalkenyl groups are 5-hydroxy-cyclopent-2-enyl, 4-hydroxy-cyclohex-2-enyl, 5-hydroxy-cyclohex-2-enyl, 6-hydroxy-cyclohex-2-enyl, 6-hydroxy-cyclohex-3-enyl. Examples of the group cycloalkylalkyl-, which can be present in the group $(C_3-C_7)$-cycloalkyl-$C_vH_{2v}$—, are cyclopropylmethyl-, cyclobutylmethyl-, cyclopentylmethyl-, cyclohexylmethyl-, cycloheptylmethyl-, cyclopropyldifluoromethyl-, cyclobutyldifluoromethyl-, cyclopentyldifluoromethyl-, cyclohexyldifluoromethyl-, cycloheptyldifluoromethyl-, 1-cyclopropylethyl-, 2-cyclopropylethyl-, 1-cyclobutylethyl-, 2-cyclobutylethyl-, 1-cyclopentylethyl-, 2-cyclopentylethyl-, 1-cyclohexylethyl-, 2-cyclohexylethyl-, 1-cycloheptylethyl-, 2-cycloheptylethyl-.

A tetrahydropyranyl group representing $R^{30}$, which group can also be designated as oxanyl group or tetrahydro-2H-pyranyl group, can be bonded via any carbon atom and can be tetrahydropyran-2-yl, tetrahydropyran-3-yl or tetrahydropyran-4-yl. Preferably, tetrahydropyranyl is tetrahydropyran-3-yl or tetrahydropyran-4-yl. In one embodiment of the invention, tetrahydropyranyl is tetrahydropyran-4-yl.

In substituted phenyl groups, the substituents can be present in any positions. In monosubstituted phenyl groups, the substituent can be present in the 2-position, the 3-position or the 4-position. In disubstituted phenyl groups, the substituents can be present in 2,3-position, 2,4-position, 2,5-position, 2,6-position, 3,4-position or 3,5-position. In trisubstituted phenyl groups, the substituents can be present in 2,3,4-position, 2,3,5-position, 2,3,6-position, 2,4,5-position, 2,4,6-position or 3,4,5-position. If a phenyl group carries four substituents, of which one, two, three or four substituents can be fluorine atoms, for example, the unsubstituted ring carbon atom can be present in the 2-position, the 3-position or the 4-position. If a polysubstituted phenyl group or heteroaryl group carries different substituents, each substituent can be present in any suitable position, and the present invention comprises all positional isomers. The number of substituents in a substituted phenyl group can be 1, 2, 3, 4 or 5. Preferably, a substituted phenyl group, and likewise a substituted heteroaryl group, carries 1, 2 or 3, in particular 1 or 2, identical or different substituents. In preferred embodiments of the invention, the substituents in substituted phenyl and heteroaryl groups are chosen from any subgroup of the substituents listed in the respective definition, for example by substituents chosen from halogen, $(C_1-C_4)$-alkyl, $(C_1-C_4)$-alkyl-O— and $(C_1-C_4)$-alkyl-S(O)$_m$—, or from halogen, $(C_1-C_4)$-alkyl, $(C_1-C_4)$-alkyl-O— and cyano, or from halogen, $(C_1-C_4)$-alkyl and $(C_1-C_4)$-alkyl-O—, in the case of a phenyl group or heteroaryl group representing $R^{20}$, wherein all alkyl groups can be unsubstituted or substituted by one or more fluorine atoms and, as an example of substituents containing fluorine-substituted alkyl, the substituents comprising the group $CF_3$ (trifluoromethyl) such as $CF_3$ itself, $CF_3$—O— or $CF_3$—S— may be included in each list of substituents in addition to substituents comprising unsubstituted alkyl.

In a heteroaryl group, which is a residue of an aromatic monocyclic, 5-membered or 6-membered heterocyclic ring system, the ring heteroatoms indicated in the definition of the group can be present in any combination and can be present in any suitable position, provided that the group is in line with its definition and the resulting compound of the formula I is stable and suitable as a pharmaceutical active compound. The one of the ring nitrogen atoms specifically referred to in the definition of the group heteroaryl which can carry a hydrogen atom or a substituent such as alkyl, is the ring nitrogen atom in a 5-membered ring system such as pyrrole, pyrazole, imidazole or triazole to which an exocyclic atom or group is bonded. Examples of ring systems from which a heteroaryl group can be derived are pyrrole, furan, thiophene, imidazole, pyrazole, triazoles such as [1,2,3]triazole and [1,2,4]triazole, oxazole ([1,3]oxazole), isoxazole ([1,2]oxazole), thiazole ([1,3]thiazole), isothiazole ([1,2]thiazole), oxadiazoles such as [1,2,4]oxadiazole, [1,3,4]oxadiazole and [1,2,5]oxadiazole, thiadiazoles such as [1,3,4]thiadiazole, pyridine, pyridazine, pyrimidine, pyrazine, triazines such as [1,2,3]triazine, [1,2,4]triazine and [1,3,5]triazine. In one embodiment of the invention, a heteroaryl group comprises one or two identical or different ring heteroatoms, in another embodiment of the invention heteroaryl comprises one ring heteroatom, which are defined as indicated. In another embodiment heteroaryl is chosen from thiophenyl, thiazolyl and pyridinyl. In another embodiment heteroaryl is chosen from thiophenyl and pyridinyl. In another embodiment heteroaryl is thiophenyl. Heteroaryl groups can be bonded via any ring carbon atom. For example, a thiophenyl group (thienyl group) can be thiophen-2-yl (2-thienyl) or thiophen-3-yl (3-thienyl), furanyl can be furan-2-yl or furan-3-yl, pyridinyl (pyridyl) can be pyridin-2-yl, pyridin-3-yl or pyridin-4-yl, pyrazolyl can be 1H-pyrazol-3-yl, 1H-pyrazol-4-yl or 2H-pyrazol-3-yl, imidazolyl can be 1H-imidazol-2-yl, 1H-imidazol-4-yl or 3H-imidazolyl-4-yl, thiazolyl can be thiazol-2-yl, thiazol-4-yl or thiazol-5-yl, [1,2,4]triazolyl can be 1H-[1,2,4]triazol-3-yl, 2H-[1,2,4]triazol-3-yl or 4H-[1,2,4]triazol-3-yl.

In substituted heteroaryl groups, the substituents can be present in any positions, for example in a thiophen-2-yl group or a furan-2-yl group in the 3-position and/or in the 4-position and/or in the 5-position, in a thiophen-3-yl group or a furan-3-yl group in the 2-position and/or in the 4-position and/or in the 5-position, in a pyridin-2-yl group in the 3-position and/or in the 4-position and/or in the 5-position and/or in the 6-position, in a pyridin-3-yl group in the 2-position and/or in the 4-position and/or in the 5-position and/or in the 6-position, in a pyridin-4-yl group in the 2-position and/or in the 3-position and/or in the 5-position and/or in the 6-position. Preferably, a substituted heteroaryl group is substituted by one, two or three, in particular one or two, for example one, identical or different substituents. If a ring nitrogen atom is present which can carry a hydrogen atom or a substituent, the substituent on this nitrogen atom can be a methyl group, an ethyl group, a propyl group or a tert-butyl group, for example, which groups can also be monosubstituted or polysubstituted by fluorine. Generally, suitable ring nitrogen atoms in an aromatic ring of a heteroaryl group, for example the nitrogen atom in a pyridinyl group or a nitrogen atom in a [1,2,5]oxadiazolyl group, can also carry an oxido substituent —O⁻ and compounds of the formula I thus be present in the form of an N-oxide.

Halogen is fluorine, chlorine, bromine or iodine, preferably fluorine, chlorine or bromine, in particular fluorine or chlorine.

The present invention comprises all stereoisomeric forms of the compounds of the formula I, for example, all possible enantiomers and diastereomers including cis/trans isomers. The invention likewise comprises mixtures of two or more stereoisomeric forms, for example mixtures of enantiomers and/or diastereomers including cis/trans isomers, in all ratios. Asymmetric centers contained in the compounds of the formula I, for example in unsubstituted or substituted alkyl groups or in the diazacycloalkane ring depicted in formula I, can all independently of one another have the S configuration or the R configuration. The invention relates to enantiomers, both the levorotatory and the dextrorotatory antipode, in enantiomerically pure form and substantially enantiomerically pure form and in the form of racemates and in the form of mixtures of the two enantiomers in all ratios. The invention likewise relates to diastereomers in the form of pure and substantially pure diastereomers and in the form of mixtures of two or more diastereomers in all ratios. The invention also comprises all cis/trans isomers of the compounds of the formula I in pure form and substantially pure form and in the form of mixtures of the cis isomer and the trans isomer in all ratios. Cis/trans isomerism can occur in substituted cycloalkane rings and in the diazacycloalkane ring depicted in formula I, for example. The preparation of individual stereoisomers, if desired, can be carried out by resolution of a mixture according to customary methods, for example by chromatography or crystallization, or by use of stereochemically uniform starting compounds in the synthesis or by stereoselective reactions. Optionally, before a separation of stereoisomers a derivatization can be carried out. The separation of a mixture of stereoisomers can be carried out at the stage of the compound of the formula I or at the stage of an intermediate in the course of the synthesis. The invention also comprises all tautomeric forms of the compounds of the formula I.

Physiologically acceptable salts of the compounds of the formula I are in particular salts with a nontoxic salt component and preferably are pharmaceutically utilizable salts. They can contain inorganic or organic salt components. Such salts can be formed, for example, from compounds of the formula I which contain an acidic group, for example a carboxylic acid group (HO—CO—) or a sulfonic acid group (HO—S(O)$_2$—) and nontoxic inorganic or organic bases. Suitable bases are, for example, alkali metal compounds or alkaline earth metal compounds, such as sodium hydroxide, potassium hydroxide, sodium carbonate or sodium hydrogencarbonate, or ammonia, organic amino compounds and quaternary ammonium hydroxides. Reactions of compounds of the formula I with bases for the preparation of the salts are in general carried out according to customary procedures in a solvent or diluent. On account of the physiological and chemical stability, advantageous salts of acidic groups are in many cases sodium, potassium, magnesium or calcium salts or ammonium salts which can also carry one or more organic groups on the nitrogen atom. Compounds of the formula I which contain a basic, i.e. protonatable, group, for example an amino group, the diazacycloalkane moiety depicted in formula I in case $R^{10}$ is hydrogen, or another basic heterocycle, can be present in the form of their acid addition salts with physiologically acceptable acids, for example as salt with hydrogen chloride, hydrogen bromide, phosphoric acid, sulfuric acid, acetic acid, benzoic acid, methanesulfonic acid, p-toluenesulfonic acid, which in general can be prepared from the compounds of the formula I by reaction with an acid in a solvent or diluent according to customary procedures. As usual, in particular in the case of acid addition salts of a compound containing two or more basic groups, in an obtained salt the ratio of the salt components can deviate upward or downward from the stoichiometric ratio, such as the molar ratio 1:1 or 1:2 in the case of the acid addition salt of a compound of the formula I containing one or two basic groups with a monovalent acid, and vary depending on the applied conditions. The present invention comprises also salts containing the components in a non-stoichiometric ratio, and an indication that an acid addition salt of a compound of the formula I contains an acid in equimolar amount, for example, also allows for a lower or higher amount of acid in the obtained salt, for example about 0.8 or about 1.1 mol of acid per mol of compound of the formula I. If the compounds of the formula I simultaneously contain an acidic and a basic group in the molecule, the invention also includes internal salts (betaines, zwitterions) in addition to the salt forms mentioned. The present invention also comprises all salts of the compounds of the formula I which, because of low physiological tolerability, are not directly suitable for use as a pharmaceutical, but are suitable as intermediates for chemical reactions or for the preparation of physiologically acceptable salts, for example by means of anion exchange or cation exchange. A subject of the present invention also are solvates of the compounds of the formula I and their salts, such as hydrates and adducts with alcohols like ($C_1$-$C_4$)-alkanols, in particular physiologically acceptable solvates, as well as active metabolites of compounds of the formula I and prodrugs of the compounds of the formula I, i.e. compounds which in vitro may not necessarily exhibit pharmacological activity but which in vivo are converted into pharmacologically active compounds of the formula I, for example compounds which are converted by metabolic hydrolysis into compounds of the formula I. Examples of such prodrugs are compounds in which an acylatable nitrogen atom, for example the nitrogen atom carrying the group $R^{10}$ in the diazacycloalkane moiety depicted in formula I in case $R^{10}$ is hydrogen, carries an alkyl-O—CO— group or an acyl group such as an alkyl-CO— group, for example, and thus has been converted into a carbamate group or an amide group, or compounds in which a carboxylic acid group has been esterified.

The group A is preferably chosen from O, S, $NCH_3$ and $C(R^a)_2$, more preferably from O, S and $C(R^a)_2$, particularly preferably from O and $C(R^a)_2$. In one embodiment of the invention the group A is chosen from O and S. In another embodiment of the invention the group A is O, in another embodiment the group A is $C(R^a)_2$.

If the two groups $R^a$ together are a divalent ($C_2$-$C_8$)-alkyl group, the said alkyl group is preferably bonded to the carbon atom carrying the groups $R^a$ via two distinct carbon atoms and forms, together with the carbon atom carrying the groups $R^a$, a cycloalkane ring to which the indole ring depicted in formula I and the group $R^{20}$ are bonded in the same ring position. The said cycloalkane ring, like a cycloalkane ring in the compounds of the formula I in general, can carry one or more ($C_1$-$C_4$)-alkyl groups, for example one, two, three or four methyl groups, and/or one or more, for example one, two, three or four fluorine atoms. Preferably the said cycloalkane ring is a cyclopropane, cyclobutane, cyclopentane or cyclohexane ring which can all be unsubstituted or substituted by alkyl and/or fluorine as indicated. In one embodiment of the invention the said cycloalkane ring is a cyclopropane ring which can be unsubstituted or substituted by alkyl and/or fluorine as indicated, i.e., in this embodiment the divalent ($C_2$-$C_8$)-alkyl group is an ethane-1,2-diyl group (1,2-ethylene group) which is unsubstituted or substituted by alkyl and/or fluorine as indicated. Preferably the divalent ($C_2$-$C_8$)-alkyl group is a ($C_2$-$C_5$)-alkyl group, more preferably a ($C_2$-$C_4$)-alkyl group, for example a $C_2$-alkyl group. In one embodiment of the invention, the groups $R^a$ are chosen from hydrogen and fluorine, in another embodiment from hydrogen and ($C_1$-$C_4$)-alkyl, wherein the two groups $R^a$ are independent of each other and can be identical or different, or in all these embodiments the two groups $R^a$ together are a divalent ($C_2$-$C_8$)-alkyl group. In one embodiment of the invention the groups $R^a$ are identical or different groups chosen from hydrogen and fluorine, in another embodiment they are identical and different groups chosen from hydrogen and ($C_1$-$C_4$)-alkyl. In another embodiment of the invention the groups $R^a$ are identical and chosen from hydrogen, fluorine and ($C_1$-$C_4$)-alkyl, or the two groups $R^a$ together are a divalent ($C_2$-$C_8$)-alkyl group. In another embodiment of the invention the groups $R^a$ both are hydrogen or the two groups $R^a$ together are a divalent ($C_2$-$C_8$)-alkyl group. In a further embodiment of the invention, the groups $R^a$ both are hydrogen, i.e. the group $C(R^a)_2$ representing the group A is the group $CH_2$. A ($C_1$-$C_4$)-alkyl group representing $R^a$ preferably is methyl.

In the diazacycloalkane moiety depicted in formula I, preferably one, two, three or four, more preferably one, two or three, particularly preferably one or two, for example one, of the groups R, which are independent of each other and can be identical or different, are defined as above or below and are chosen from all denotations comprised by the definition including hydrogen, and all other groups R are hydrogen. In one embodiment of the invention, all groups R are hydrogen and the diazacycloalkane moiety depicted in formula I is a piperazine ring, homopiperazine ring or 1,5-diazacane ring, in particular a piperazine ring, which carries the group $R^{10}$ but is not substituted by substituents on ring carbon atoms. Groups R which are different from hydrogen can be present in any positions of the diazacycloalkane moiety provided that the resulting compound of the formula I is stable and suitable as a subgroup in a pharmaceutical active compound. In one embodiment of the invention ($C_1$-$C_4$)-alkyl-O— groups representing R are not bonded to carbon atoms in the diazacycloalkane ring depicted in formula I which are adjacent to a ring nitrogen atom. Preferably only one or two, for example only one, of the groups R are ($C_1$-$C_4$)-alkyl-O—.

In one embodiment of the invention the groups R are chosen from hydrogen, ($C_1$-$C_4$)-alkyl, hydroxy-($C_1$-$C_4$)-alkyl-, ($C_1$-$C_4$)-alkyl-O—($C_1$-$C_4$)-alkyl-, phenyl-($C_1$-$C_4$)-alkyl-, ($C_1$-$C_4$)-alkyl-O—CO—$C_uH_{2u}$— and $R^1$—NH—CO—$C_uH_{2u}$—, in another embodiment from hydrogen, ($C_1$-$C_4$)-alkyl, hydroxy-($C_1$-$C_4$)-alkyl-, phenyl-($C_1$-$C_4$)-alkyl- and $R^1$—NH—CO—$C_uH_{2u}$—, in another embodiment from hydrogen, ($C_1$-$C_4$)-alkyl, hydroxy-($C_1$-$C_4$)-alkyl- and $R^1$—NH—CO—$C_uH_{2u}$—, in another embodiment from hydrogen, ($C_1$-$C_4$)-alkyl and hydroxy-($C_1$-$C_4$)-alkyl-, in another embodiment from hydrogen, ($C_1$-$C_4$)-alkyl and $R^1$—NH—$C_uH_{2u}$—, in another embodiment from hydrogen and ($C_1$-$C_4$)-alkyl, in another embodiment from hydrogen and $R^1$—NH—CO—$C_uH_{2u}$—, wherein all groups R are independent of each other and can be identical or different and phenyl is optionally substituted as indicated. In one embodiment of the invention one of the groups R is chosen from ($C_1$-$C_4$)-alkyl-O—CO—$C_uH_{2u}$— and $R^1$—NH—CO—$C_uH_{2u}$— and in particular is $R^1$—NH—CO—$C_uH_{2u}$—, and all other groups R are hydrogen. Groups R which are different from hydrogen, can be bonded to any ring carbon atoms in the diazacycloalkane ring depicted in formula I. In case two or more groups R are present which are different from hydrogen, a ring carbon atom can carry either one or two such groups R which are different from hydrogen. In case the diazacycloalkane ring depicted in formula I is a piperazine ring carrying one group R which is different from hydrogen, this group R can be present in the 2-position or the 3-position with respect to the ring nitrogen atom which is bonded to the CO group depicted in formula I. In case the diazacycloalkane ring depicted in formula I is a piperazine ring carrying two groups R which are different from hydrogen, these groups R can both be present in the 2-position, or they can both be present in the 3-position, or they can be present in positions 2 and 3, or in positions 2 and 5, or in positions 2 and 6, or in positions 3 and 5, with respect to the ring nitrogen atom which is bonded to the CO group depicted in formula I, where in case of two different groups R each of them can be present in each position. In one embodiment of the invention the number u is chosen from 0 and 1, in another embodiment u is chosen from 1 and 2, in another embodiment u is 0, in another embodiment u is 1, in another embodiment u is 2, wherein all numbers u are independent of each other and can be identical or different.

In one embodiment of the invention $R^1$ is chosen from ($C_1$-$C_4$)-alkyl, hydroxy-($C_1$-$C_4$)-alkyl- and $H_2N$—CO—($C_1$-

$C_4$)-alkyl-, in another embodiment from ($C_1$-$C_4$)-alkyl and hydroxy-($C_1$-$C_4$)-alkyl-, in another embodiment from ($C_1$-$C_4$)-alkyl and $H_2N$—CO—($C_1$-$C_4$)-alkyl-. In one embodiment of the invention $R^1$ is hydrogen, in another embodiment $R^1$ is ($C_1$-$C_4$)-alkyl, in another embodiment $R^1$ is hydroxy-($C_1$-$C_4$)-alkyl-, in another embodiment $R^1$ is $H_2N$—CO—($C_1$-$C_4$)-alkyl-.

$R^{10}$ is preferably chosen from hydrogen and ($C_1$-$C_6$)-alkyl-O—CO—, more preferably from hydrogen and ($C_1$-$C_4$)-alkyl-O—CO—. In one embodiment of the invention, $R^{10}$ is hydrogen.

In one embodiment of the invention, $R^{20}$ is chosen from phenyl and heteroaryl wherein heteroaryl is chosen from thiophenyl, thiazolyl and pyridinyl, in another embodiment from phenyl and heteroaryl wherein heteroaryl is thiophenyl, which are all optionally substituted as indicated. In another embodiment of the invention, $R^{20}$ is phenyl which is optionally substituted by one or more identical or different substituents chosen from halogen, ($C_1$-$C_4$)-alkyl, ($C_1$-$C_4$)-alkyl-O—, ($C_1$-$C_4$)-alkyl-S(O)$_m$—, hydroxy and cyano. Preferably the number of substituents in a substituted group $R^{20}$ is one, two, three or four, more preferably one, two or three, for example one or two. The substituents in a substituted group $R^{20}$ can be present on carbon atoms in any positions as indicated above with respect to substituted phenyl and heteroaryl groups in general. Thus, for example, in the case of a monosubstituted phenyl group representing $R^{20}$, the substituent can be present in the 2-position, the 3-position or the 4-position, and in the case of a disubstituted phenyl group the substituents can be present in positions 2 and 3, or positions 2 and 4, or positions 2 and 5, or positions 2 and 6, or positions 3 and 4, or positions 3 and 5. Likewise, a trisubstituted phenyl group representing $R^{20}$ can carry the substituents in any positions and can be a group such as 3-chloro-2,6-dimethyl-phenyl, 3-fluoro-2,6-dimethyl-phenyl, 6-chloro-3-fluoro-2-methyl-phenyl or 2-chloro-3-fluoro-6-methyl-phenyl, for example, in case of a phenyl group trisubstituted by fluorine and/or chlorine and methyl. The substituents which can be present in the group $R^{20}$, are preferably chosen from halogen, ($C_1$-$C_4$)-alkyl, ($C_1$-$C_4$)-alkyl-O—, ($C_1$-$C_4$)-alkyl-S(O)$_m$— and cyano, more preferably from halogen, ($C_1$-$C_4$)-alkyl, ($C_1$-$C_4$)-alkyl-O— and ($C_1$-$C_4$)-alkyl-S(O)$_m$—, particularly preferably from halogen, ($C_1$-$C_4$)-alkyl and ($C_1$-$C_4$)-alkyl-O—, more particularly preferably from halogen and ($C_1$-$C_4$)-alkyl, for example from chlorine, fluorine and methyl, wherein in one embodiment of the invention the alkyl groups in substituents in the group $R^{20}$ can be unsubstituted or substituted by one or more fluorine atoms and, as an example of substituents containing fluorine-substituted alkyl, the substituents comprising the group trifluoromethyl such as $CF_3$ itself, $CF_3$—O— or $CF_3$—S— may be included in each list of substituents in addition to substituents comprising unsubstituted alkyl, and in another embodiment of the invention the alkyl groups in substituents in the group $R^{20}$ are not substituted by fluorine and in this latter embodiment the said alkyl thus means unsubstituted alkyl. Specific groups in addition to the afore-mentioned specific groups, which can represent the group $R^{20}$ and from which, or from any subgroup of which, $R^{20}$ in the compounds of the formula I can be chosen, include phenyl, i.e. unsubstituted phenyl, 2-fluoro-phenyl, 3-fluoro-phenyl, 4-fluoro-phenyl, 2-chloro-phenyl, 3-chloro-phenyl, 4-chloro-phenyl, 2-methyl-phenyl (o-tolyl), 3-methyl-phenyl (m-tolyl), 4-methyl-phenyl (p-tolyl), 2-ethyl-phenyl, 3-ethyl-phenyl, 4-ethyl-phenyl, 2-methoxy-phenyl, 3-methoxy-phenyl, 4-methoxy-phenyl, 2,3-difluoro-phenyl, 2,4-difluoro-phenyl, 2,5-difluoro-phenyl, 2,6-difluoro-phenyl, 3,4-difluoro-phenyl, 3,5-difluoro-phenyl, 2,3-dichloro-phenyl, 2,4-dichloro-phenyl, 2,5-dichloro-phenyl, 2,6-dichloro-phenyl, 3,4-dichloro-phenyl, 3,5-dichloro-phenyl, 2-chloro-3-fluoro-phenyl, 2-chloro-4-fluoro-phenyl, 2-chloro-5-fluoro-phenyl, 2-chloro-6-fluoro-phenyl, 3-chloro-2-fluoro-phenyl, 3-chloro-4-fluoro-phenyl, 3-chloro-5-fluoro-phenyl, 4-chloro-2-fluoro-phenyl, 4-chloro-3-fluoro-phenyl, 5-chloro-2-fluoro-phenyl, 2,3-dimethyl-phenyl, 2,4-dimethyl-phenyl, 2,5-dimethyl-phenyl, 2,6-dimethyl-phenyl, 3,4-dimethyl-phenyl, 3,5-dimethyl-phenyl, 2-fluoro-3-methyl-phenyl, 2-fluoro-4-methyl-phenyl, 2-fluoro-5-methyl-phenyl, 2-fluoro-6-methyl-phenyl, 3-fluoro-2-methyl-phenyl, 3-fluoro-4-methyl-phenyl, 3-fluoro-5-methyl-phenyl, 4-fluoro-2-methyl-phenyl, 4-fluoro-3-methyl-phenyl, 5-fluoro-2-methyl-phenyl, 2-chloro-3-methyl-phenyl, 2-chloro-4-methyl-phenyl, 2-chloro-5-methyl-phenyl, 2-chloro-6-methyl-phenyl, 3-chloro-2-methyl-phenyl, 3-chloro-4-methyl-phenyl, 3-chloro-5-methyl-phenyl, 4-chloro-2-methyl-phenyl, 4-chloro-3-methyl-phenyl, 5-chloro-2-methyl-phenyl, 2-methoxy-3-methyl-phenyl, 2-methoxy-4-methyl-phenyl, 2-methoxy-5-methyl-phenyl, 2-methoxy-6-methyl-phenyl, 3-methoxy-2-methyl-phenyl, 3-methoxy-4-methyl-phenyl, 3-methoxy-5-methyl-phenyl, 4-methoxy-2-methyl-phenyl, 4-methoxy-3-methyl-phenyl, 5-methoxy-2-methyl-phenyl, for example.

In one embodiment of the invention, $R^{30}$ is chosen from ($C_3$-$C_7$)-cycloalkyl, ($C_5$-$C_7$)-cycloalkenyl, tetrahydropyranyl and phenyl, in another embodiment from ($C_3$-$C_7$)-cycloalkyl, ($C_5$-$C_7$)-cycloalkenyl and phenyl, in another embodiment from ($C_3$-$C_7$)-cycloalkyl, ($C_3$-$C_7$)-cycloalkenyl and tetrahydropyranyl, in another embodiment from ($C_3$-$C_7$)-cycloalkyl, ($C_5$-$C_5$)-cycloalkenyl, phenyl and heteroaryl, in another embodiment from ($C_3$-$C_7$)-cycloalkyl, phenyl and heteroaryl, in another embodiment from ($C_3$-$C_7$)-cycloalkyl and ($C_5$-$C_7$)-cycloalkenyl, in another embodiment from ($C_3$-$C_7$)-cycloalkyl and phenyl, wherein the cycloalkyl, cycloalkenyl, phenyl and heteroaryl groups are all optionally substituted as indicated and cycloalkyl preferably is ($C_5$-$C_7$)-cycloalkyl, more preferably ($C_5$-$C_6$)-cycloalkyl, for example cyclohexyl, cycloalkenyl preferably is ($C_5$-$C_6$)-cycloalkenyl, for example cyclohexenyl, and heteroaryl preferably is chosen from thiophenyl and pyridinyl. In another embodiment of the invention $R^{30}$ is phenyl which is optionally substituted as indicated. Preferably the number of substituents in a substituted group $R^{30}$ is one, two, three or four, more preferably one, two or three, particularly preferably one or two, for example one. The substituents in a substituted group $R^{30}$ can be present on carbon atoms in any positions as indicated above with respect to substituted cycloalkyl, cycloalkenyl, phenyl and heteroaryl groups in general. For example, in the case of a monosubstituted phenyl group representing $R^{30}$, the substituent can be present in the 2-position, the 3-position or the 4-position, and in the case of a disubstituted phenyl group the substituents can be present in positions 2 and 3, or positions 2 and 4, or positions 2 and 5, or positions 2 and 6, or positions 3 and 4, or positions 3 and 5. The substituents which can be present in a cycloalkyl or cycloalkenyl group representing $R^{30}$ are preferably chosen from fluorine, methyl and hydroxy, for example from fluorine and methyl. In one embodiment of the invention, the substituents in a cycloalkyl or cycloalkenyl group representing $R^{30}$ are hydroxy. In another embodiment of the invention, a cycloalkyl or cycloalkenyl group representing $R^{30}$ is unsubstituted. The substituents which can be present in a phenyl or heteroaryl group representing $R^{30}$, are preferably chosen from halogen, ($C_1$-$C_6$)-alkyl, hydroxy-($C_1$-$C_6$)-alkyl-, ($C_1$-$C_4$)-alkyl-O—($C_1$-$C_6$)-alkyl-, ($C_1$-$C_4$)-alkyl-CO—NH—($C_1$-$C_4$)-alkyl-, hydroxy, ($C_1$-$C_6$)-alkyl-O—, hydroxy-($C_1$-$C_6$)-alkyl-O—, $(C_1-C_4)$-alkyl-O—$(C_1-C_6)$-alkyl-O—, $(C_1-C_4)$-alkyl-CO—NH—$(C_1-C_4)$-alkyl-O—, $(C_1-C_6)$-alkyl-S(O)$_m$— and cyano, more preferably from halogen, $(C_1-C_6)$-alkyl, $(C_1-C_4)$-alkyl-O—$(C_1-C_6)$-alkyl-, hydroxy, $(C_1-C_6)$-alkyl-O—, $(C_1-C_4)$-alkyl-O—$(C_1-C_6)$-alkyl-O—, $(C_1-C_6)$-alkyl-S(O)$_m$— and cyano, particularly preferably from halogen, $(C_1-C_6)$-alkyl, $(C_1-C_4)$-alkyl-O—$(C_1-C_6)$-alkyl-, hydroxy, $(C_1-C_6)$-alkyl-O— and $(C_1-C_4)$-alkyl-O—$(C_1-C_6)$-alkyl-O—, more particularly preferably from halogen, $(C_1-C_6)$-alkyl, hydroxy, $(C_1-C_6)$-alkyl-O— and $(C_1-C_4)$-alkyl-O—$(C_1-C_6)$-alkyl-O—, especially preferably from halogen, $(C_1-C_6)$-alkyl, $(C_1-C_6)$-alkyl-O— and $(C_1-C_4)$-alkyl-O—$(C_1-C_6)$-alkyl-O—, for example from halogen, $(C_1-C_6)$-alkyl-O— and $(C_1-C_4)$-alkyl-O—$(C_1-C_6)$-alkyl-O— or from halogen, $(C_1-C_6)$-alkyl and $(C_1-C_6)$-alkyl-O— or from halogen and $(C_1-C_4)$-alkyl, wherein in one embodiment of the invention the alkyl groups in substituents in phenyl and heteroaryl groups representing $R^{30}$ can be unsubstituted or substituted by one or more fluorine atoms and, as an example of substituents containing fluorine-substituted alkyl, the substituents comprising the group trifluoromethyl such as $CF_3$ itself, $CF_3$—O— or $CF_3$—S— may be included in each list of substituents in addition to substituents comprising unsubstituted alkyl, and in another embodiment of the invention the alkyl groups in substituents in the group $R^{30}$ are not substituted by fluorine and in this latter embodiment the said alkyl thus means unsubstituted alkyl. In one embodiment of the invention, a $(C_1-C_6)$-alkyl group in a substituent in $R^{30}$ is a $(C_1-C_4)$-alkyl group. In one embodiment of the invention, the substituents which can be present in a phenyl or heteroaryl group representing $R^{30}$, are chosen from halogen, preferably from fluorine, chlorine and bromine, more preferably from fluorine and chlorine. Specific groups which can occur as the group $R^{30}$ and from which, or from any subgroup of which, $R^{30}$ in the compounds of the formula I can be chosen, include cyclopentyl, cyclohexyl, cycloheptyl, cyclopent-2-enyl, cyclohex-2-enyl, cyclohept-2-enyl, 4-fluoro-cyclohexyl, 4-methyl-cyclohexyl, 2-hydroxy-cyclopentyl, 3-hydroxy-cyclopentyl, 2-hydroxy-cyclohexyl, 3-hydroxy-cyclohexyl, 4-hydroxy-cyclohexyl, 2-hydroxy-cycloheptyl, 3-hydroxy-cycloheptyl, 4-hydroxy-cycloheptyl, 4,4-difluoro-cyclohexyl, 3,3-dimethyl-cyclohexyl, 4,4-dimethyl-cyclohexyl, tetrahydropyran-3-yl, tetrahydropyran-4-yl, phenyl, i.e. unsubstituted phenyl, 2-fluoro-phenyl, 3-fluoro-phenyl, 4-fluoro-phenyl, 2-chloro-phenyl, 3-chloro-phenyl, 4-chloro-phenyl, 3-bromo-phenyl, 4-bromo-phenyl, 2-methyl-phenyl, 3-methyl-phenyl, 4-methyl-phenyl, 2-hydroxy-phenyl, 3-hydroxy-phenyl, 4-hydroxy-phenyl, 2-methoxy-phenyl, 3-methoxy-phenyl, 4-methoxy-phenyl, 2-(2-methoxyethoxy)-phenyl, 3-(2-methoxyethoxy)-phenyl, 4-(2-methoxyethoxy)-phenyl, 2-(3-methoxypropoxy)-phenyl, 3-(3-methoxypropoxy)-phenyl, 4-(3-methoxypropoxy)-phenyl, thiophen-2-yl, thiophen-3-yl, pyridin-2-yl, pyridin-3-yl, pyridin-4-yl, 2-hydroxypyridin-3-yl, 4-hydroxypyridin-3-yl, 5-hydroxy-pyridin-3-yl, 6-hydroxy-pyridin-3-yl, 2-methoxy-pyridin-3-yl, 4-methoxy-pyridin-3-yl, 5-methoxy-pyridin-3-yl, 6-methoxy-pyridin-3-yl, 2-hydroxy-pyridin-4-yl, 3-hydroxy-pyridin-4-yl, 2-methoxy-pyridin-4-yl, 3-methoxy-pyridin-4-yl, for example.

The substituents $R^{40}$ can be present in any of positions 4 and/or 5 and/or 6 and/or 7 in the 6-membered ring of the indole ring depicted in formula I. In case the number n of the substituents $R^{40}$ is less than 4, all carbon atoms in positions 4, 5, 6 and 7 of the indole ring which do not carry a substituent $R^{40}$ carry a hydrogen atom, i.e. the respective ring members are CH groups. In case the number n is 0, all ring carbon atoms in positions 4, 5, 6 and 7 of the indole ring carry hydrogen atoms. Preferably, the number n of the substituents $R^{40}$ is chosen from 0, 1, 2 and 3, more preferably from 0, 1 and 2, for example from 0 and 1. In one embodiment of the invention the number n is 2. In another embodiment the number n is 1. In another embodiment the number n is 0, i.e. no substituent $R^{40}$ is present in the compound of the formula I. $R^{40}$ is preferably chosen from halogen, $(C_1-C_4)$-alkyl, phenyl-$(C_1-C_4)$-alkyl-, hydroxy-$(C_1-C_4)$-alkyl-, $(C_1-C_4)$-alkyl-O—$(C_1-C_4)$-alkyl-, hydroxy, $(C_1-C_4)$-alkyl-O—, hydroxy-$(C_1-C_4)$-alkyl-O—, $(C_1-C_4)$-alkyl-O—$(C_1-C_4)$-alkyl-O—, phenyl-O—$(C_1-C_4)$-alkyl-O—, di($(C_1-C_4)$-alkyl)N—$(C_1-C_4)$-alkyl-O—, HO—CO—$(C_1-C_4)$-alkyl-O—, $(C_1-C_4)$-alkyl-O—CO—$(C_1-C_4)$-alkyl-O—, $(C_1-C_4)$-alkyl-CO—O—, $(C_1-C_4)$-alkyl-NH—CO—O—, $(C_1-C_4)$-alkyl-S(O)$_m$—, HO—CO—, $(C_1-C_4)$-alkyl-O—CO—, $H_2N$—CO— and cyano, more preferably from halogen, $(C_1-C_4)$-alkyl, hydroxy-$(C_1-C_4)$-alkyl-, $(C_1-C_4)$-alkyl-O—$(C_1-C_4)$-alkyl-, hydroxy, $(C_1-C_4)$-alkyl-O—, hydroxy-$(C_1-C_4)$-alkyl-O—, $(C_1-C_4)$-alkyl-O—$(C_1-C_4)$-alkyl-O—, phenyl-O—$(C_1-C_4)$-alkyl-O—, di($(C_1-C_4)$-alkyl)N—$(C_1-C_4)$-alkyl-O—, $(C_1-C_4)$-alkyl-CO—O—, $(C_1-C_4)$-alkyl-NH—CO—O—, $(C_1-C_4)$-alkyl-S(O)$_m$—, HO—CO—, $(C_1-C_4)$-alkyl-O—CO—, $H_2N$—CO— and cyano, particularly preferably from halogen, $(C_1-C_4)$-alkyl, hydroxy-$(C_1-C_4)$-alkyl-, $(C_1-C_4)$-alkyl-O—$(C_1-C_4)$-alkyl-, hydroxy, $(C_1-C_4)$-alkyl-O—, hydroxy-$(C_1-C_4)$-alkyl-O—, $(C_1-C_4)$-alkyl-O—$(C_1-C_4)$-alkyl-O—, phenyl-O—$(C_1-C_4)$-alkyl-O—, di($(C_1-C_4)$-alkyl)N—$(C_1-C_4)$-alkyl-O—, $(C_1-C_4)$-alkyl-CO—O—, $(C_1-C_4)$-alkyl-NH—CO—O—, HO—CO—, $(C_1-C_4)$-alkyl-O—CO— and $H_2N$—CO—, more particularly preferably from halogen, $(C_1-C_4)$-alkyl, hydroxy, $(C_1-C_4)$-alkyl-O—, $(C_1-C_4)$-alkyl-O—$(C_1-C_4)$-alkyl-O—, $(C_1-C_4)$-alkyl-CO—O—, $(C_1-C_4)$-alkyl-NH—CO—O—, $(C_1-C_4)$-alkyl-O—CO— and $H_2N$—CO—, especially preferably from halogen, $(C_1-C_4)$-alkyl, hydroxy, $(C_1-C_4)$-alkyl-O—, $(C_1-C_4)$-alkyl-O—$(C_1-C_4)$-alkyl-O—, $(C_1-C_4)$-alkyl-O—CO— and $H_2N$—CO—, wherein all substituents $R^{40}$ are independent of each other and can be identical or different, and wherein all phenyl groups are independently of each other optionally substituted as indicated. In one embodiment of the invention, $R^{40}$ is chosen from halogen, $(C_1-C_4)$-alkyl, hydroxy, $(C_1-C_4)$-alkyl-O—, $(C_1-C_4)$-alkyl-O—$(C_1-C_4)$-alkyl-O—, $(C_1-C_4)$-alkyl-CO—O—, $(C_1-C_4)$-alkyl-NH—CO—O—, $(C_1-C_4)$-alkyl-O—CO—, HO—CO—$(C_1-C_4)$-alkyl-O—, $(C_1-C_4)$-alkyl-O—CO—$(C_1-C_4)$-alkyl-O— and $H_2N$—CO—, preferably from halogen, $(C_1-C_4)$-alkyl, hydroxy, $(C_1-C_4)$-alkyl-O—, $(C_1-C_4)$-alkyl-O—$(C_1-C_4)$-alkyl-O—, $(C_1-C_4)$-alkyl-O—CO— and $H_2N$—CO—, for example from halogen, $(C_1-C_4)$-alkyl, hydroxy, $(C_1-C_4)$-alkyl-O—, $(C_1-C_4)$-alkyl-O—CO— and $H_2N$—CO— or from halogen, $(C_1-C_4)$-alkyl, hydroxy, $(C_1-C_4)$-alkyl-O— and $(C_1-C_4)$-alkyl-O—$(C_1-C_4)$-alkyl-O— or from halogen, $(C_1-C_4)$-alkyl, hydroxy and $(C_1-C_4)$-alkyl-O—, wherein all substituents $R^{40}$ are independent of each other and can be identical or different. Preferably, not more than two of the substituents $R^{40}$ are $NO_2$. In one embodiment of the invention, the number n is chosen from 1, 2, 3 and 4, preferably from 1, 2 and 3, more preferably from 1 and 2, and can be 1, for example. I.e., in this latter embodiment at least one substituent $R^{40}$ is present in the compounds of the formula I, preferably one, two or three substituents $R^{40}$, more preferably one or two substituents $R^{40}$, for example one substituent $R^{40}$.

In one embodiment of the invention at least one substituent $R^{40}$ which can be present in the compounds of the formula I, preferably one or two substituents $R^{40}$, for example one substituent $R^{40}$, is a substituent wherein the atom within the substituent via which it is bonded to the carbon atom in the 6-membered ring of the indole moiety, is an oxygen atom, i.e., it is chosen from hydroxy, $(C_1$-$C_4)$-alkyl-O—, $(C_3$-$C_7)$-cycloalkyl-$C_vH_{2v}$—O—, phenyl-$(C_1$-$C_4)$-alkyl-O—, heteroaryl-$(C_1$-$C_4)$-alkyl-O—, hydroxy-$(C_1$-$C_4)$-alkyl-O—, $(C_1$-$C_4)$-alkyl-O—$(C_1$-$C_4)$-alkyl-O—, $(C_3$-$C_7)$-cycloalkyl-$C_vH_{2v}$—O—$(C_1$-$C_4)$-alkyl-O—, phenyl-O—$(C_1$-$C_4)$-alkyl-O—, heteroaryl-O—$(C_1$-$C_4)$-alkyl-O—, di$((C_1$-$C_4)$-alkyl)N—$(C_1$-$C_4)$-alkyl-O—, HO—CO—$(C_1$-$C_4)$-alkyl-O—, $(C_1$-$C_4)$-alkyl-O—CO—$(C_1$-$C_4)$-alkyl-O—, $H_2N$—CO—$(C_1$-$C_4)$-alkyl-O—, $(C_1$-$C_4)$-alkyl-CO—O—, $(C_3$-$C_7)$-cycloalkyl-$C_vH_{2v}$—CO—O—, $(C_1$-$C_4)$-alkyl-NH—CO—O— and $(C_3$-$C_7)$-cycloalkyl-$C_vH_{2v}$—NH—CO—O—, wherein such substituents are independent of each other and can be identical or different and wherein all phenyl and heteroaryl groups can independently of each other be substituted as indicated. Preferably, such substituents are chosen from hydroxy, $(C_1$-$C_4)$-alkyl-O—, hydroxy-$(C_1$-$C_4)$-alkyl-O—, $(C_1$-$C_4)$-alkyl-O—$(C_1$-$C_4)$-alkyl-O—, phenyl-O—$(C_1$-$C_4)$-alkyl-O—, di$((C_1$-$C_4)$-alkyl)N—$(C_1$-$C_4)$-alkyl-O—, $(C_1$-$C_4)$-alkyl-CO—O— and $(C_1$-$C_4)$-alkyl-NH—CO—O—, and more preferably from hydroxy, $(C_1$-$C_4)$-alkyl-O—, $(C_1$-$C_4)$-alkyl-O—$(C_1$-$C_4)$-alkyl-O—, phenyl-O—$(C_1$-$C_4)$-alkyl-O—, di$((C_1$-$C_4)$-alkyl)N—$(C_1$-$C_4)$-alkyl-O— and $(C_1$-$C_4)$-alkyl-CO—O—, particularly preferably from hydroxy, $(C_1$-$C_4)$-alkyl-O—, $(C_1$-$C_4)$-alkyl-O—$(C_1$-$C_4)$-alkyl-O—, phenyl-O—$(C_1$-$C_4)$-alkyl-O— and di$((C_1$-$C_4)$-alkyl)N—$(C_1$-$C_4)$-alkyl-O—, more particularly preferably are chosen from hydroxy, $(C_1$-$C_4)$-alkyl-O—, $(C_1$-$C_4)$-alkyl-O—$(C_1$-$C_4)$-alkyl-O— and phenyl-O—$(C_1$-$C_4)$-alkyl-O—, especially preferably from hydroxy, $(C_1$-$C_4)$-alkyl-O— and $(C_1$-$C_4)$-alkyl-O—$(C_1$-$C_4)$-alkyl-O—, more especially preferably from hydroxy and $(C_1$-$C_4)$-alkoxy. In one embodiment, such substituents are chosen from hydroxy, $(C_1$-$C_4)$-alkyl-O—, hydroxy-$(C_1$-$C_4)$-alkyl-O—, $(C_1$-$C_4)$-alkyl-O—$(C_1$-$C_4)$-alkyl-O—, phenyl-O—$(C_1$-$C_4)$-alkyl-O—, di$((C_1$-$C_4)$-alkyl)N—$(C_1$-$C_4)$-alkyl-O—, HO—CO—$(C_1$-$C_4)$-alkyl-O—, $(C_1$-$C_4)$-alkyl-O—CO—$(C_1$-$C_4)$-alkyl-O—, $H_2N$—CO—$(C_1$-$C_4)$-alkyl-O—, $(C_1$-$C_4)$-alkyl-CO—O— and $(C_1$-$C_4)$-alkyl-NH—CO—O—, preferably from hydroxy, $(C_1$-$C_4)$-alkyl-O—, $(C_1$-$C_4)$-alkyl-O—$(C_1$-$C_4)$-alkyl-O—, di$((C_1$-$C_4)$-alkyl)N—$(C_1$-$C_4)$-alkyl-O—, HO—CO—$(C_1$-$C_4)$-alkyl-O—, $(C_1$-$C_4)$-alkyl-O—CO—$(C_1$-$C_4)$-alkyl-O— and $H_2N$—CO—$(C_1$-$C_4)$-alkyl-O—, more preferably from hydroxy, $(C_1$-$C_4)$-alkyl-O—, $(C_1$-$C_4)$-alkyl-O—$(C_1$-$C_4)$-alkyl-O—, di$((C_1$-$C_4)$-alkyl)N—$(C_1$-$C_4)$-alkyl-O—, HO—CO—$(C_1$-$C_4)$-alkyl-O— and $(C_1$-$C_4)$-alkyl-O—CO—$(C_1$-$C_4)$-alkyl-O—, particularly preferably from hydroxy, $(C_1$-$C_4)$-alkyl-O—, $(C_1$-$C_4)$-alkyl-O—$(C_1$-$C_4)$-alkyl-O— and di$((C_1$-$C_4)$-alkyl)N—$(C_1$-$C_4)$-alkyl-O—, more particularly preferably from hydroxy, $(C_1$-$C_4)$-alkyl-O— and $(C_1$-$C_4)$-alkyl-O—$(C_1$-$C_4)$-alkyl-O—, especially preferably from preferably from hydroxy and $(C_1$-$C_4)$-alkyl-O—, wherein such substituents are independent of each other and can be identical or different. If besides such substituents bonded via an oxygen atom further substituents $R^{40}$ are present in a compound of the formula I, they are chosen from all other meanings of $R^{40}$ listed above, and preferably are chosen from halogen and $(C_1$-$C_4)$-alkyl, wherein all such further substituents are independent of each other and can be identical or different. In one embodiment, one such substituent $R^{40}$ bonded via an oxygen atom is present in position 5 or in position 6 of the indole ring. In another embodiment two identical or different such substituents are present in positions 5 and 6 of the indole ring.

In a compound of the formula I which contains one substituent $R^{40}$, the substituent can be present in position 4 or position 5 or position 6 or position 7 of the indole ring. In a compound of the formula I which contains two substituents $R^{40}$, the substituents can be present in positions 4 and 5 or positions 4 and 6 or positions 4 and 7 or positions 5 and 6 or positions 5 and 7 or positions 6 and 7 of the indole ring. In a compound of the formula I which contains three substituents $R^{40}$, the substituents can be present in positions 4, 5 and 6 or in positions 4, 5 and 7 or in positions 4, 6 and 7 or in positions 5, 6 and 7. In one embodiment of the invention, the compounds of the formula I contain zero, one or two substituents $R^{40}$ wherein the substituents $R^{40}$ are present in position 4 or position 5 or in positions 4 and 5 and the other of positions 4, 5, 6 and 7 carry hydrogen atoms. In another embodiment of the invention, the compounds of the formula I contain zero, one or two substituents $R^{40}$ wherein the substituents $R^{40}$ are present in position 4 or position 6 or in positions 4 and 6 and the other of positions 4, 5, 6 and 7 carry hydrogen atoms. In another embodiment of the invention, the compounds of the formula I contain zero, one or two substituents $R^{40}$ wherein the substituents $R^{40}$ are present in position 4 or position 7 or in positions 4 and 7 and the other of positions 4, 5, 6 and 7 carry hydrogen atoms. In another embodiment of the invention, the compounds of the formula I contain zero, one or two substituents $R^{40}$ wherein the substituents $R^{40}$ are present in position 5 or position 6 or in positions 5 and 6 and the other of positions 4, 5, 6 and 7 carry hydrogen atoms. In another embodiment of the invention, the compounds of the formula I contain zero, one or two substituents $R^{40}$ wherein the substituents $R^{40}$ are present in position 5 or position 7 or in positions 5 and 7 and the other of positions 4, 5, 6 and 7 carry hydrogen atoms. In another embodiment of the invention, the compounds of the formula I contain zero, one or two substituents $R^{40}$ wherein the substituents $R^{40}$ are present in position 6 or position 7 or in positions 6 and 7 and the other of positions 4, 5, 6 and 7 carry hydrogen atoms.

In one embodiment of the invention the number p is 2 and the number q is chosen from 2 and 3. In another embodiment of the invention both p and q are 2, i.e., the diazacycloalkane ring depicted in formula I is a piperazine ring and the compound of the formula I is a compound of the formula Ia. In another embodiment of the invention p is 2 and q is 3, i.e., the diazacycloalkane ring depicted in formula I is a homopiperazine ring and the compound of the formula I is a compound of the formula Ib. In another embodiment of the invention both p and q are 3, i.e., the diazacycloalkane ring depicted in formula I is a 1,5-diazocane ring and the compound of the formula I is a compound of the formula Ic. A, R, $R^{10}$, $R^{20}$, $R^{30}$, $R^{40}$ and n in the formulae Ia, Ib and Ic are defined as in formula I.

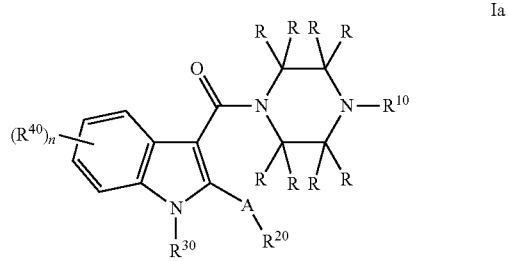

Ia

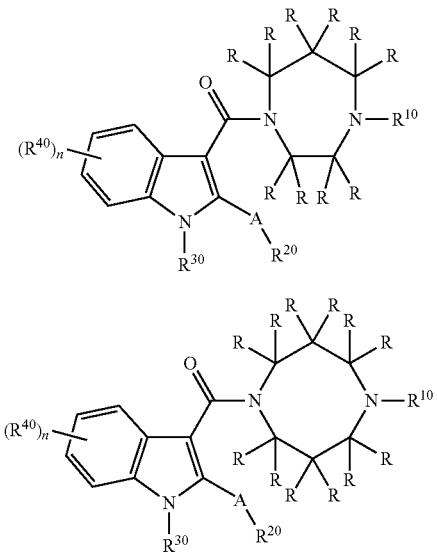

In preferred compounds of the invention any one or more structural elements such as groups, substituents and numbers are defined as in any of the preferred definitions of the elements or in any specified embodiment and/or can have one or more of the specific meanings which are mentioned as examples of elements, wherein all combinations of one or more preferred definitions and embodiments and/or specific meanings are a subject of the present invention. Also with respect to all preferred compounds of the formula I, all their stereoisomeric forms and mixtures of stereoisomeric forms in all ratios, and their physiologically acceptable salts, and the physiologically acceptable solvates of any of them, are a subject of the present invention. Similarly, also with respect to all specific compounds disclosed herein, such as the example compounds, which represent embodiments of the invention wherein the various groups and numbers in the general definition of the compounds of the formula I have the specific meanings present in the respective specific compound, all their stereoisomeric forms and mixtures of stereoisomeric forms in all ratios, and their physiologically acceptable salts, and the physiologically acceptable solvates of any of them, are a subject of the present invention. In particular, a subject of the invention are all specific compounds disclosed herein, independently thereof whether they are disclosed as a free compound and/or as a specific salt, both in the form of the free compound and in the form of all its physiologically acceptable salts, and if a specific salt is disclosed, additionally in the form of this specific salt, and the physiologically acceptable solvates thereof.

As an example of compounds of the invention in which any one or more structural elements are defined as in preferred definitions, compounds of the formula I may be mentioned wherein p and q are both 2, $R^{10}$ is hydrogen and A is chosen from O and $C(R^a)_2$, i.e. the compounds of the formula Ia wherein $R^{10}$ is hydrogen and A is chosen from O and $C(R^a)_2$, and all other groups and numbers are defined as in the general definition of the compounds of the formula I or in any of the preferred definitions or embodiments of the invention, in any of their stereoisomeric forms or a mixture of stereoisomeric forms in any ratio, and the physiologically acceptable salts thereof, and the physiologically acceptable solvates of any of them.

Another such example are compounds of the formula I, in any of their stereoisomeric forms or a mixture of stereoisomeric forms in any ratio, and the physiologically acceptable salts thereof, and the physiologically acceptable solvates of any of them, wherein A is chosen from O, S, $NCH_3$ and $C(R^a)_2$;

$R^a$ is chosen from hydrogen, fluorine and methyl, wherein the two groups $R^a$ are independent of each other and can be identical or different, or the two groups $R^a$ together are a divalent $(C_2\text{-}C_5)$-alkyl group;

R is chosen from hydrogen, $(C_1\text{-}C_4)$-alkyl, hydroxy-$(C_1\text{-}C_4)$-alkyl-, $(C_1\text{-}C_4)$-alkyl-O—$(C_1\text{-}C_4)$-alkyl-, phenyl-$(C_1\text{-}C_4)$-alkyl-, $(C_1\text{-}C_4)$-alkyl-O—CO—$C_uH_{2u}$— and $R^1$—NH—CO—$C_uH_{2u}$—, wherein all groups R are independent of each other and can be identical or different;

$R^1$ is chosen from $(C_1\text{-}C_4)$-alkyl, hydroxy-$(C_1\text{-}C_4)$-alkyl- and $H_2N$—CO—$(C_1\text{-}C_4)$-alkyl-;

$R^{10}$ is chosen from hydrogen, $(C_1\text{-}C_6)$-alkyl-O—CO— and $(C_3\text{-}C_7)$-cycloalkyl-$C_vH_{2v}$—O—CO—;

$R^{20}$ is chosen from phenyl and heteroaryl, which are optionally substituted by one or more identical or different substituents chosen from halogen, $(C_1\text{-}C_4)$-alkyl, $(C_1\text{-}C_4)$-alkyl-O—, $(C_1\text{-}C_4)$-alkyl-S(O)$_m$—, hydroxy and cyano;

$R^{30}$ is chosen from $(C_3\text{-}C_7)$-cycloalkyl, $(C_5\text{-}C_7)$-cycloalkenyl, tetrahydropyranyl, phenyl and heteroaryl, wherein cycloalkyl and cycloalkenyl are optionally substituted by one or more identical or different substituents chosen from fluorine, $(C_1\text{-}C_4)$-alkyl and hydroxy, and phenyl and heteroaryl are optionally substituted by one or more identical or different substituents chosen from halogen, $(C_1\text{-}C_6)$-alkyl, $(C_1\text{-}C_4)$-alkyl-O—$(C_1\text{-}C_6)$-alkyl-, hydroxy, $(C_1\text{-}C_6)$-alkyl-O—, $(C_1\text{-}C_4)$-alkyl-O—$(C_1\text{-}C_6)$-alkyl-O—, $(C_1\text{-}C_6)$-alkyl-S(O)$_m$— and cyano;

$R^{40}$ is chosen from halogen, $(C_1\text{-}C_4)$-alkyl, hydroxy-$(C_1\text{-}C_4)$-alkyl-, $(C_1\text{-}C_4)$-alkyl-O—$(C_1\text{-}C_4)$-alkyl-, hydroxy, $(C_1\text{-}C_4)$-alkyl-O—, hydroxy-$(C_1\text{-}C_4)$-alkyl-O—, $(C_1\text{-}C_4)$-alkyl-O—$(C_1\text{-}C_4)$-alkyl-O—, phenyl-O—$(C_1\text{-}C_4)$-alkyl-O—, di($(C_1\text{-}C_4)$-alkyl)N—$(C_1\text{-}C_4)$-alkyl-O—, $(C_1\text{-}C_4)$-alkyl-CO—O—, $(C_1\text{-}C_4)$-alkyl-NH—CO—O—, $(C_1\text{-}C_4)$-alkyl-S(O)$_m$—, HO—CO—, $(C_1\text{-}C_4)$-alkyl-O—CO—, $H_2N$—CO— and cyano, wherein all substituents $R^{40}$ are independent of each other and can be identical or different;

heteroaryl is chosen from thiophenyl and pyridinyl;

m is chosen from 0, 1 and 2, wherein all numbers m are independent of each other and can be identical or different;

n is chosen from 0, 1, 2 and 3;

p is 2 and q is chosen from 2 and 3;

u is chosen from 0, 1 and 2, wherein all numbers u are independent of each other and can be identical or different;

v is chosen from 0, 1 and 2;

wherein all alkyl groups, independently of each other, are optionally substituted by one or more fluorine atoms;

wherein the cycloalkyl group is optionally substituted by one or more identical or different substituents chosen from flourine and $(C_1\text{-}C_4)$-alkyl, unless specified otherwise;

wherein all phenyl groups present in R and $R^{40}$, independently of each other, are optionally substituted by one or more identical of different substituents chosen from halogen, $(C_1\text{-}C_4)$-alkyl, $(C_1\text{-}C_4)$-alkyl-O—, $(C_1\text{-}C_4)$-alkyl-S(O)$_2$— and cyano.

Another such example are compounds of the formula I, in any of their stereoisomeric forms or a mixture of stereoisomeric forms in any ratio, and the physiologically acceptable salts thereof, and the physiologically acceptable solvates of any of them, wherein A is chosen from O, S and $C(R^a)_2$;

$R^a$ is chosen from hydrogen, fluorine and methyl, wherein the two groups $R^a$ are independent of each other and can be identical or different, or the two groups $R^a$ together are a divalent $(C_2\text{-}C_5)$-alkyl group;

R is chosen from hydrogen, $(C_1\text{-}C_4)$-alkyl, hydroxy-$(C_1\text{-}C_4)$-alkyl-, $(C_1\text{-}C_4)$-alkyl-O—$(C_1\text{-}C_4)$-alkyl-, phenyl-$(C_1\text{-}C_4)$-alkyl-, $(C_1\text{-}C_4)$-alkyl-O—CO—$C_uH_{2u}$— and $R^1$—NH—CO—$C_uH_{2u}$—, wherein all groups R are independent of each other and can be identical or different;

$R^1$ is chosen from $(C_1\text{-}C_4)$-alkyl, hydroxy-$(C_1\text{-}C_4)$-alkyl- and $H_2N$—CO—$(C_1\text{-}C_4)$-alkyl-;

$R^{10}$ is chosen from hydrogen, $(C_1\text{-}C_6)$-alkyl-O—CO— and $(C_3\text{-}C_7)$-cycloalkyl-$C_vH_{2v}$—O—CO—;

$R^{20}$ is chosen from phenyl and heteroaryl which are optionally substituted by one or more identical or different substituents chosen from halogen, $(C_1\text{-}C_4)$-alkyl, $(C_1\text{-}C_4)$-alkyl-O—, $(C_1\text{-}C_4)$-alkyl-S(O)$_m$—, hydroxy and cyano;

$R^{30}$ is chosen from $(C_3\text{-}C_7)$-cycloalkyl, $(C_5\text{-}C_7)$-cycloalkenyl, tetrahydropyranyl, phenyl and heteroaryl, wherein cycloalkyl and cycloalkenyl are optionally substituted by one or more identical or different substituents chosen from fluorine, $(C_1\text{-}C_4)$-alkyl and hydroxy, and phenyl and heteroaryl are optionally substituted by one or more identical or different substituents chosen from halogen, $(C_1\text{-}C_6)$-alkyl, $(C_1\text{-}C_4)$-alkyl-O—$(C_1\text{-}C_6)$-alkyl-, hydroxy, $(C_1\text{-}C_6)$-alkyl-O—, $(C_1\text{-}C_4)$-alkyl-O—$(C_1\text{-}C_6)$-alkyl-O—, $(C_1\text{-}C_6)$-alkyl-S(O)$_m$— and cyano;

$R^{40}$ is chosen from halogen, $(C_1\text{-}C_4)$-alkyl, hydroxy-$(C_1\text{-}C_4)$-alkyl-, $(C_1\text{-}C_4)$-alkyl-O—$(C_1\text{-}C_4)$-alkyl-, hydroxy, $(C_1\text{-}C_4)$-alkyl-O—, hydroxy-$(C_1\text{-}C_4)$-alkyl-O—, $(C_1\text{-}C_4)$-alkyl-O—$(C_1\text{-}C_4)$-alkyl-O—, phenyl-O—$(C_1\text{-}C_4)$-alkyl-O—, di($(C_1\text{-}C_4)$-alkyl)N—$(C_1\text{-}C_4)$-alkyl-O—, $(C_1\text{-}C_4)$-alkyl-CO—O—, $(C_1\text{-}C_4)$-alkyl-NH—CO—O—, HO—CO—, $(C_1\text{-}C_4)$-alkyl-O—CO— and $H_2N$—CO—, wherein all substituents $R^{40}$ are independent of each other and can be identical or different;

heteroaryl is chosen from thiophenyl and pyridinyl;

m is chosen from 0, 1 and 2, wherein all numbers m are independent of each other and can be identical or different;

n is chosen from 0, 1 and 2;

p and q are 2;

u is chosen from 0, 1 and 2, wherein all numbers u are independent of each other and can be identical or different;

v is chosen from 0, 1 and 2;

wherein all alkyl groups, independently of each other, are optionally substituted by one or more fluorine atoms;

wherein the cycloalkyl group is optionally substituted by one or more identical or different substituents chosen from flourine and $(C_1\text{-}C_4)$-alkyl, unless specified otherwise;

wherein all phenyl groups present in R and $R^{40}$, independently of each other, are optionally substituted by one or more identical of different substituents chosen from halogen, $(C_1\text{-}C_4)$-alkyl, $(C_1\text{-}C_4)$-alkyl-O—, $(C_1\text{-}C_4)$-alkyl-S(O)$_2$— and cyano.

Another such example are compounds of the formula I, in any of their stereoisomeric forms or a mixture of stereoisomeric forms in any ratio, and the physiologically acceptable salts thereof, and the physiologically acceptable solvates of any of them, wherein A is chosen from O and $C(R^a)_2$;

$R^a$ is hydrogen;

R is chosen from hydrogen, $(C_1\text{-}C_4)$-alkyl, hydroxy-$(C_1\text{-}C_4)$-alkyl- and $R^1$—NH—CO—$C_uH_{2u}$—, wherein all groups R are independent of each other and can be identical or different;

$R^1$ is chosen from $(C_1\text{-}C_4)$-alkyl, hydroxy-$(C_1\text{-}C_4)$-alkyl- and $H_2N$—CO—$(C_1\text{-}C_4)$-alkyl-;

$R^{10}$ is hydrogen;

$R^{20}$ is phenyl which is optionally substituted by one or more identical or different substituents chosen from halogen and $(C_1\text{-}C_4)$-alkyl;

$R^{30}$ is chosen from $(C_5\text{-}C_7)$-cycloalkyl, $(C_5\text{-}C_7)$-cycloalkenyl, tetrahydropyranyl and phenyl, wherein phenyl is optionally substituted by one or more identical or different substituents chosen from halogen, $(C_1\text{-}C_6)$-alkyl, hydroxy, $(C_1\text{-}C_6)$-alkyl-O— and $(C_1\text{-}C_4)$-alkyl-O—$(C_1\text{-}C_6)$-alkyl-O—;

$R^{40}$ is chosen from halogen, $(C_1\text{-}C_4)$-alkyl, hydroxy, $(C_1\text{-}C_4)$-alkyl-O—, $(C_1\text{-}C_4)$-alkyl-O—$(C_1\text{-}C_4)$-alkyl-O—, $(C_1\text{-}C_4)$-alkyl-O—CO— and $H_2N$—CO—, wherein all substituents $R^{40}$ are independent of each other and can be identical or different;

n is chosen from 0, 1 and 2;

p and q are 2;

u is chosen from 0, 1 and 2, wherein all numbers u are independent of each other and can be identical or different;

wherein all alkyl groups, independently of each other, are optionally substituted by one or more fluorine atoms.

Another subject of the present invention are processes for the preparation of the compounds of the formula I, including their salts and solvates, which are outlined below and by which the compounds are obtainable. For example, the preparation of the compounds of the formula I can be carried out by first reacting an indole of the formula II on the ring nitrogen atom with an alkylating or arylating compound of the

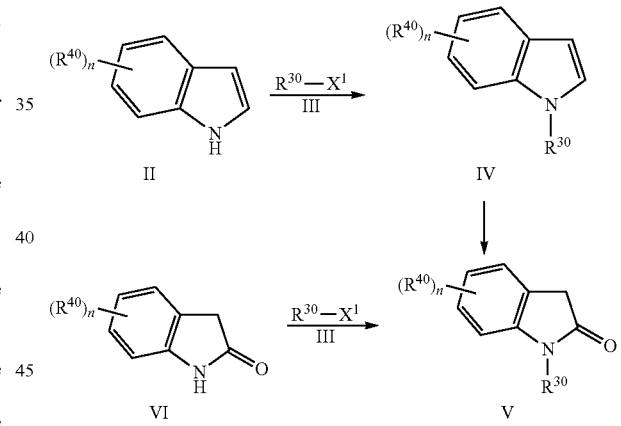

formula III to give a compound of the formula IV which is then converted into a 1,3-dihydro-indol-2-one (oxindole) of the formula V. The groups $R^{30}$ and $R^{40}$ and the number n in the compounds of the formulae II, III, IV and V are defined as in the compounds of the formula I and additionally functional groups can be present in protected form or in the form of a precursor group which is later converted into the final group. The group $X^1$ in the compounds of the formula III is a substitutable group allowing a nucleophilic substitution reaction or a reaction of another mechanistic type, including radical reactions and transition metal-catalyzed reactions, which results in the replacement of such a substitutable group by the ring nitrogen atom in the compound of the formula II, for example halogen or an arylsulfonyloxy or alkylsulfonyloxy group or a boron-containing group.

In case $R^{30}$ is optionally substituted phenyl or heteroaryl which is substituted with a suitable electron-accepting group or comprises an electron-deficient heterocyclic ring, or $R^{30}$ is optionally substituted cycloalkyl or cycloalkenyl or is tetrahydropyranyl, $X^1$ can be halogen, in particular chlorine, bromine or iodine, or an arylsulfonyloxy or alkylsulfonyloxy group such as benzenesulfonyloxy, toluenesulfonyloxy, nitrobenzenesulfonyloxy, methanesulfonyloxy or trifluoromethanesulfonyloxy, and the reaction can be performed under the conditions of a nucleophilic substitution reaction, usually in a solvent, for example an inert aprotic solvent such as an ether like tetrahydrofuran (THF), dioxane (1,4-dioxane) or ethylene glycol dimethyl ether (DME), an amide like dimethylformamide (DMF) or N-methyl-pyrrolidin-2-one (NMP), or dimethyl sulfoxide (DMSO), or a mixture thereof, and in the presence of a base such as an alcoholate like sodium ethoxide or potassium tert-butoxide, a hydride like sodium hydride, an amide like sodium amide or lithium diisopropylamide, a carbonate like potassium carbonate or cesium carbonate, or an amine like ethyldiisopropylamine.

In case $R^{30}$ is optionally substituted phenyl or heteroaryl, $X^1$ can be chlorine, bromine or iodine, i.e. the compound of the formula III be an optionally substituted chlorobenzene, bromobenzene, iodobenzene, chloroheteroarene, bromoheteroarene or iodoheteroarene, and the reaction of the compounds of the formula II and III can be performed under the conditions of the Ullmann arylation reaction in the presence of a catalytic copper compound, for example copper(I) bromide, copper(I) iodide or copper(II) acetylacetonate, at elevated temperatures, for example at temperatures from about 100° C. to about 150° C., usually in an inert aprotic solvent such as DMSO, DMF, NMP, acetonitrile, dioxane or toluene in the presence of a base such as a carbonate like potassium carbonate or cesium carbonate or a phosphate like tribasic potassium phosphate and favorably an amine like N,N'-dimethylethylenediamine, 1,2-diaminocyclohexane, proline or 8-hydroxyquinoline. The arylation reaction, like other reactions performed in the synthesis of the compounds of the formula I, can also be carried out in a microwave reactor.

In another method for the preparation of compounds of the formula IV a compound of the formula II can be reacted with a compound of the formula III in which $R^{30}$ is optionally substituted phenyl or heteroaryl and $X^1$ is halogen, in particular chlorine, bromine or iodine, or an alkylsulfonyloxy group such as trifluoromethanesulfonyloxy, in the presence of a palladium catalyst, which can be formed from tris(dibenzylideneacetone)dipalladium(0) and a phosphine ligand, for example, and a base such as sodium tert-butoxide or tribasic potassium phosphate in an inert solvent such as a hydrocarbon like toluene or an ether like dioxane at temperatures from about 60° C. to about 120° C., as described in D. W. Old et al., Org. Lett. 2 (2000), 1403, for example.

In a further method for the preparation of compounds of the formula IV, a compound of the formula II can be reacted with a boronic acid, i.e. a compound of the formula III wherein $X^1$ is a boronic acid group $B(OH)_2$, in a transition metal-catalyzed reaction for example according to the Chan-Evans-Lam modification of the Suzuki-Miyaura coupling reaction in the presence of a copper compound such as copper(II) acetate in a solvent such as a chlorinated hydrocarbon like dichloromethane or chloroform at temperatures from about 20° C. to about 40° C., for example at room temperature, and in the presence of a tertiary amine such as triethylamine, ethyldiisopropylamine or pyridine, as described in D. M. T. Chan et al., Tetrahedron Lett. 39 (1998), 2933, for example. Instead of with a boronic acid, a compound of the formula IV can also be obtained from a compound of the formula II with an organotrifluoroborate salt, i.e. a compound of the formula III wherein $X^1$ is a negatively charged trifluoroborate group $BF_3^-$ having a cation such as an alkaline metal cation like a cesium, potassium, sodium or lithium cation or a quaternary ammonium or phosphonium cation, in particular a potassium cation, as counterion (cf. R. A. Batey et al., Tetrahedron Lett. 42 (2001), 9099), in the presence of a catalytic transition metal compound such as a copper compound like copper(II) acetate in a solvent such as a chlorinated hydrocarbon like dichloromethane or chloroform at temperatures from about 20° C. to about 50° C. in the presence of oxygen and molecular sieves, as described in T. D. Quach et al., Org. Lett. (2003), 4397, for example.

The subsequent conversion of the compound of the formula IV into the oxindole of the formula V can be carried out by first treating the compound of the formula IV with N-chlorosuccinimide in a solvent such as a chlorinated hydrocarbon like dichloromethane at temperatures from about 10° C. to about 30° C., for example at room temperature, and then treating the crude intermediate product with 85% phosphoric acid in acetic acid at elevated temperatures from about 110° C. to about 140° C., as described in R. Sarges et al., J. Med. Chem. 32 (1989), 437. The conversion of a compound of the formula IV to an oxindole of the formula V can also be carried out by first treating the compound of the formula IV with bromine or a bromine source such as N-bromosuccinimide or pyridinium bromide perbromide (pyridinium tribromide) in a solvent such as a chlorinated hydrocarbon like dichloromethane or an alcohol like tert-butanol or amyl alcohol or a mixture of an alcohol and water or an aqueous buffer solution like a phosphate buffer having a pH of about 5, for example, at temperatures from about 0° C. to about 50° C. Reduction of intermediate bromine-containing products or hydrolysis to the oxindole of the formula V can then be carried out by treatment with a metal such as zinc or iron in acetic acid or a mixture of acetic acid and a solvent such as an alcohol like methanol, ethanol or tert-butanol or an ether like diethyl ether or THF, or by hydrogenation in the presence of a hydrogenation catalyst such as palladium hydroxide or palladium on carbon or Raney nickel, for example, in a solvent such as an alcohol like methanol or ethanol or an ester like ethyl acetate at temperatures from about 0° C. to about 60° C. and a hydrogen pressure from about 1 bar to about 100 bar, as described in J. Parrick et al., Tetrahedron Lett. 25 (1984), 3099; A. Marfat et al., Tetrahedron Lett. 28 (1987), 4027; or R. P. Robinson et al., J. Org. Chem. 56 (1991), 4805, for example.

Compounds of the formula V can also be obtained by reacting an oxindole of the formula VI, wherein the group $R^{40}$ and the number n are defined as in the compound of the formula I and additionally functional groups can be present in protected form or in the form of a precursor group which is later converted into the final group, with a compound of the formula III as defined above, wherein $X^1$ is halogen or an arylsulfonyloxy or alkylsulfonyloxy group or a boron-containing group such as a boronic acid group or the group $BF_3^-$ having a cation like a potassium cation as counterion, in a nucleophilic substitution reaction or an Ullmann reaction or another transition metal-catalyzed reaction as outlined afore. The explanations given above with respect to the reaction of the compounds of the formulae II and III, for example regarding palladium-catalyzed and copper-catalyzed reactions, apply correspondingly with respect to the reaction of the compounds of the formulae VI and III.

In the course of the synthesis of the compounds of the formula I, the oxindoles of the formula V can then be subjected to a Vilsmeier formylation with concomitant chlorination to give the 1-$R^{30}$-2-chloro-indole-3-carboxaldehydes of the formula VII,

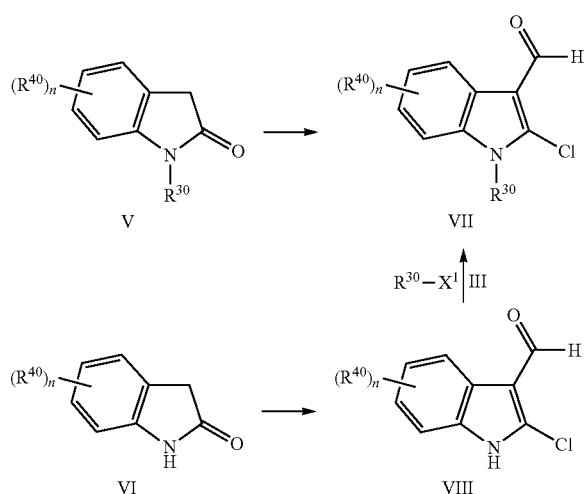

wherein the groups $R^{30}$ and $R^{40}$ and the number n are defined as in the compound of the formula I and additionally functional groups can be present in protected form or in the form of a precursor group which is later converted into the final group. The Vilsmeier formylation reagent can conveniently be prepared in situ from dimethylformamide and a suitable inorganic or organic chloride such as phosgene, oxalyl chloride or phosphorus oxychloride in an inert aprotic solvent such as a hydrocarbon or chlorinated hydrocarbon like benzene, dichloromethane or chloroform, an ether like DME or an excess of DMF, or a mixture thereof, at temperatures from about 0° C. to about 10° C. Preferably, phosphorus oxychloride is employed. The reaction of the Vilsmeier reagent with the compound of the formula V is usually carried out at temperatures from about 0° C. to about 30° C., preferably in the presence of a base such as pyridine. Hydrolytic workup of the reaction mixture, which like the workup of all reactions in the preparation of the compounds of the formula I can generally be performed under standard conditions, then yields the aldehyde of the formula VII.

Compounds of the formula VII can also be obtained by first subjecting an oxindole of the formula VI to a Vilsmeier formylation with concomitant chlorination in the 2-position analogously as outlined afore to give the 2-chloro-indole-3-carboxaldehydes of the formula VIII, wherein the group $R^{40}$ and the number n are defined as in the compound of the formula I and additionally functional groups can be present in protected form or in the form of a precursor group which is later converted into the final group, and then introducing the group $R^{30}$ in the 1-position of the indole ring in the compound of the formula VIII by reaction with a compound of the formula III as defined above, wherein $X^1$ is halogen or an arylsulfonyloxy or alkylsulfonyloxy group or a boron-containing group such as a boronic acid group or the group $BF_3^-$ having a cation like a potassium cation as counterion, in a nucleophilic substitution reaction or an Ullmann reaction or another transition metal-catalyzed reaction as outlined afore. The explanations given above with respect to the reaction of the compounds of the formulae II and III, for example regarding palladium-catalyzed and copper-catalyzed reactions, apply correspondingly with respect to the reaction of the compounds of the formulae VIII and III.

The indole-3-carboxaldehydes of the formula VII can then be oxidized under standard conditions for the oxidation of aldehydes to carboxylic acids to give the indole-3-carboxylic acids of the formula IX, wherein the groups $R^{30}$ and $R^{40}$ and the number n are defined as in the compound of the formula I and additionally functional groups can be present in protected form or in the form of a precursor group which is later converted into the final group. For example, the oxidation can be performed with a permanganate such as potassium permanganate in a mixture of water and an inert organic solvent, such as a ketone like acetone or an ether like THF, at temperatures from about 10° C. to about 30° C., for example at room temperature, at about neutral pH values. Conveniently, the oxidation can also be accomplished with a chlorite such as sodium chlorite in the presence of 2-methylbut-2-ene in mixture of water and an inert organic solvent, such as an alcohol like tert-butanol or an ether like THF, at temperatures from about 10° C. to about 30° C., for example at room temperature, at weakly acidic pH values, for example in the presence of a dihydrogenphosphate.

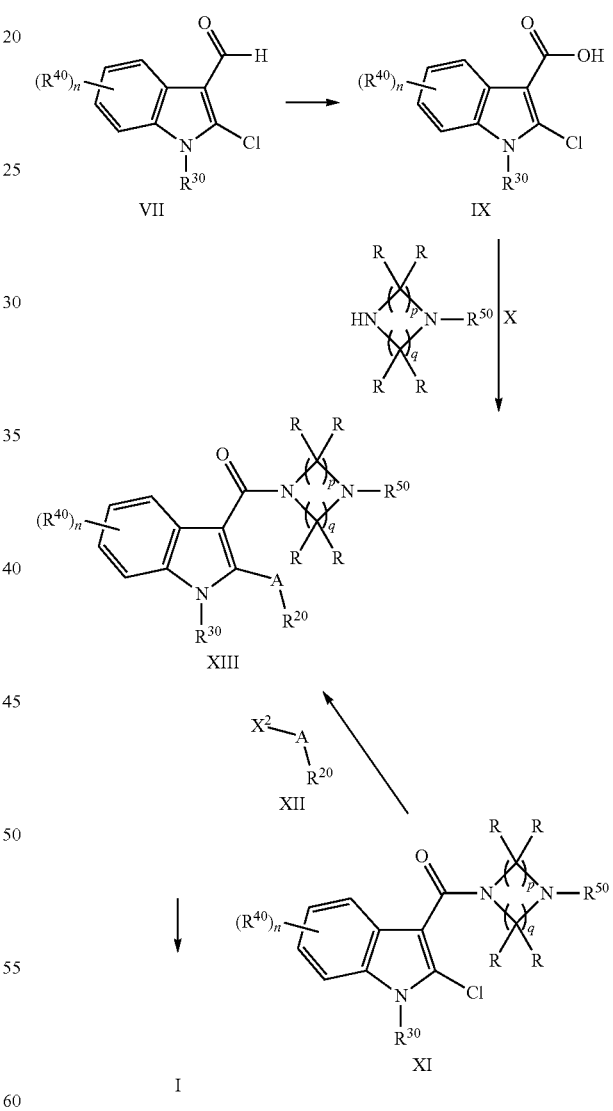

The carboxylic acid of the formula IX can then be coupled under standard conditions for the formation of an amide bond with a diazacycloalkane of the formula X to give a compound of the formula XI. The groups R, $R^{30}$ and $R^{40}$ and the numbers n, p and q in the compounds of the formulae X and XI are defined as in the compounds of the formula I and additionally functional groups can be present in protected form or in the form of a precursor group which is later converted into the final group. The compounds of the formula VII are defined as above. The group $R^{50}$ in the compounds of the formulae X and XI can have the meanings of the group $R^{10}$ in the compounds of the formula I with the exception of hydrogen, i.e. it can be $(C_1-C_6)$-alkyl-O—CO— or $(C_3-C_7)$-cycloalkyl-$C_vH_{2v}$—O—CO—, which groups protect the nitrogen atom carrying $R^{50}$ against a reaction with the compound of the formula IX, or $R^{50}$ can be another protective group which prevents a reaction at the said nitrogen atom and can later be removed to give a final compound of the formula I in which $R^{10}$ is hydrogen. Examples of groups which prevent a reaction at the said nitrogen atom, are the benzyloxycarbonyl group which can later be cleaved by hydrogenation in the presence of a catalyst such as a palladium catalyst, the tert-butyloxycarbonyl group which can later be cleaved by treatment with an acid such as trifluoroacetic acid or hydrogen chloride, or the fluoren-9-yloxycarbonyl group which can later be cleaved by treatment with piperidine. For the formation of the amide bond, the carboxylic acid of the formula IX is usually converted into a reactive derivative, which can be isolated or prepared in situ, or activated in situ by a customary amide coupling reagent. For example, the compound of the formula IX can be converted into an acid chloride by treatment with thionyl chloride, oxalyl chloride or (1-chloro-2-methyl-propenyl)-dimethylamine, into a reactive ester, or into a mixed anhydride by treatment with an alkyl chloroformate like ethyl chloroformate or isobutyl chloroformate, or it can be activated with a reagent such as propanephosphonic anhydride, an N,N'-carbonyldiazole like N,N'-carbonyldiimidazole (CD), a carbodiimide like N,N'-diisopropylcarbodiimide (DIC), N,N'-dicyclohexylcarbodiimide (DCC) or N-ethyl-N'-(3-dimethylaminopropyl)carbodiimide hydrochloride (EDC), a carbodiimide together with an additive like 1-hydroxybenzotriazole (HOBT) or 1-hydroxy-7-azabenzotriazole (HOAT), a uronium-based coupling reagent like O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU) or O-(cyano(ethoxycarbonyl)methyleneamino)-N,N,N',N'-tetramethyluronium tetrafluoroborate (TOTU), or a phosphonium-based coupling reagent like (benzotriazol-1-yloxy)tris(dimethylamino)phosphonium hexafluorophosphate (BOP), (benzotriazol-1-yloxy)tripyrrolidinophosphonium hexafluorophosphate (PyBOP) or bromotripyrrolidinophosphonium hexafluorophosphate (PyBroP). The activation of the compound of the formula IX and the reaction of the activated compound of the formula IX or a reactive derivative of the compound of the formula IX with the compound of the formula X is generally carried out in an inert solvent, such as an ether like THF, dioxane or DME, a hydrocarbon such as toluene, a chlorinated hydrocarbon like dichloromethane or chloroform, or an amide such as DMF or NMP, for example, or a mixture of solvents, at temperatures from about 0° C. to about 60° C. in the presence of a suitable base such a tertiary amine like triethylamine, ethyldiisopropylamine, N-methylmorpholine or pyridine, or a basic alkali metal compound such as an alkali metal carbonate like sodium carbonate, potassium carbonate or cesium carbonate, for example.

The obtained compound of the formula XI can then be reacted with a compound of the formula XII to give a compound of the formula XIII. The groups A, R, $R^{20}$, $R^{30}$ and $R^{40}$ and the numbers n, p and q in the compounds of the formulae XII and XIII are defined as in the compounds of the formula I and additionally functional groups can be present in protected form or in the form of a precursor group which is later converted into the final group. The group $R^{50}$ in the compound of the formula XIII is defined as in the compounds of the formulae X and XI. In case the group A in the compound of the formula XII is O, S or $N((C_1-C_4)$-alkyl), the group $X^2$ is hydrogen, and the reaction of the compounds of the formulae XI and XII is a nucleophilic substitution reaction. In such case, as applies in general to all starting compounds and intermediates in the synthesis of the compounds of the formula I including the compounds of the formulae IX, X and XII, for example, the said compounds of the formula XII in which $X^2$ is hydrogen can also be employed in the form of a salt. Likewise, all products obtained in the course of the synthesis of the compounds of the formula I, including the final compounds of the formula I, can be obtained in the form of a salt. Examples of suitable salts of the compounds of the formula XII, which can also be prepared in situ, are alkaline metal salts such as sodium salts and potassium salts and salts comprising an inert ammonium cation such as quaternary ammonium salts. The reaction of a compound of the formula XII, wherein A is O, S or $N((C_1-C_4)$-alkyl) and $X^2$ is hydrogen, with a compound of the formula XI is usually carried out in a solvent, for example an inert aprotic solvent such as an amide like DMF or NMP, or DMSO, or a mixture of solvents, in the presence of a base such as an alcoholate like sodium ethoxide or potassium tert-butoxide, a hydride like sodium hydride or potassium hydride, or an amide like sodium amide or lithium diisopropylamide, at elevated temperatures from about 80° C. to about 180° C. Advantageously, the reaction can be carried out in a microwave reactor. In case the group A in the compound of the formula XII is $C(R^a)_2$, the reaction of the compounds of the formulae XI and XII to give the compound of the formula XIII is favorably carried out via an organometallic compound. For example, in such case the compound of the formula XII can be an organometallic compound such as an organozinc compound like an organozinc chloride or organozinc bromide, the group $X^2$ in the compound of the formula XII then being the group Zn—Cl or Zn—Br, or an organoboron compound like a 9-organo-9-borabicyclo[3.3.1]nonane, the group $X^2$ in the compound of the formula XII then being a 9-borabicyclo[3.3.1]nonan-9-yl group. With respect to the compound of the formula XII which is actually employed in the reaction in case A is $C(R^a)_2$, the group $X^2$ in the compound of the formula XII can also be regarded to be halogen such as chlorine or bromine, and this compound of the formula XII is then converted in situ by treatment with zinc into the respective organozinc compound or into an organoboron compound. The reaction of an organozinc compound of the formula XII with the compound of the formula XI is generally carried out in an inert aprotic solvent such as a hydrocarbon like hexane, benzene or toluene, an ether like THF or dioxane, or an amide like DMF or NMP, or a mixture of solvents, at temperatures from about 0° C. to about 120° C., favorably in the presence of a transition metal catalyst, such as in the presence of a palladium compound like palladium(II) acetate, tris(dibenzylideneacetone)dipalladium(0) or bis(dibenzylideneacetone)palladium(0) together with a phosphine ligand like 2-dicyclohexylphosphino-2',6'-dimethoxy-1,1'-biphenyl, for example, and additionally an alkoxyborane derivative like B-methoxy-9-borabicyclo[3.3.1]nonane, or in the presence of a nickel compound like nickel acetylacetonate. In the reaction of an organoboron compound of the formula XII with the compound of the formula XI generally a base such as tribasic potassium phosphate, for example, is added.

In another method for the preparation of a compound of the formula XIII from a compound of the formula XI and a compound of the formula XII wherein A is $C(R^a)_2$, the compound of the formula XI is first converted into the respective organolithium compound which comprises a lithium atom instead of the chlorine atom in the 2-position, for example by reaction with an alkyllithium compound such as n-butyllithium, and this intermediary organolithium compound is then reacted in a substitution reaction with a compound of the formula XII wherein the group $X^2$ is a nucleophilically substitutable leaving group such as halogen, in particular chlorine, bromine or iodine, or an arylsulfonyloxy or alkylsulfonyloxy group such as benzenesulfonyloxy, toluenesulfonyloxy, methanesulfonyloxy or trifluoromethanesulfonyloxy. The lithiation of the compound of the formula XI and subsequent alkylation are generally carried out in an inert aprotic solvent such as a hydrocarbon like hexane or benzene or an ether like THF or dioxane or a mixture of solvents at temperatures from about −80° C. to about 30° C.

In case the group $R^{50}$ in the compound of the formula XIII has any of the meanings of the group $R^{10}$ in the compounds of the formula I and all other groups have the desired meanings comprised by the definition of the compounds of the formula I, the compound of the formula XIII thus obtained is already a final compound of the formula I. In case $R^{50}$ is a protective group and a compound of the formula I is to be prepared in which $R^{10}$ is hydrogen, and/or any other groups are present in protected form or in the form of a precursor group, the compound of the formula XIII thus obtained can finally be converted into the desired compound of the formula I by removal of protection groups and/or conversion of any other groups. As indicated above, in order to avoid an undesired course of a reaction or side reactions, in any one or more steps in the synthesis of the compounds of the formula I functional groups can be present in protected form or in the form of a precursor group. Besides in the final step of the synthesis of a compound of the formula I, protective groups can be removed, and precursor groups be converted, also at other stages of the synthesis. Respective synthetic strategies and details about suitable protective groups and their introduction and removal are well known to a person skilled in the art and are found in P. G. M. Wuts and T. W. Greene, Greene's Protective Groups in Organic Synthesis, 4. ed. (2007), John Wiley & Sons, for example. Examples of protective groups which may be mentioned, are benzyl protective groups such as in benzyl ethers of hydroxy groups and benzyl esters of carboxylic acid groups from which the benzyl group can be removed by catalytic hydrogenation in the presence of a palladium catalyst, tert-butyl protective groups such as in tert-butyl esters of carboxylic acid groups from which the tert-butyl group can be removed by treatment with trifluoroacetic acid, acyl protective groups which protect hydroxy groups and amino groups in the form of esters and amides and which can be cleaved by acidic or basic hydrolysis, and alkyloxycarbonyl protective groups such as in tert-butoxycarbonyl derivatives of amino groups, including the cyclic amino group being part of the diazacycloalkane moiety depicted in formula I in case $R^{10}$ is hydrogen, which can be cleaved by treatment with trifluoroacetic acid. Examples of precursor groups which may be mentioned are nitro groups which can be converted to amino groups by catalytic hydrogenation or by reduction with sodium dithionite, for example, and cyano groups which can be converted to carboxamide groups and carboxylic acid groups by hydrolysis.

In addition, in order to obtain further compounds of the formula I, various other transformations of functional group can be carried out in compounds of the formula I or compounds of the formula XIII or other compounds occurring in the synthesis of the compounds of the formula I. For example, a hydroxy group in a compound of the formula I or XIII can be etherified or esterified or reacted with an isocyanate to give a carbamate under standard conditions. Etherifications of hydroxy groups can favorably be performed by alkylation with the respective halogen compound, in particular a bromide or iodide, in the presence of a base such an alkali metal carbonate like potassium carbonate or cesium carbonate in an inert solvent such as an amide like DMF or NMP or a ketone like acetone or butan-2-one, or with the respective alcohol under the conditions of the Mitsunobu reaction in the presence of an azodicarboxylate like diethyl azodicarboxylate or diisopropyl azodicarboxylate and a phosphine like triphenylphosphine or tributylphosphine in an inert aprotic solvent such as an ether like THF or dioxane (cf. O. Mitsunobu, Synthesis (1981), 1). An amino group in a compound of the formula I or XIII can be modified under standard conditions for alkylation, for example by reaction with a halogen compound or by reductive amination of a carbonyl compound, or for acylation or sulfonylation, for example by reaction with an activated carboxylic acid or a carboxylic acid derivate like an acid chloride or anhydride or a sulfonic acid chloride. A carboxylic acid group in a compound of the formula I or XIII can be activated or converted into a reactive derivative as outlined above with respect to the compounds of the formula IX and reacted with an alcohol or amine to give an ester or amide. An alkyl-S— group in a compound of the formula I or XIII can be oxidized with a peroxide like hydrogen peroxide or a peracid to give an alkyl-S(O)— or alkyl-$S(O)_2$— group, and a protected mercapto group in a compound of the formula XIII can be deprotected and oxidized to give a sulfonic acid which can then be activated and reacted with an amine under standard conditions to give a sulfonamide.

The order in which groups are introduced in the course of the synthesis of a compound of the formula I, can also be different from the ones outlined above. For example, instead of first introducing the diazacycloalkane moiety and then the moiety -A-$R^{20}$ by reacting a compound of the formula IX with a compound of the formula X and reacting the obtained compound of the formula XI with a compound of the formula XII, it is also possible to introduce first the moiety -A-$R^{20}$ and then the diazacycloalkane moiety by reacting a compound of the formula IX or a protected form thereof such as an ester with a compound of the formula XII and, optionally after deprotection, reacting the obtained compound of the formula XIV with a compound of the formula X to give a compound of the formula XIII which can finally be converted into the desired compound of the formula I, for example by removing the protective group $R^{50}$ in the case of the preparation of a compound of the formula I in which $R^{10}$ in the compound of the formula I is hydrogen.

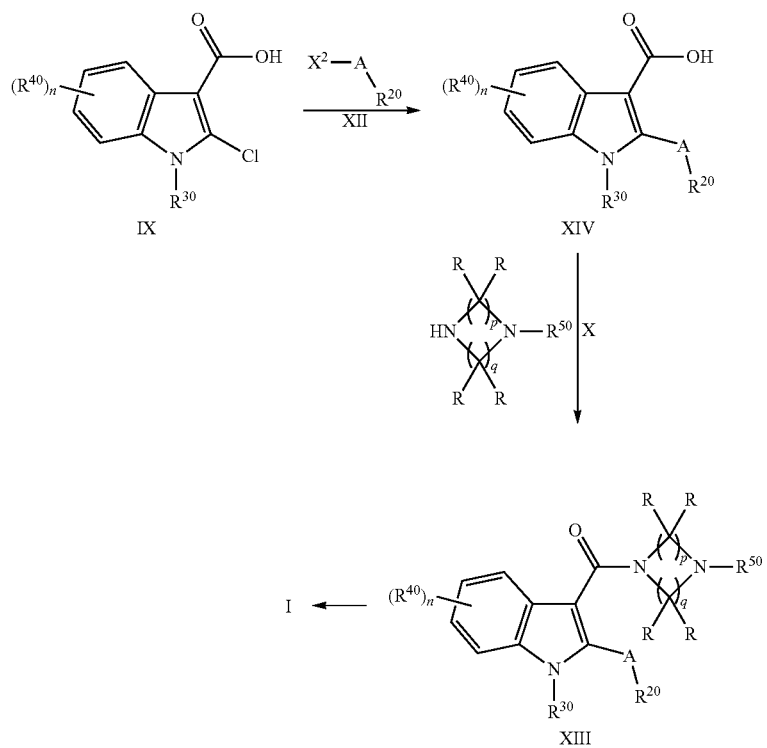

The groups A, $R^{20}$, $R^{30}$ and $R^{40}$ and the number n in the compounds of the formula XIV are defined as in the compounds of the formula I and additionally functional groups can be present in protected form or in the form of a precursor group which are later converted into the final group. Besides that, as mentioned, in the employed compounds of the formula IX the carboxylic acid depicted in the formula can be present in protected form, for example in the form of an ester like a tert-butyl ester or a benzyl ester, when reacting the compounds of the formulae IX and XII, and the carboxylic acid group in the compound of the formula XIV can thus also be present in protected form and is deprotected before reacting the compounds of the formulae X and XIV. The compounds of the formulae IX, X, XII and XIII are defined as above. All explanations given above with respect to the reaction of the compounds of the formula XI with the compounds of the formula XII, and the reaction of the compounds of the formula IX with the compounds of the formula X, apply correspondingly to the reaction of the compounds of the formula IX with the compounds of the formula XII, and the reaction of the compounds of the formula X with the compounds of the formula XIV, respectively. Thus, for example, for the formation of the amide bond in the reaction of the compounds of the formulae X and XIV the carboxylic acid group is generally converted into a reactive derivative or activated by means of a customary amide coupling reagent and reacted with the compound of the formula X in the presence of a base as outlined above.

In a further strategy for the synthesis of the compounds of the formula I, the moiety -A-$R^{20}$ can be also introduced into an aldehyde of the formula VII by reacting it with a compound of the formula XII to give a compound of the formula XV, the aldehyde group in the compound of the formula XV then be oxidized to give a compound of the formula XIV, and the latter compound then reacted with a compound of the formula X to finally give a compound of the formula I as already outlined above.

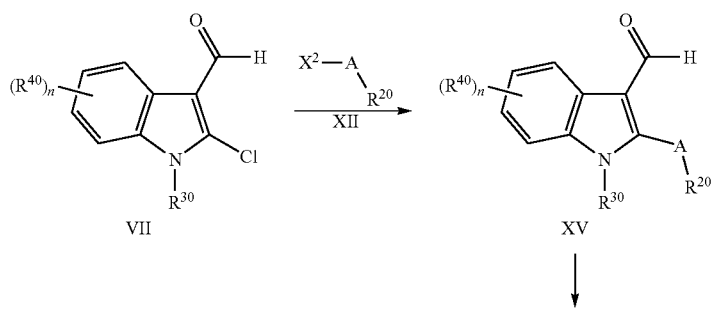

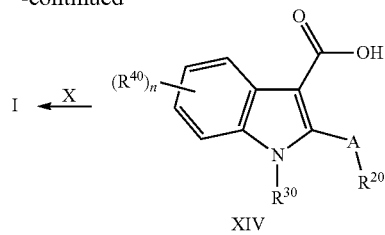

XIV

The groups A, $R^{20}$, $R^{30}$ and $R^{40}$ and the number n in the compounds of the formula XV are defined as in the compounds of the formula I and additionally functional groups can be present in protected form or in the form of a precursor group which are later converted into the final group. The compounds of the formulae VII, X, XII and XIV are defined as above. All explanations given above with respect to the reaction of the compounds of the formula XI or the formula IX with the compounds of the formula XII, and with respect to the oxidation of the compounds of the formula VII to the compounds of the formula IX, apply correspondingly to the reaction of the compounds of the formula VII with the compounds of the formula XII and the oxidation of the compounds of the formula XV to the compounds of the formula XIV, respectively. Thus, for example, the oxidation of the aldehyde group in the compounds of the formula XIV can conveniently be performed with sodium chlorite in the presence of 2-methylbut-2-ene or with potassium permanganate in a mixture of water and an organic solvent as outlined above.

All reactions carried out in the preparation of the compounds of the formula I are known per se and can be carried out in manner familiar to a person skilled in the art by or analogously to procedures which are described in the standard literature, for example in Houben-Weyl, Methods of Organic Chemistry, Thieme; or Organic Reactions, John Wiley & Sons; or R. C. Larock, Comprehensive Organic Transformations: A Guide to Functional Group Preparations, 2. ed. (1999), John Wiley & Sons, and the references quoted therein.

The starting compounds and building blocks for the synthesis of the compounds of the formula I are commercially available or can be prepared according to procedures described in the literature or analogously to such procedures. If desired, indoles of the formula II can be prepared according to the procedures of the well-known Fischer indole synthesis, in which an optionally substituted phenylhydrazone is cyclized, or the Bischler indole synthesis, in which an optionally substituted 2-anilinoketone is cyclized, for example, and oxindoles of the formula VI can be prepared by cyclizing optionally substituted 2-chloro-acetanilides. In order to prepare specifically substituted indoles of the formula II, it is furthermore possible to reduce a 1H-indole to a 2,3-dihydro-1H-indole, for example by hydrogenation, subject the latter compound to a electrophilic aromatic substitution reaction which allows the introduction of substituents into the benzene ring which cannot be introduced by subjecting the indole to such a reaction, and subsequently dehydrogenating the 2,3-dihydro-1H-indole to give an indole again, for example by means of chloranil, manganese dioxide or palladium together with a hydrogen acceptor. As examples of articles in which syntheses and reactions of indoles are described, G. R. Humphrey et al., Chem. Rev. 106 (2006), 2875; and R. J. Sundberg, Indoles (Best Synthetic Methods), Academic Press, London, San Diego (1996), may be mentioned. As another example of procedures for the preparation of starting compounds and building blocks, the processes for the preparation of substituted phenols described in US 2006/0160786 and in Organikum, 12. ed., VEB Deutscher Verlag der Wissenschaften, Berlin (1973), 588, may be mentioned, according to which compounds of the formula XII in which $X^2$ is hydrogen, A is O and $R^{20}$ is substituted phenyl, can be prepared, such as 3-fluoro-2-methyl-phenol, 2-fluoro-6-methyl-phenol or 3,5-difluoro-2-methyl-phenol, for example.

Another subject of the present invention are the novel starting compounds and intermediates occurring in the synthesis of the compounds of the formula I, including the compounds of the formulae II, III, IV, V, VI, VII, VIII, IX, X, XI, XII, XIII, XIV and XV, wherein A, R, $R^{20}$, $R^{30}$, $R^{40}$, $R^{50}$, $X^1$, $X^2$, n, p and q are defined as above, in any of their stereoisomeric forms or a mixture of stereoisomeric forms in any ratio, and their salts, and solvates of any of them, and their use as intermediates. The general explanations, preferred definitions of groups and numbers and embodiments of the invention given above with respect to the compounds of the formula I apply correspondingly to the said intermediates and starting compounds. A subject of the invention are in particular the novel specific starting compounds and intermediates disclosed herein. Independently thereof whether they are disclosed as a free compound and/or as a specific salt, they are a subject of the invention both in the form of the free compounds and in the form of their salts, and if a specific salt is disclosed, additionally in the form of this specific salt, and in the form of solvates of any of them.

The compounds of the formula I inhibit the enzyme renin as can be demonstrated in the pharmacological tests described below and in other pharmacological tests which are known to a person skilled in the art, for example in in vitro tests in which the inhibition of human renin is determined, or in animal models in which the antihypertensive activity and other effects are determined in vivo. The compounds of the formula I are suitable for the treatment of hypertension including pulmonary hypertension, for example, and other disorders of the cardiovascular system and heart diseases, such as heart failure, cardiac infarction, angina pectoris, cardiac insufficiency, cardiac failure, cardiac hypertrophy, cardiac fibrosis, vascular hypertrophy, left ventricular dysfunction, in particular left ventricular dysfunction after myocardial infarction, endothelial dysfunction, ischemic and obstructive peripheral circulation disorders and restenosis including restenosis post-angioplasty, for example, for the treatment of renal diseases such as renal fibrosis, renal ischemia, renal failure and kidney insufficiency, for example, and for the treatment of other diseases, for example diabetes complications, such as nephropathy and retinopathy, cerebral afflictions, such as cerebral hemorrhage, glaucoma, and end-organ damage. The treatment of diseases is to be understood as meaning both the therapy of existing pathological changes or malfunctions of the organism or of existing symptoms with the aim of relief, alleviation or cure, and the prophylaxis or prevention of pathological changes or malfunctions of the organism or of symptoms in humans or animals which are susceptible thereto and are in need of such a prophylaxis or prevention, with the aim of prevention or suppression of their occurrence or of an attenuation in the case of their occurrence. For example, in patients who on account of their disease history are susceptible to ventricular dysfunction after myocardial infarction, by means of the prophylactic or preventive medicinal treatment the occurrence of ventricular dysfunction can be prevented or its extent and sequelae decreased. The treatment of diseases can occur both in acute cases and in chronic cases.

The compounds of the formula I and their physiologically acceptable salts and physiologically acceptable solvates thereof can therefore be used in animals, in particular in mammals and specifically in humans, as a pharmaceutical or medicament on their own, in mixtures with one another or in the form of pharmaceutical compositions. A subject of the present invention also are the compounds of the formula I and their physiologically acceptable salts and physiologically acceptable solvates thereof for use as a pharmaceutical, as well as pharmaceutical compositions and medicaments which comprise an efficacious dose of at least one compound of the formula I and/or a physiologically acceptable salt thereof and/or a physiologically acceptable solvate of any of them as an active ingredient and a pharmaceutically acceptable carrier, i.e. one or more pharmaceutically innocuous vehicles and/or excipients. A subject of the present invention furthermore are the compounds of the formula I and their physiologically acceptable salts and physiologically acceptable solvates thereof for use in the treatment of the diseases mentioned above or below, for example of hypertension, or for the inhibition of renin, as well as the use of the compounds of the formula I and their physiologically acceptable salts and physiologically acceptable solvates thereof for the manufacture of a medicament for the treatment of the diseases mentioned above or below, for example of hypertension, or for the manufacture of a medicament for the inhibition of renin, wherein the treatment of diseases comprises their therapy and prophylaxis. A subject of the invention also are methods for the treatment of the diseases mentioned above or below, which comprise administering an efficacious amount of at least one compound of the formula I or a physiologically acceptable salt thereof or a physiologically acceptable solvate of any of them to a human or an animal which is in need thereof. The compounds of the formula I and pharmaceutical composition and medicaments comprising them can be administered enterally, for example by oral, buccal, sublingual or rectal administration, parenterally, for example by intravenous, intramuscular or subcutaneous injection or infusion, or by another type of administration such as topical, percutaneous, transdermal, intratracheal, intranasal or intraocular administration.

The pharmaceutical compositions and medicaments according to the invention normally contain about 0.5 to about 90 percent by weight of compounds of the formula I and/or their physiologically acceptable salts and/or physiologically acceptable solvates thereof. The amount of active ingredient of the formula I and/or its physiologically acceptable salt and/or a physiologically acceptable solvate of any of them in the pharmaceutical compositions and medicaments is in general about 0.2 mg to about 1000 mg, preferably about 0.2 mg to about 500 mg, particularly preferably about 1 mg to about 300 mg, per unit dose. The production of the pharmaceutical compositions and medicaments can be carried out in a manner known per se. For this, the compounds of the formula I and/or their physiologically acceptable salts and/or physiologically acceptable solvates thereof are mixed together with one or more solid or liquid vehicles and/or excipients, if desired also in combination with one or more other active ingredients such as, for example, an angiotensin converting enzyme inhibitor, an angiotensin receptor antagonist, a diuretic, an endothelin receptor antagonist, an endothelin converting enzyme inhibitor, a neutral endopeptidase inhibitor, a calcium channel blocker, a nitrate like isosorbiddinitrate, a β-receptor blocker, an α1 adrenoreceptor antagonist, a cannabinoid receptor antagonist, a potassium channel modulator, a thromboxane synthetase inhibitor, an anti-serotoninergic agent, or another agent useful for treating hypertension, heart failure, vascular diseases related to diabetes or renal diseases such as acute or chronic renal failure, for example, and are brought into a suitable form for dosage and administration which can then be used in human medicine or veterinary medicine. A subject of the present invention also is in particular a pharmaceutical composition which comprises an efficacious dose of at least one compound of the formula I and/or a physiologically acceptable salt thereof and/or a physiologically acceptable solvate of any of them and one or more other active ingredients and a pharmaceutically acceptable carrier, wherein the other active ingredients are useful for the treatment of hypertension, cardiac infarction, heart failure, vascular diseases related to diabetes, end-organ damage such as cardiac insufficiency or kidney insufficiency, renal diseases such as acute or chronic renal failure, restenosis or glaucoma, and wherein as examples of such other active ingredients angiotensin converting enzyme inhibitors, angiotensin receptor antagonists, diuretics, endothelin receptor antagonists, endothelin converting enzyme inhibitors, neutral endopeptidase inhibitors, calcium channel blockers, nitrates like isosorbiddinitrate, β-receptor blockers, α1 adrenoreceptor antagonists, cannabinoid receptor antagonists, potassium channel modulators, thromboxane synthetase inhibitors and anti-serotoninergic agents may be mentioned.

As vehicles and excipients, suitable organic and inorganic substances can be used which do not react in an undesired manner with the compounds of the formula I. Examples which may be mentioned are water, vegetable oils, waxes, alcohols such as ethanol, isopropanol, 1,2-propanediol, benzyl alcohols or glycerol, polyols, polyethylene glycols, polypropylene glycols, glycerol triacetate, gelatin, carbohydrates such as lactose or starch, stearic acid and its salts such as magnesium stearate, talc, lanolin, petroleum jelly, or mixtures thereof, for example mixtures of water with one or more organic solvents such as mixtures of water with alcohols. For oral and rectal use, in particular pharmaceutical forms such as, for example, tablets, film-coated tablets, sugar-coated tablets, granules, hard and soft gelatin capsules, suppositories, solutions, preferably oily, alcoholic or aqueous solutions, syrups, juices or drops, furthermore suspensions or emulsions, can be used. For parenteral use, for example by injection or infusion, in particular pharmaceutical forms such as solutions, preferably aqueous solutions, can be used. For topical use, in particular pharmaceutical forms such as ointments, creams, pastes, lotions, gels, sprays, foams, aerosols, solutions or powders can be used. Further suitable pharmaceutical forms are, for example, implants and patches. and forms adapted to inhalation. The compounds of the formula I and their physiologically acceptable salts and physiologically acceptable solvates of any of them can also be lyophilized and the obtained lyophilizates obtained used, for example, for the production of injectable compositions. In particular for topical application, liposomal compositions are also suitable. As examples of types of excipients or additives which can be contained in the pharmaceutical compositions and medicaments, lubricants, preservatives, thickeners, stabilizers, disintegrants, wetting agents, agents for achieving a depot effect, emulsifiers, salts, for example for influencing the osmotic pressure, buffer substances, colorants and flavoring substances may be mentioned. The pharmaceutical compositions and medicaments can also contain one or more other active ingredients and/or, for example, one or more vitamins.

As usual, the dosage of the compounds of the formula I depends on the circumstances of the specific case and is adjusted by the physician according to the customary rules and procedures. It depends, for example, on the compound of the formula I administered and its potency and duration of action, on the nature and severity of the individual syndrome, on the sex, age, weight and the individual responsiveness of the human or animal to be treated, on whether the treatment is acute or chronic or prophylactic, or on whether further pharmaceutical active compounds are administered in addition to compound of the formula I. Normally, in the case of administration to an adult weighing about 75 kg, a dose of from about 0.1 mg to about 100 mg per kg per day, preferably from about 1 mg to about 10 mg per kg per day (in each case in mg per kg of body weight), is sufficient. The daily dose can be administered in the form of a single dose or divided into a number of individual doses, for example two, three or four individual doses. The administration can also be carried out continuously, for example by continuous injection or infusion. Depending on the circumstances of the specific case, it may be necessary to deviate upward or downward from the indicated dosages.

Besides as a pharmaceutical active compound in human medicine and veterinary medicine, the compounds of the formula I can also be employed as an aid in biochemical investigations or as a scientific tool or for diagnostic purposes, for example in in vitro diagnoses of biological samples, if an inhibition of renin is intended. The compounds of the formula I and their salts can also be used as intermediates, for example for the preparation of further pharmaceutical active substances.

The following examples illustrate the invention.
Abbreviations:
ACN acetonitrile
B-OM-9-BBN B-methoxy-9-borabicyclo[3.3.1]nonane
DCM dichloromethane
DMF dimethylformamide
DMSO dimethyl sulfoxide
EA ethyl acetate
EDC N-ethyl-N'-(3-dimethylaminopropyl)carbodiimide hydrochloride
HEP n-heptane
HOAT 1-hydroxy-7-azabenzotriazole
MOH methanol
NMM N-methyl-morpholine
NMP N-methyl-pyrrolidin-2-one
S-PHOS 2-dicyclohexylphosphino-2',6'-dimethoxy-1,1'-biphenyl
TFA trifluoroacetic acid
THF tetrahydrofuran When compounds containing a basic group were purified by preparative high pressure liquid chromatography (HPLC) on reversed phase (RP) column material and, as customary, the eluent was a gradient mixture of water and acetonitrile containing trifluoroacetic acid, they were in general obtained in the form of an acid addition salt with trifluoroacetic acid, depending on the details of the workup such as the lyophilization conditions. Such contained trifluoroacetic acid, whose amount can vary and can be up to about two equivalents of acid in the case of a compound containing two basic groups, for example, is not specified in the names in the headings of the examples and not depicted in the structural formulae, but indicated in the description of the examples. This applies accordingly to compounds which were obtained in the form of another acid addition salt such as an acid addition salt with hydrochloric acid, whose amount can likewise vary and can be up to about two equivalents of acid in the case of a compound containing two basic groups, for example, and which is not specified in the names in the headings of the examples and not depicted in the structural formulae, but indicated in the description of the examples. The particulars of the preparative HPLC method were as follows. Column: Waters Atlantis dC18 OBD, 30×100 mm, 5 µm. Flow: 60 ml/min. Eluent A: ACN. Eluent B: water+0.1% TFA. Gradient: from 10% A+90% B to 90% A+10% B within 10 min.

Characterization of the Compounds

The prepared compounds were in general characterized by spectroscopic data and chromatographic data, in particular mass spectra (MS) and HPLC retention times (Rt; in min) which were obtained by combined analytical HPLC/MS characterization (LC/MS), and/or nuclear magnetic resonance (NMR) spectra. Unless specified otherwise, $^1$H-NMR spectra were recorded at 500 MHz and in DMSO-D$_6$ as solvent. In the NMR characterization, the chemical shift δ (in ppm), the number of hydrogen atoms and the multiplicity (s: singlet, d: doublet, dd: double doublet, t: triplet, dt: double triplet, q: quartet, m: multiplet; br: broad) of the peaks are given. In the MS characterization, in general the mass number (m/z) of the peak of the molecular ion (M, e.g. M$^+$) or of a related ion such as the ion M+1 (e.g. M+1$^+$; protonated molecular ion M+H$^+$) or the ion M−17 (e.g. M−17$^+$; protonated molecular ion minus H$_2$O), which was formed depending on the ionization method used, is given. Generally, the ionization method was electrospray ionization (ESI). The particulars of the LC/MS methods used were as follows.

Method LC1

Column: YMC J'sphere H80, 33×2.1 mm, 4 µm; flow: 1.3 ml/min; eluent A: ACN+0.05% TFA; eluent B: water+0.05% TFA; gradient: from 5% A+95% B to 95% A+5% B within 2.5 min, then 95% A+5% B for 0.5 min; MS ionization method: ESI$^+$ Method LC2

Column: YMC J'sphere H80, 33×2.1 mm, 4 µm; flow: 1.0 ml/min; eluent A: ACN+0.05% TFA; eluent B: water+0.05% TFA; gradient: from 5% A+95% B to 95% A+5% B within 3.4 min, then 95% A+5% B for 1.0 min; MS ionization method: ESI$^+$ Method LC3

Column: YMC J'sphere H80, 33×2.1 mm, 4 µm; flow: 1.3 ml/min; eluent A: ACN+0.08% formic acid; eluent B: water+ 0.1% formic acid; gradient: from 5% A+95% B to 95% A+5% B within 2.5 min, then 95% A+5% B for 0.5 min; MS ionization method: ESI$^+$ Method LC4

Column: YMC J'sphere ODS H80, 20×2.1 mm, 4 µm; flow: 1.0 ml/min; eluent A: ACN; eluent B: water+0.05% TFA; gradient: from 4% A+96% B to 95% A+5% B within 2.0 min, then 95% A+5% B for 0.4 min, then to 96% A+4% B within 0.05 min; MS ionization method: ESI$^+$ Method LC5

Column: YMC J'sphere H80, 33×2.1 mm, 4 µm; flow: 1.3 ml/min; eluent A: ACN+0.05% TFA; eluent B: water+0.05% TFA; gradient: 5% A+95% B for 0.5 min, then to 95% A+5% B within 3.0 min, then 95% A+5% B for 0.5 min; MS ionization method: ESI$^+$ Method LC6

Column: YMC J'sphere H80, 33×2.1 mm, 4 µm; flow: 1.0 ml/min; eluent A: ACN+0.05% TFA; eluent B: water+0.05%

TFA; gradient: 2% A+98% B for 1 min, then to 95% A+5% B within 4 min, then 95% A+5% B for 1.25 min; MS ionization method: ESI+
Method LC7
Column: YMC Pack Pro C18 RS, 33×2.1 mm, 4 μm; flow: 1.0 ml/min; eluent A: ACN+0.1% TFA; eluent B: water+0.1% TFA; gradient: from 5% A+95% B to 95% A+5% B within 2.5 min, then 95% A+5% B for 0.5 min; MS ionization method: ESI+
Method LC8
Column: Waters XBridge C18, 33'2.1 mm, 4 μm; flow: 1.0 ml/min; eluent A: ACN+0.05% TFA; eluent B: water+0.05% TFA; gradient: 5% A+95% B for 0.3 min, then to 95% A+5% B within 3.2 min, then 95% A+5% B for 0.5 min; MS ionization method: ESI+
Method LC9
Column: Waters XBridge C18, 33×2.1 mm, 4 μm; flow: 1.0 ml/min; eluent A: ACN+0.1% TFA; eluent B: water+0.08% TFA; gradient: from 3% A+97% B to 60% A+40% B within 3.5 min, then to 98% A+2% B within 1.5 min; MS ionization method: ESI+

EXAMPLE 1

[2-(5-Fluoro-2-methyl-phenoxy)-1-phenyl-1H-indol-3-yl]-piperazin-1-yl-methanone

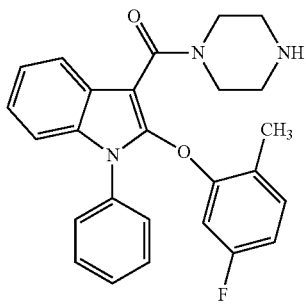

Step 1: 4-(2-Chloro-1-phenyl-1H-indole-3-carbonyl)-piperazine-1-carboxylic acid tert-butyl ester To a solution of 2-chloro-1-phenyl-1H-indole-3-carboxylic acid (cf. CA 1079739) (3.00 g, 11.0 mmol), tert-butyl 1-piperazinecarboxylate (2.06 g, 11.0 mmol), EDC (2.33 g, 12.1 mmol) and HOAT (1.73 g, 12.7 mmol) in DMF (12 ml) was added NMM (3.65 ml, 33.1 mmol), and the reaction mixture was stirred at room temperature overnight. The mixture was quenched with water and extracted with EA. The organic layer was separated, dried over sodium sulfate, filtered, and evaporated under reduced pressure. The residue was purified by silica gel chromatography (EA/HEP 1:3). 4.51 g of the title compound were obtained.
LC/MS (method LC4): m/z=440

Step 2: 4-[2-(5-Fluoro-2-methyl-phenoxy)-1-phenyl-1H-indole-3-carbonyl]-piperazine-1-carboxylic acid tert-butyl ester To a solution of 5-fluoro-2-methylphenol (43.0 mg, 341 μmol) in NMP (1.5 ml) was added sodium hydride (15.0 mg, 375 μmol; 60% dispersion in mineral oil), and the suspension was stirred at room temperature under an argon atmosphere for 20 min. After addition of 50.0 mg (114 μmol) of the compound of step 1, the reaction mixture was stirred for 2 h at 150° C. in a microwave reactor. The mixture was filtered and purified by preparative HPLC. The eluate was lyophilized overnight to give 23 mg of the title compound.
LC/MS (method LC4): m/z=530

Step 3: [2-(5-Fluoro-2-methyl-phenoxy)-1-phenyl-1H-indol-3-yl]-piperazin-1-yl-methanone A solution of the compound of step 2 (23 mg, 43.4 μmol) in DCM (8 ml) and TFA (2 ml) was stirred at room temperature for 1 h. The solvents were evaporated and the resulting solid dissolved in MOH and water and lyophilized overnight. The title compound was obtained in the form of the [2-(5-fluoro-2-methyl-phenoxy)-1-phenyl-1H-indol-3-yl]-piperazin-1-yl-methanone trifluoroacetic acid salt as a white solid. Yield: 21.0 mg.
LC/MS (method LC2): m/z=430.25, Rt=1.60 min
$^1$H-NMR: δ (ppm)=2.10 (s, 3H), 3.02 (br s, 4H), 3.68 (br s, 4H), 6.77-6.84 (m, 2H), 7.17-7.21 (m, 2H), 7.22-7.28 (m, 2H), 7.45-7.49 (m, 1H), 7.51-7.57 (m, 4H), 7.65-7.67 (m, 1H), 8.79 (br s, 2H)

EXAMPLE 2

[1-Phenyl-2-(2-methyl-phenoxy)-1H-indol-3-yl]-piperazin-1-yl-methanone

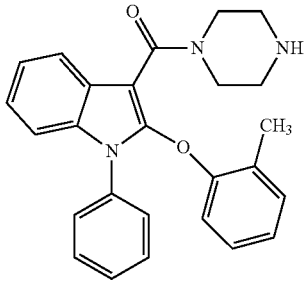

Step 1: 4-[1-Phenyl-2-(2-methyl-phenoxy)-1H-indole-3-carbonyl]-piperazine-1-carboxylic acid tert-butyl ester The title compound was prepared analogously as described in example 1, step 2, using 2-methylphenol. Yield: 40 mg.
LC/MS (method LC4): m/z=512

Step 2: [1-Phenyl-2-(2-methyl-phenoxy)-1H-indol-3-yl]-piperazin-1-yl-methanone

From the compound of step 1 (40.0 mg, 78.2 μmol), the title compound was prepared analogously as described in example 1, step 3, and obtained in the form of the [1-phenyl-2-(2-methyl-phenoxy)-1H-indol-3-yl]-piperazin-1-yl-methanone trifluoroacetic acid salt. Yield: 41.0 mg.
LC/MS (method LC1): m/z=411.19, Rt=1.40 min $^1$H-NMR: δ (ppm)=2.14 (s, 3H), 2.98 (br s, 4H), 3.65 (br s, 4H), 6.82 (d, 1H), 6.95 (t, 1H), 7.05 (t, 1H), 7.15 (d, 1H), 7.17-7.55 (m, 3H), 7.44-7.55 (m, 5H), 7.65 (d, 1H), 8.77 (br s, 2H)

EXAMPLE 3

[2-(Methyl-phenyl-amino)-1-phenyl-1H-indol-3-yl]-piperazin-1-yl-methanone

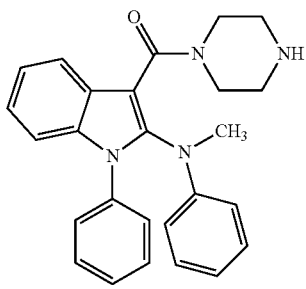

Step 1: 4-[2-(Methyl-phenyl-amino)-1-phenyl-1H-indole-3-carbonyl]-piperazine-1-carboxylic acid tert-butyl ester The title compound was prepared analogously as described in example 1, step 2, using N-methylaniline. Yield: 6 mg.
LC/MS (method LC4): m/z=511

Step 2: [2-(Methyl-phenyl-amino)-1-phenyl-1H-indol-3-yl]-piperazin-1-yl-methanone From the compound of step 1 (6 mg, 11.7 μmol), the title compound was prepared analogously as described in example 1, step 3, and obtained in the form of the [2-(methyl-phenyl-amino)-1-phenyl-1H-indol-3-yl]-piperazin-1-yl-methanone trifluoroacetic acid salt. Yield: 6 mg.
LC/MS (method LC1): m/z=410.21, Rt=1.40 min
$^1$H-NMR: δ (ppm)=2.95 (br s, 4H), 3.06 (s, 3H), 3.60 (br s, 4H), 6.70-6.74 (m, 3H), 7.11 (t, 2H), 7.17-7.19 (m, 1H), 7.21-7.25 (m, 2H), 7.41-7.45 (m, 3H), 7.51 (t, 2H), 7.61-7.63 (m, 1H), 8.75 (br s, 2H)

EXAMPLE 4

[2-(2-Chloro-phenylsulfanyl)-1-phenyl-1H-indol-3-yl]-piperazin-1-yl-methanone

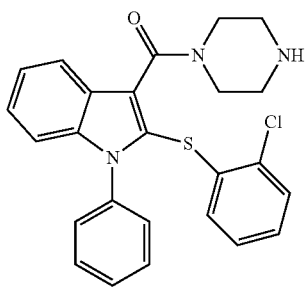

Step 1: 4-[2-(2-Chloro-phenylsulfanyl)-1-phenyl-1H-indole-3-carbonyl]-piperazine-1-carboxylic acid tert-butyl ester The title compound was prepared analogously as described in example 1, step 2, using 2-chlorothiophenol. Yield: 32 mg.
LC/MS (method LC4): m/z=549

Step 2: [2-(2-Chloro-phenylsulfanyl)-1-phenyl-1H-indol-3-yl]-piperazin-1-yl-methanone From the compound of step 1 (32.0 mg, 58.4 μmol), the title compound was prepared analogously as described in example 1, step 3, and obtained in the form of the [2-(2-chloro-phenylsulfanyl)-1-phenyl-1H-indol-3-yl]-piperazin-1-yl-methanone trifluoroacetic acid salt. Yield: 30 mg.
LC/MS (method LC1): m/z=447.12, Rt=1.48 min
$^1$H-NMR: δ (ppm)=3.04 (br s, 2H), 3.18 (br s, 2H), 3.64 (br s, 2H), 3.76 (br s, 2H), 6.77-6.80 (m, 1H), 7.12-7.16 (m, 3H), 7.27-7.37 (m, 5H), 7.46-7.50 (m, 3H), 7.73 (d, 1H), 8.80 (br d, 2H)

EXAMPLE 5

Perhydro-1,4-diazepin-1-yl-(2-phenoxy-1-phenyl-1H-indol-3-yl)-methanone

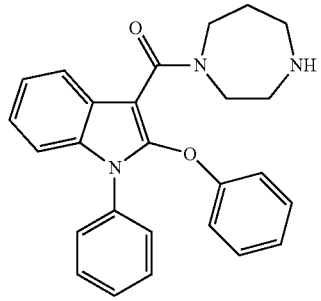

Step 1: 4-(2-Phenoxy-1-phenyl-1H-indole-3-carbonyl)-perhydro-1,4-diazepine-1-carboxylic acid tert-butyl ester To a solution of 2-phenoxy-1-phenyl-1H-indole-3-carboxylic acid (164 mg, 499 μmol; available by oxidation of 2-phenoxy-1-phenyl-1H-indole-3-carbaldehyde (DE 2707268) analogously as described in example 11, step 5), tert-butyl 1-homopiperazinecarboxylate (100 mg, 499 μmol), EDC (105 mg, 549 μmol) and HOAT (78.2 mg, 574 μmol) in DMF (2 ml) was added NMM (165 μl, 1.49 mmol) and the reaction mixture was stirred at room temperature overnight. The mixture was filtered and purified by preparative HPLC. The eluate was lyophilized overnight to give 169 mg of the title compound.
LC/MS (method LC4): m/z=512

Step 2: Perhydro-1,4-diazepin-1-yl-(2-phenoxy-1-phenyl-1H-indol-3-yl)-methanone From the compound of step 1 (169 mg, 330 μmol), the title compound was prepared analogously as described in example 1, step 3, and obtained in the form of the perhydro-1,4-diazepin-1-yl-(2-phenoxy-1-phenyl-1H-indol-3-yl)-methanone trifluoroacetic acid salt. Yield: 158 mg.
LC/MS (method LC3): m/z=411.19, Rt=1.51 min ¹H-NMR (400 MHz): δ (ppm)=1.92 (br s, 2H), 3.02 (br s, 2H), 3.11 (br s, 2H), 3.60 (br s, 4H), 6.96 (d, 2H), 7.05 (t, 1H), 7.17-7.28 (m, 5H), 7.43-7.56 (m, 5H), 7.64-7.67 (m, 1H), 8.68 (br s, 2H)

EXAMPLE 6

(2-Phenoxy-1-phenyl-1H-indol-3-yl)-piperazin-1-yl-methanone

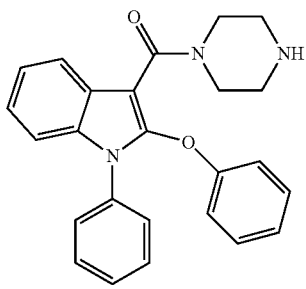

Step 1: 4-(2-Phenoxy-1-phenyl-1H-indole-3-carbonyl)-piperazine-1-carboxylic acid tert-butyl ester The title compound was prepared analogously as described in example 1, step 1, using 2-phenoxy-1-phenyl-1H-indole-3-carboxylic acid (500 mg, 1.52 mmol). Yield: 608 mg.
LC/MS (method LC4): m/z=498

Step 2: (2-Phenoxy-1-phenyl-1H-indol-3-yl)-piperazin-1-yl-methanone

From the compound of step 1 (48 mg, 96.4 μmol), the title compound was prepared analogously as described in example 1, step 3, and obtained in the form of the (2-phenoxy-1-phenyl-1H-indol-3-yl)-piperazin-1-yl-methanone trifluoroacetic acid salt. Yield: 39 mg.
LC/MS (method LC1): m/z=397.18, Rt=1.37 min
¹H-NMR: δ (ppm)=3.01 (s, 4H), 3.64 (s, 4H), 6.96 (d, 2H), 7.06 (t, 1H), 7.19-7.29 (m, 5H), 7.44-7.56 (m, 5H), 7.66-7.68 (m, 1H), 8.77 (br s, 2H)

EXAMPLE 7

[6-Hydroxy-1-phenyl-2-(2-methyl-phenoxy)-1H-indol-3-yl]-piperazin-1-yl-methanone

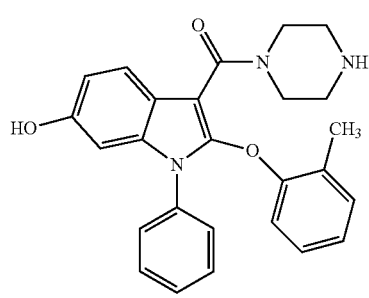

Step 1: 6-Methoxy-1-phenyl-1,3-dihydro-indol-2-one

To a mixture of 6-methoxy-1,3-dihydroindol-2-one (500 mg, 3.06 mmol), copper(I) iodide (58.3 mg, 306 μmol), N,N'-dimethylethylenediamine (65.3 μl, 613 μmol) and potassium carbonate (932 mg, 6.74 mmol) in ACN (6.5 ml) was added iodobenzene (411 μl, 3.68 mmol). The reaction mixture was stirred for 1 h at 120° C. in a microwave reactor. The mixture was quenched with water and extracted with EA. The organic layer was separated, dried over sodium sulfate, filtered and evaporated. The residue was purified by silica gel chromatography (EA/HEP 1:5). 550 mg of the title compound were obtained.
LC/MS (method LC4): m/z=240

Step 2: 2-Chloro-6-methoxy-1-phenyl-1H-indole-3-carbaldehyde

A solution of DMF (2.1 ml) and DCM (2.1 ml) was cooled to 0° C. and stirred under argon. Within 15 min phosphorus oxychloride (2.1 ml, 22.6 mmol) was added and the reaction mixture was stirred for 30 min at 0° C. The compound of step 1 (550 mg, 2.30 mmol), dissolved in chloroform (5.27 ml) and pyridine (1.05 ml), was then added to the cooled solution. The reaction mixture was stirred at room temperature overnight. The mixture was slowly poured into 300 ml of ice, and after a few minutes EA was added. The organic layer was separated, dried over sodium sulfate, filtered and evaporated under reduced pressure. Column chromatography on silica gel (EA/HEP 1:4) yielded 369 mg of the title compound as a white solid.
LC/MS (method LC4): m/z=286

Step 3: 2-Chloro-6-methoxy-1-phenyl-1H-indole-3-carboxylic acid

The compound of step 2 (365 mg, 1.27 mmol) was dissolved in tert-butanol (15 ml) and 2-methyl-2-butene (3 ml), and a solution of sodium chlorite (1.06 g, 11.7 mmol) and sodium dihydrogenphosphate (1.06 g, 8.82 mmol) in water (6 ml) was added. The reaction mixture was stirred at room temperature for 48 h. The mixture was diluted with water and extracted with EA. The organic layer was dried over sodium sulfate, filtered and the solvent was removed under reduced pressure to give 394 mg of the crude title compound.
LC/MS (method LC4): m/z=302

Step 4: 4-(2-Chloro-6-methoxy-1-phenyl-1H-indole-3-carbonyl)-piperazine-1-carboxylic acid tert-butyl ester From the compound of step 3 (394 mg, 1.31 mmol), the title compound was prepared analogously as described in example 1, step 1. Yield: 730 mg of crude product.
LC/MS (method LC4): m/z=470

Step 5: 4-[6-Methoxy-1-phenyl-2-(2-methyl-phenoxy)-1H-indole-3-carbonyl]-piperazine-1-carboxylic acid tert-butyl ester From the compound of step 4, the title compound was prepared analogously as described in example 1, step 2, using 2-methylphenol. Yield: 480 mg.
LC/MS (method LC4): m/z=542

Step 6: [6-Hydroxy-1-phenyl-2-(2-methyl-phenoxy)-1H-indol-3-yl]-piperazin-1-yl-methanone A solution of boron tribromide (2.71 ml, 2.71 mmol, 1 M in DCM) was added dropwise at −78° C. to a solution of the compound of step 5 (245 mg, 452 µmol) in DCM (10 ml). The cooling bath was removed and the mixture was stirred at room temperature for 2 h. The solvent was evaporated and the residue was purified by preparative HPLC. The eluate was lyophilized overnight to give the title compound in the form of the [6-hydroxy-1-phenyl-2-(2-methyl-phenoxy)-1H-indol-3-yl]-piperazin-1-yl-methanone trifluoroacetic acid salt. Yield: 121 mg.

LC/MS (method LC1): m/z=427.19, Rt=1.24 min $^1$H-NMR: δ (ppm)=2.11 (s, 3H), 2.98 (br s, 4H), 3.66 (br s, 4H), 6.55 (d, 1H), 6.72-6.75 (m, 2H), 6.91 (t, 1H), 7.03 (dt, 1H), 7.12 (d, 1H), 7.40-7.46 (m, 4H), 7.51 (t, 2H), 8.74 (br s, 2H), 9.26 (s, 1H)

EXAMPLE 8

4-[6-Hydroxy-1-phenyl-2-(2-methyl-phenoxy)-1H-indole-3-carbonyl]-piperazine-1-carboxylic acid tert-butyl ester

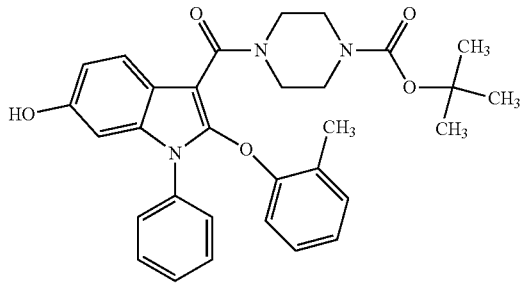

To a solution of 111 mg (239 µmol) of the compound of example 7 in MOH (2.2 ml) and THF (2.2 ml) was added sodium hydrogencarbonate (40.2 mg, 478 µmol) and a solution of di-tert-butyl dicarbonate (52.2 mg, 239 µmol) in THF (4.4 ml). The reaction mixture was stirred at room temperature overnight. The solvents were evaporated and the resulting solid was dissolved in water and EA. The organic layer was separated, dried over sodium sulfate, filtered, and evaporated under reduced pressure. The residue was purified by silica gel chromatography (EA/HEP). 63 mg of the title compound were obtained.

LC/MS (method LC4): m/z=528

EXAMPLE 9

[6-Chloro-1-phenyl-2-(2-methyl-phenoxy)-1H-indol-3-yl]-piperazin-1-yl-methanone

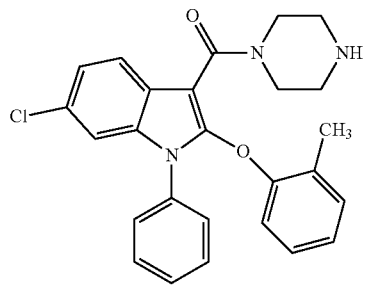

Step 1: 2,6-Dichloro-1H-indole-3-carbaldehyde

The title compound was obtained from 6-chloro-1,3-dihydro-indol-2-one (2.00 g, 11.9 mmol) analogously as described in example 7, step 2. Yield: 596 mg.

LC/MS (method LC4): m/z=214

Step 2: 2,6-Dichloro-1-phenyl-1H-indole-3-carbaldehyde

To a suspension of 500 mg pulverized molecular sieve (4 Å), the compound of step 1 (295 mg, 1.38 mmol), phenylboronic acid (336 mg, 2.76 mmol) and copper(II) acetate (500 mg, 2.76 mmol) in DCM (10 ml) was added pyridine (223 µl, 2.76 mmol) and triethylamine (384 µl, 2.76 mmol). The reaction mixture was stirred at room temperature for 4 days. The mixture was diluted with water and extracted with DCM. The organic layer was separated, dried over sodium sulfate, filtered, evaporated under reduced pressure. The residue was purified by silica gel chromatography (EA/HEP 1:4). 345 mg of the title compound were obtained.

LC/MS (method LC4): m/z=291

Step 3: 2,6-Dichloro-1-phenyl-1H-indole-3-carboxylic acid

From the compound of step 2 (345 mg, 1.19 mmol), the title compound was prepared analogously as described in example 7, step 3. Yield: 370 mg of crude product.

LC/MS (method LC4): m/z=307

Step 4: 4-(2,6-Dichloro-1-phenyl-1H-indole-3-carbonyl)-piperazine-1-carboxylic acid tert-butyl ester From the compound of step 3 (370 mg, 1.21 mmol), the title compound was prepared analogously as described in example 1, step 1. Yield: 738 mg of crude product.

LC/MS (method LC4): m/z=475

Step 5: 4-[6-Chloro-1-phenyl-2-(2-methyl-phenoxy)-1H-indole-3-carbonyl]-piperazine-1-carboxylic acid tert-butyl ester From the compound of step 4 (100 mg, 211 µmol), the title compound was prepared analogously as described in example 1, step 2, using 2-methylphenol. Yield: 29 mg.

LC/MS (method LC4): m/z=547

Step 6: [6-Chloro-1-phenyl-2-(2-methyl-phenoxy)-1H-indol-3-yl]-piperazin-1-yl-methanone From the compound of step 5 (29.0 mg, 53.1 µmol), the title compound was prepared analogously as described in example 1, step 3, and obtained in the form of the [6-chloro-1-phenyl-2-(2-methyl-phenoxy)-1H-indol-3-yl]-piperazin-1-yl-methanone trifluoroacetic acid salt. Yield: 23 mg.

LC/MS (method LC1): m/z=445.16, Rt=1.54 min

¹H-NMR: δ (ppm)=2.13 (s, 3H), 2.98 (br s, 4H), 3.63 (br s, 4H), 6.84 (d, 1H), 6.96 (dt, 1H), 7.05 (dt, 1H), 7.14-7.16 (m, 2H), 7.28 (dd, 1H), 7.46-7.56 (m, 5H), 7.66 (d, 1H), 8.75 (br s, 2H)

EXAMPLE 10

[2-(3-Fluoro-2-methyl-phenoxy)-1-thiophen-3-yl-1H-indol-3-yl]-piperazin-1-yl-methanone

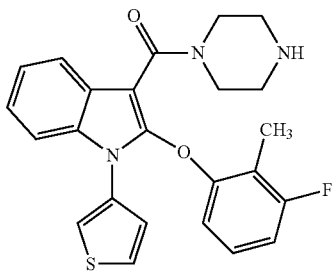

Step 1: 2-Chloro-1-thiophen-3-yl-1H-indole-3-carbaldehyde

The title compound was prepared analogously as described in example 9, step 2, using 2-chloro-1H-indole-3-carbaldehyde (300 mg, 1.67 mmol) and thiophene-3-boronic acid. Yield: 123 mg.
LC/MS (method LC4): m/z=262

Step 2: 2-Chloro-1-thiophen-3-yl-1H-indole-3-carboxylic acid

From the compound of step 1 (123 mg, 0.47 mmol), the title compound was prepared analogously as described in example 7, step 3. Yield: 133 mg of crude product.
LC/MS (method LC4): m/z=278

Step 3: 4-(2-Chloro-1-thiophen-3-yl-1H-indole-3-carbonyl)-piperazine-1-carboxylic acid tert-butyl ester From the compound of step 2 (133 mg, 0.48 mmol), the title compound was prepared analogously as described in example 1, step 1. Yield: 245 mg.
LC/MS (method LC4): m/z=446

Step 4: 4-[2-(3-Fluoro-2-methyl-phenoxy)-1-thiophen-3-yl-1H-indole-3-carbonyl]-piperazine-1-carboxylic acid tert-butyl ester From the compound of step 3 (50 mg, 112 μmol), the title compound was prepared analogously as described in example 1, step 2, using 3-fluoro-2-methylphenol. Yield: 11 mg.
LC/MS (method LC4): m/z=536

Step 5: [2-(3-Fluoro-2-methyl-phenoxy)-1-thiophen-3-yl-1H-indol-3-yl]-piperazin-1-yl-methanone From the compound of step 4 (10.0 mg, 18.7 μmol), the title compound was prepared analogously as described in example 1, step 3, and obtained in the form of the [2-(3-fluoro-2-methyl-phenoxy)-1-thiophen-3-yl-1H-indol-3-yl]-piperazin-1-yl-methanone trifluoroacetic acid salt. Yield: 13 mg.
LC/MS (method LC1): m/z=435.14; Rt=1.43 min
¹H-NMR: δ (ppm)=2.13 (s, 3H), 3.01 (br s, 4H), 3.65 (br s, 4H), 6.67 (d, 1H), 6.91 (t, 1H), 7.09 (q, 1H), 7.23 (dd, 1H), 7.25-7.28 (m, 3H), 7.64-7.66 (m, 1H), 7.71 (dd, 1H), 7.78 (dd, 1H), 8.74 (br s, 2H)

EXAMPLE 11

{2-(5-Fluoro-2-methyl-phenoxy)-1-[2-(3-methoxy-propoxy)-phenyl]-1H-indol-3-yl}-piperazin-1-yl-methanone

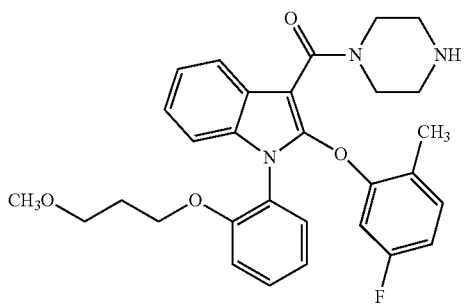

Step 1

1-Iodo-2-(3-methoxy-propoxy)-benzene

To a stirred solution of 2-iodophenol (3.00 g, 13.6 mmol), 3-methoxy-1-propanol (1.57 ml, 16.4 mmol) and triphenylphosphine (4.29 g, 16.4 mmol) in THF (15 ml) was added dropwise diisopropyl azodicarboxylate (3.22 ml, 16.4 mmol). The reaction mixture was stirred at room temperature overnight. The mixture was quenched with water and extracted with EA. The organic layer was separated, dried over sodium sulfate, filtered, and evaporated under reduced pressure: The residue was purified by silica gel chromatography (EA/HEP 1:5). 4.00 g of the title compound were obtained.
LC/MS (method LC4): m/z=293

Step 2:
1-[2-(3-Methoxy-propoxy)-phenyl]-1H-indole

A mixture of the compound of step 1 (8.00 g, 27.4 mmol), indole (3.21 g, 27.4 mmol), copper(I) iodide (522 mg, 2.74 mmol), L-proline (636 mg, 5.48 mmol) and potassium carbonate (7.68 g, 54.8 mmol) in DMSO (50 ml) was stirred for 26 h at 125° C. The mixture was quenched with water and extracted with EA. The organic layer was separated, dried over sodium sulfate, filtered and evaporated. The residue was purified by preparative HPLC. The eluate was lyophilized overnight to give 3.10 g of the title compound.
LC/MS (method LC4): m/z=282

Step 3: 1-[2-(3-Methoxy-propoxy)-phenyl]-1,3-dihydro-indol-2-one

The compound of step 2 (3.09 g, 11.0 mmol) was dissolved in DCM (83 ml), and N-chlorosuccinimide (1.54 g, 11.6 mmol) was added. The reaction mixture was stirred at room temperature for 2 h. The solvent was removed, the resulting solid was dissolved in concentrated acetic acid (45 ml) and heated to 70° C. After the addition of phosphoric acid (9.35 ml, 137 mmol; 85%), the reaction mixture was heated to 120° C. for 2 h. The cooled mixture was diluted with water, extracted with EA, the organic layer separated, dried over sodium sulfate, filtered, and evaporated. The residue was purified by silica gel chromatography (EA/HEP 1:6). 2.38 g of the title compound was obtained.

LC/MS (method LC4): m/z=298

Step 4: 2-Chloro-1-[2-(3-methoxy-propoxy)-phenyl]-1H-indole-3-carbaldehyde

From the compound of step 3 (1.62 g, 5.45 mmol), the title compound was prepared analogously as described in example 7, step 2. Yield: 1.31 g.

LC/MS (method LC4): m/z=344

Step 5: 2-Chloro-1-[2-(3-methoxy-propoxy)-phenyl]-1H-indole-3-carboxylic acid

To the compound of step 4 (100 mg, 2914 μmol) in a mixture of acetone (2.8 ml), water (1.36 ml) and a disodium hydrogenphosphate/potassium dihydrogenphosphate buffer solution (2.0 ml; pH 7.0) was added with stirring at room temperature potassium permanganate (90.0 mg, 570 μmol) in small portions. After stirring at room temperature for 3 days, the mixture was diluted with water and EA was added. The organic layer was separated, dried over sodium sulfate, filtered, and evaporated. The residue was purified by silica gel chromatography (EA/HEP 4:1). 50 mg of the title compound were obtained.

LC/MS (method LC4): m/z=342

Step 6: 4-{2-Chloro-1-[2-(3-methoxy-propoxy)-phenyl]-1H-indole-3-carbonyl}-piperazine-1-carboxylic acid tert-butyl ester To a solution of 200 mg (556 μmol) of the compound of step 5 in DMF (5 ml) and NMM (122 μl, 1.11 mmol) was added O-[(ethoxycarbonyl)cyanomethyleneamino]-N,N,N',N'-tetramethyluronium tetrafluoroborate (201 mg, 612 μmol), and the mixture was stirred at room temperature for 30 min. tert-Butyl 1-piperazinecarboxylate (114 mg, 612 μmol) was then added and the reaction mixture was stirred for 3 h. The mixture was quenched with water and extracted with EA. The organic layer was separated, dried over sodium sulfate, filtered, and evaporated. The residue was purified by silica gel chromatography (EA/HEP 2:5). 285 mg of the title compound were obtained.

LC/MS (method LC4): m/z=529

Step 7: {2-(5-Fluoro-2-methyl-phenoxy)-1-[2-(3-methoxy-propoxy)-phenyl]-1H-indol-3-yl}-piperazin-1-yl-methanone The compound of step 6 (40.0 mg, 75.8 μmol) was reacted analogously as described in example 1, step 2, using 5-fluoro-2-methylphenol and stirring the reaction mixture at 150° C. in a microwave reactor for 13 h. The title compound was obtained in the form of the {2-(5-fluoro-2-methyl-phenoxy)-1-[2-(3-methoxy-propoxy)-phenyl]-1H-indol-3-yl}-piperazin-1-yl-methanone trifluoroacetic acid salt. Yield: 3 mg.

LC/MS (method LC1): m/z=517.24; Rt=1.50 min

¹H-NMR: δ (ppm)=1.61-1.69 (m, 1H), 2.00 (s, 3H), 3.02 (s, 3H), 3.04 (d, 2H), 3.07 (br s, 4H), 3.70 (br s, 4H), 3.86-3.90 (m, 1H), 3.92-3.97 (m, 1H), 6.58 (dd, 1H), 6.79 (dt, 1H), 6.91 (d, 1H), 7.04 (t, 1H), 7.11-7.26 (m, 4H), 7.40-7.45 (m, 2H), 7.67 (d, 1H), 8.76 (br s, 2H)

EXAMPLE 12

[6-(2-Methoxy-ethoxy)-1-phenyl-2-(2-methyl-phenoxy)-1H-indol-3-yl]-piperazin-1-yl-methanone

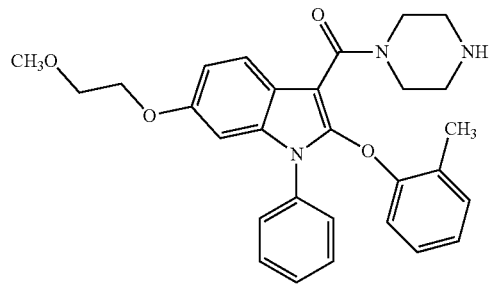

Step 1: 4-[6-(2-Methoxy-ethoxy)-1-phenyl-2-(2-methyl-phenoxy)-1H-indole-3-carbonyl]-piperazine-1-carboxylic acid tert-butyl ester The compound of example 8 (63.0 mg, 119 μmol) was dissolved in DMF, and cesium carbonate (116 mg, 358 μmol) and 2-bromoethyl methyl ether (13.5 μl, 143 μmol) were added. The reaction mixture was stirred at 50° C. for 3 h. The cooled mixture was diluted with water and extracted with EA. The organic layer was dried over sodium sulfate, filtered and evaporated under reduced pressure. The residue was purified by silica gel chromatography (EA/HEP). 60.0 mg of the title compound were obtained.

LC/MS (method LC4): m/z=586

Step 2: [6-(2-Methoxy-ethoxy)-1-phenyl-2-(2-methyl-phenoxy)-1H-indol-3-yl]-piperazin-1-yl-methanone From the compound of step 1 (30.0 mg, 51.2 μmol), the title compound was prepared analogously as described in example 1, step 3, and purified by silica gel chromatography (EA/HEP). The obtained product was dissolved in a small quantity of MOH, mixed with hydrochloric acid (0.1 M) and lyophilized overnight. 25.0 mg of the title compound were obtained in the form of the [6-(2-methoxy-ethoxy)-1-phenyl-2-(2-methyl-phenoxy)-1H-indol-3-yl]-piperazin-1-yl-methanone hydrochloride.

LC/MS (method LC2): m/z=485.23; Rt=1.52 min

¹H-NMR (400 MHz): δ (ppm)=2.12 (s, 3H), 2.96 (br s, 4H), 3.28 (s, 3H), 3.61-3.63 (m, 2H), 3.68 (br s, 4H), 4.02-4.04 (m, 2H), 6.67 (d, 1H), 6.74 (d, 1H), 6.89-6.94 (m, 2H), 7.04 (dt, 1H), 7.12 (d, 1H), 7.41-7.56 (m, 6H), 9.10 (br s, 2H)

EXAMPLE 13

[2-(3-Fluoro-2-methyl-benzyl)-5-methoxy-1-phenyl-1H-indol-3-yl]-piperazin-1-yl-methanone

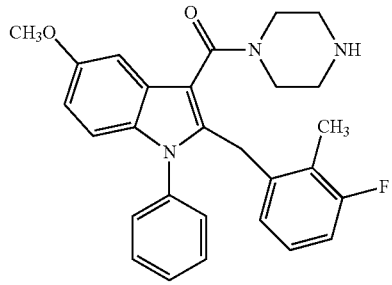

Step 1: 5-Methoxy-1-phenyl-1H-indole

To a mixture of 5-methoxyindole (1.00 g, 6.79 mmol), copper(I) iodide (129 mg, 0.68 mmol), L-proline (156 mg, 1.36 mmol) and potassium carbonate (1.88 g, 13.6 mmol) in DMSO (7.5 ml) was added iodobenzene (0.76 ml, 6.79 mmol). The reaction mixture was stirred for 10 h at 125° C. in a microwave reactor. The mixture was then quenched with water and extracted with EA. The organic layer was separated, dried over sodium sulfate, filtered and evaporated. The residue was purified by silica gel chromatography (EA/HEP 1:15). 951 mg of the title compound were obtained.
LC/MS (method LC4): m/z=224

Step 2: 5-Methoxy-1-phenyl-1,3-dihydro-indol-2-one

The compound of step 1 (800 mg, 3.58 mmol) was dissolved in DCM (25 ml), and N-chlorosuccinimide (526 mg, 3.94 mmol) was added. The reaction mixture was stir at room temperature overnight. The solvent was removed, the resulting solid was dissolved in concentrated acetic acid (15 ml) and heated to 70° C. After the addition of phosphoric acid (3.04 ml, 44.6 mmol; 85%) the reaction mixture was heated to 130° C. for 2.5 h. The cooled mixture was diluted with water and extracted with EA. The extracts were dried over sodium sulfate, filtered and evaporated. The residue was purified by silica gel chromatography (EA/HEP 1:3). 557 mg of the title compound were obtained.
LC/MS (method LC4): m/z=240

Step 3: 2-Chloro-5-methoxy-1-phenyl-1H-indole-3-carbaldehyde

A solution of DMF (2.3 ml) and DCM (2.3 ml) under argon was cooled to 0° C. With stirring, phosphorus oxychloride (2.14 ml, 22.9 mmol) was added within 15 min, and the mixture was stirred for further 30 min at 0° C. Then the compound of step 2 (557 mg, 2.33 mmol), dissolved in chloroform (5.77 ml) and pyridine (1.15 ml), was added to the cooled solution. The reaction mixture was stirred at room temperature overnight. The mixture was slowly poured into 300 ml of ice and after a few minutes EA was added. The organic layer was separated, dried over sodium sulfate, filtered and evaporated under reduced pressure. Column chromatography of the residue on silica gel (EA/HEP 1:8) yielded 456 mg of the title compound as a white solid.
LC/MS (method LC4): m/z=286

Step 4: 2-Chloro-5-methoxy-1-phenyl-1H-indole-3-carboxylic acid

The compound of step 3 (456 mg, 1.59 mmol) was dissolved in tert-butanol (15 ml) and 2-methyl-2-butene (3 ml), and a solution of sodium chlorite (1.32 g, 14.6 mmol) and sodium dihydrogenphosphate (1.32 g, 11.0 mmol) in water (6 ml) was added. The reaction mixture was stirred at room temperature for 48 h and afterwards at 80° C. for 2.5 h. The mixture was diluted with water and extracted with EA. The organic layer was dried over sodium sulfate, filtered and the solvent was removed under reduced pressure to give 602 mg of the crude title compound.
LC/MS (method LC4): m/z=302

Step 5: 4-(2-Chloro-5-methoxy-1-phenyl-1H-indole-3-carbonyl)-piperazine-1-carboxylic acid tert-butyl ester To a solution of 602 mg (1.99 mmol) of the compound of step 4, tert-butyl 1-piperazinecarboxylate (372 mg, 1.99 mmol), EDC (421 mg, 2.19 mmol) and HOAT (312 mg, 2.29 mmol) in DMF (5 ml) was added NMM (0.66 ml, 5.98 mmol), and the reaction mixture was stirred at room temperature overnight. The mixture was quenched with water and extracted with EA. The organic layer was separated, dried over sodium sulfate, filtered and evaporated to give 930 mg of the title compound.
LC/MS (method LC4): m/z=470

Step 6: 4-[2-(3-Fluoro-2-methyl-benzyl)-5-methoxy-1-phenyl-1H-indole-3-carbonyl]-piperazine-1-carboxylic acid tert-butyl ester To a suspension of zinc (322 mg, 4.92 mmol) in dry THF (770 µl) in a dry flask under argon was added 1,2-dibromoethane (10.6 µl, 0.123 mmol). The mixture was heated three times to reflux with a heat-gun. After 5 min the flask was placed in an ice bath and a solution of 3-fluoro-2-methylbenzylbromide (500 mg, 2.46 mmol) in dry THF (1.5 ml) was added slowly, so that the temperature remained at 0° C. The mixture was stirred at 0° C. for 3 h. The cooled suspension was added dropwise to a precooled solution (−78° C.) of B-OM-9-BBN (2.45 ml, 2.45 mmol, 1 M in hexane). The mixture was then stirred at room temperature for 30 min. DMF (7 ml) was added, followed by the compound of step 5 (115 mg, 245 µmol), palladium(II) acetate (5.49 mg, 24.5 µmol) and S—PHOS (20.1 mg, 48.9 µmol). The reaction mixture was stirred at 100° C. for 2 h. The cooled mixture was quenched with water and extracted with EA. The organic layer was separated, dried over sodium sulfate, filtered, and evaporated under reduced pressure. The residue was purified by preparative HPLC. The eluate was lyophilized overnight to give 72 mg of the title compound.
LC/MS (method LC4): m/z=558

Step 7: [2-(3-Fluoro-2-methyl-benzyl)-5-methoxy-1-phenyl-1H-indol-3-yl]-piperazin-1-yl-methanone To a solution of the compound of step 6 (72.0 mg, 129 µmol) in DCM (8 ml) was added TFA (2 ml), and the reaction mixture was stirred at room temperature for 2 h. The solvents were evaporated. The solid was dissolved in MOH and water and lyophilized to give the title compound in the form of the [2-(3-fluoro-2-methyl-benzyl)-5-methoxy-1-phenyl-1H-indol-3-yl]-piperazin-1-yl-methanone trifluoroacetic acid salt as a white solid. Yield: 70.0 mg.

LC/MS (method LC2): m/z=457.22; Rt=1.65 min

¹H-NMR: δ (ppm)=1.84 (s, 3H), 2.91 (br s, 2H), 3.21 (br s, 2H), 3.52 (br s, 2H), 3.73 (br s, 2H), 3.80 (s, 3H), 4.11 (s, 2H), 6.63 (d, 1H), 6.81 (dd, 1H), 6.88-6.92 (m, 2H), 6.99 (q, 1H), 7.04 (d, 1H), 7.27 (dd, 2H), 7.48-7.52 (m, 3H), 8.78 (br s, 2H)

EXAMPLE 14

[2-(3-Fluoro-2-methyl-benzyl)-1-(4-fluoro-phenyl)-6-methoxy-1H-indol-3-yl]-piperazin-1-yl-methanone

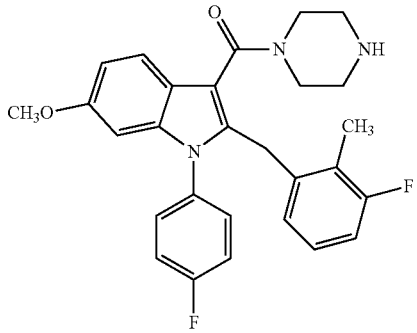

Step 1: 1-(4-Fluoro-phenyl)-6-methoxy-1,3-dihydro-indol-2-one

To a mixture of 6-methoxy-1,3-dihydro-indol-2-one (500 mg, 3.06 mmol), copper(I) iodide (58.3 mg, 306 μmol), N,N'-dimethylethylenediamine (65.3 μl, 613 μmol) and potassium carbonate (932 mg, 6.74 mmol) in ACN (7 ml) was added 4-fluoroiodobenzene (474 μl, 3.68 mmol). The reaction mixture was stirred for 3 h at 120° C. in a microwave reactor. The mixture was quenched with water and extracted with EA. The organic layer was separated, dried over sodium sulfate, filtered and evaporated. The residue was purified by silica gel chromatography (EA/HEP 1:4). 510 mg of the title compound were obtained.

LC/MS (method LC4): m/z=258

Step 2: 2-Chloro-1-(4-fluoro-phenyl)-6-methoxy-1H-indole-3-carbaldehyde

From the compound of step 1 (505 mg, 1.96 mmol), the title compound was prepared analogously as described in example 13, step 3. Yield: 286 mg.

LC/MS (method LC4): m/z=304

Step 3: 2-Chloro-1-(4-fluoro-phenyl)-6-methoxy-1H-indole-3-carboxylic acid

From the compound of step 2 (286 mg, 942 μmol), the title compound was prepared analogously as described in example 13, step 4. Yield: 325 mg of crude product.

LC/MS (method LC4): m/z=320

Step 4: 4-[2-Chloro-1-(4-fluoro-phenyl)-6-methoxy-1H-indole-3-carbonyl]-piperazine-1-carboxylic acid tert-butyl ester From the compound of step 3 (325 mg, 1.02 mmol), the title compound was prepared analogously as described in example 13, step 5. Yield: 479 mg.

LC/MS (method LC4): m/z=488

Step 5: 4-[2-(3-Fluoro-2-methyl-benzyl)-1-(4-fluoro-phenyl)-6-methoxy-1H-indole-3-carbonyl]-piperazine-1-carboxylic acid tert-butyl ester From the compound of step 4 (80.0 mg, 164 μmol), the title compound was prepared analogously as described in example 13, step 6. Yield: 49 mg.

LC/MS (method LC4): m/z=576

Step 6: [2-(3-Fluoro-2-methyl-benzyl)-1-(4-fluoro-phenyl)-6-methoxy-1H-indol-3-yl]-piperazin-1-yl-methanone From the compound of step 5 (49.0 mg, 85.1 μmol), the title compound was prepared analogously as described in example 13, step 7, and obtained in the form of the [2-(3-fluoro-2-methyl-benzyl)-1-(4-fluoro-phenyl)-6-methoxy-1H-indol-3-yl]-piperazin-1-yl-methanone trifluoroacetic acid salt. Yield: 46 mg.

LC/MS (method LC1): m/z=475.21; Rt=1.44 min

¹H-NMR: δ (ppm)=1.86 (s, 3H), 2.94 (br s, 2H), 3.19 (br s, 2H), 3.57 (br s, 2H), 3.66 (s, 3H), 3.70 (br s, 2H), 4.07 (s, 2H), 6.43 (d, 1H), 6.61 (d, 1H), 6.86 (dd, 1H), 6.90 (t, 1H), 6.98 (q, 1H), 7.31-7.33 (m, 4H), 7.50 (d, 1H), 8.78 (br d, 2H)

EXAMPLE 15

[1-[2-(2-Methoxy-ethoxy)-phenyl]-2-(2-methyl-benzyl)-1H-indol-3-yl]-piperazin-1-yl-methanone

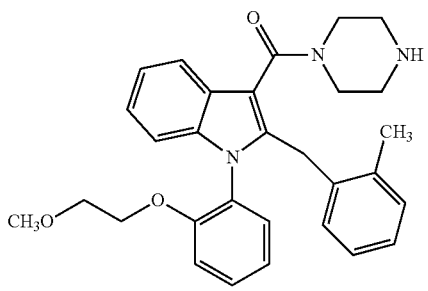

Step 1: 1-Iodo-2-(2-methoxy-ethoxy)-benzene

To a mixture of 2-iodophenol (5.00 g, 22.7 mmol) and potassium carbonate (4.71 g, 34.1 mmol) in ACN (7 ml) was added 2-bromoethyl methyl ether (3.79 g, 27.3 mmol). The reaction mixture was stirred for 2 h at 110° C. in a microwave reactor. The cooled mixture was quenched with water and extracted with EA. The organic layer was separated, washed with brine, dried over sodium sulfate, filtered, and evaporated under reduced pressure. The residue was purified by silica gel chromatography (EA/HEP 1:4). 4.59 g of the title compound were obtained.

LC/MS (method LC4): m/z=288

Step 2: 2-(2-methoxy-ethoxy)-phenylboronic acid

To a solution of the compound of step 1 (2.20 g, 7.91 mmol) in toluene (20 ml) and THF (4 ml) was added triisopropyl borate (2.19 ml, 9.49 mmol), and the mixture was cooled to −78° C. n-Butyllithium (3.79 ml, 9.49 mmol, 2.5 M in hexane) was added dropwise and the reaction mixture was stirred at −78° C. for 1.5 h. The cooling bath was removed and the reaction mixture was allowed to warm to −20° C. Then 2 N hydrochloric acid (7 ml) was added. When the mixture had reached room temperature, water and EA were added. The organic layer was separated, dried over sodium sulfate, filtered and evaporated in vacuo. The residue was purified by silica gel chromatography (EA/HEP 1:4). 766 mg of the title compound were obtained.

LC/MS (method LC4): m/z=179

Step 3: 2-Chloro-1-[2-(2-methoxy-ethoxy)-phenyl]-1H-indole-3-carbaldehyde

To a suspension of 500 mg pulverized molecular sieves (4 Å), the compound of step 2 (761 mg, 3.88 mmol), 2-chloro-1H-indole-3-carbaldehyde (465 mg, 2.59 mmol) and copper (II) acetate (940 mg, 5.18 mmol) in DCM (20 ml) was added pyridine (0.42 ml, 5.18 mmol) and triethylamine (0.72 ml, 5.18 mmol). The reaction mixture was stirred at room temperature for one week. The mixture was diluted with water and extracted with DCM. The organic layer was separated, dried over sodium sulfate, filtered and evaporated under reduced pressure. The residue was purified by preparative HPLC. The eluate was lyophilized overnight to give 56 mg of the title compound.

LC/MS (method LC4): m/z=330

Step 4: 2-Chloro-1-[2-(2-methoxy-ethoxy)phenyl]-1H-indole-3-carboxylic acid

From the compound of step 3 (100 mg, 303 µmol), the title compound was prepared analogously as described in example 13, step 4. Yield: 150 mg of crude product.

LC/MS (method LC4): m/z=328

Step 5: 4-{2-Chloro-1-[2-(2-methoxy-ethoxy)-phenyl]-1H-indole-3-carbonyl}-piperazine-1-carboxylic acid tert-butyl ester From the compound of step 4 (150 mg, 434 µmol), the title compound was prepared analogously as described in example 13, step 5. Yield: 207 mg.

LC/MS (method LC4): m/z=514

Step 6: 4-[1-[2-(2-Methoxy-ethoxy)-phenyl]-2-(2-methyl-benzyl)-1H-indole-3-carbonyl]-piperazine-1-carboxylic acid tert-butyl ester A solution of 2-methylbenzylzinc chloride (1.95 ml, 973 µmol, 0.5 M in THF) was added dropwise at −78° C. to a solution of B-OM-9-BBN (0.97 ml, 973 µmol, 1 M in hexane). The cooling bath was removed and the mixture was stirred at room temperature for 30 min. DMF (2 ml) was added, followed by the compound of step 5 (50 mg, 97.3 µmol), palladium(II) acetate (2.18 mg, 9.73 µmol) and S-PHOS (7.99 mg, 19.5 µmol). The reaction mixture was heated to 100° C. and stirred for 4 h. The mixture was diluted with water and extracted with EA. The organic layer was separated, dried over sodium sulfate, filtered and evaporated under reduced pressure. The residue was purified by preparative HPLC. The eluate was lyophilized overnight to give 14 mg of the title compound.

LC/MS (method LC4): m/z=584

Step 7: [1-[2-(2-Methoxy-ethoxy)-phenyl]-2-(2-methyl-benzyl)-1H-indol-3-yl]-piperazin-1-yl-methanone From the compound of step 6 (11.0 mg, 18.8 µmol), the title compound was prepared analogously as described in example 13, step 7, and obtained in the form of the [1-[2-(2-methoxy-ethoxy)-phenyl]-2-(2-methyl-benzyl)-1H-indol-3-yl]-piperazin-1-yl-methanone trifluoroacetic acid salt. Yield: 17 mg.

LC/MS (method LC1): m/z=483.25; Rt=1.40 min

¹H-NMR: δ (ppm)=1.92 (s, 3H), 2.88 (br s, 2H), 3.04 (s, 3H), 3.17 (br s, 2H), 3.68 (br s, 2H), 3.90 (br d, 1H), 3.94-3.98 (m, 1H), 4.01-4.06 (m, 1H), 4.12 (br d, 1H), 6.79 (d, 1H), 6.86 (d, 1H), 6.91-7.03 (m, 4H), 7.10-7.19 (m, 3H), 7.22 (d, 1H), 7.44-7.48 (m, 1H), 7.56 (d, 1H), 8.75 (br d, 2H)

EXAMPLE 16

[2-(3-Fluoro-2-methyl-benzyl)-1-phenyl-1H-indol-3-yl]-piperazin-1-yl-methanone

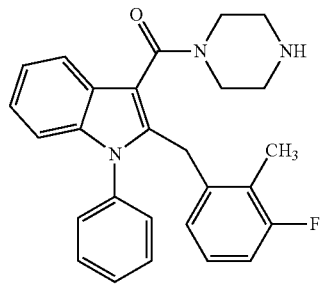

Step 1: 4-(2-Chloro-1-phenyl-1H-indole-3-carbonyl)-piperazine-1-carboxylic acid tert-butyl ester The title compound was prepared from 2-chloro-1-phenyl-1H-indole-3-carboxylic acid (cf. CA 1079739) (3.00 g, 11.0 mmol) analogously as described in example 13, step 5.

After purification by silica gel chromatography (EA/HEP 1:3), 4.51 g of the title compound were obtained.

LC/MS (method LC4): m/z=440

Step 2: 4-[2-(3-Fluoro-2-methyl-benzyl)-1-phenyl-1H-indole-3-carbonyl]-piperazine-1-carboxylic acid tert-butyl ester From the compound of step 1 (150 mg, 0.34 mmol), the title compound was prepared analogously as described in example 13, step 6. Yield: 126 mg.

LC/MS (method LC4): m/z=528

Step 3: [2-(3-Fluoro-2-methyl-benzyl)-1-phenyl-1H-indol-3-yl]-piperazin-1-yl-methanone From the compound of step 2 (126 mg, 239 µmol), the title compound was prepared analogously as described in example 13, step 7, and obtained in the form of the [2-(3-fluoro-2-methyl-benzyl)-1-phenyl-1H-indol-3-yl]-piperazin-1-yl-methanone trifluoroacetic acid salt. Yield: 130 mg.

LC/MS (method LC1): m/z=427.21; Rt=1.47 min

¹H-NMR: δ (ppm)=1.84 (s, 3H), 2.91 (br s, 2H), 3.20 (br s, 2H), 4.13 (s, 2H), 6.65 (d, 1H), 6.90 (t, 1H), 6.96-7.01 (m, 2H), 7.17 (t, 1H), 7.22 (t, 1H), 7.27-7.29 (m, 2H), 7.49-7.52 (m, 3H), 7.61 (d, 2H), 8.78 (br d, 2H)

EXAMPLE 17

[2-(2-Chloro-6-fluoro-benzyl)-1-phenyl-1H-indol-3-yl]-piperazin-1-yl-methanone

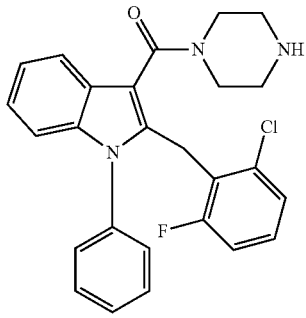

Step 1: 4-[2-(2-Chloro-6-fluoro-benzyl)-1-phenyl-1H-indole-3-carbonyl]-piperazine-1-carboxylic acid tert-butyl ester A solution of 500 mg (1.14 mmol) of the compound of example 16, step 1, in THF (8 ml) was cooled to −78° C. with an acetone/dry ice bath. Within 10 min a solution of n-butyl-lithium (0.55 ml, 1.36 mmol, 2.5 M in hexane) was added followed by 0.36 ml (2.27 mmol) of 2-chloro-6-fluoro-benzyl bromide. The cooling bath was removed and the reaction mixture was allowed to warm up slowly to room temperature and stirred overnight. The mixture was quenched with water and extracted with EA. The organic layer was separated, dried over sodium sulfate, filtered, and evaporated under reduced pressure. The residue was purified by preparative HPLC. The eluate was lyophilized overnight to give 216 mg of the title compound.

LC/MS (method LC4): m/z=549

Step 2: [2-(2-Chloro-6-fluoro-benzyl)-1-phenyl-1H-indol-3-yl]-piperazin-1-yl-methanone From the compound of step 1 (216 mg, 394 µmol), the title compound was prepared analogously as described in example 13, step 7, and obtained in the form of the [2-(2-chloro-6-fluoro-benzyl)-1-phenyl-1H-indol-3-yl]-piperazin-1-yl-methanone trifluoroacetic acid salt. Yield: 217 mg.

LC/MS (method LC2): m/z=447.15; Rt=1.60 min
$^1$H-NMR: δ (ppm)=2.89 (br s, 2H), 3.15 (br s, 2H), 3.68 (br s, 2H), 4.21 (br s, 2H), 6.98 (dd, 1H), 7.02-7.07 (m, 1H), 7.12-7.27 (m, 4H), 7.41 (br d, 2H), 7.53-7.59 (m, 4H), 8.85 (br s, 2H)

EXAMPLE 18

[2-(5-Fluoro-2-methyl-benzyl)-1-phenyl-1H-indol-3-yl]-piperazin-1-yl-methanone

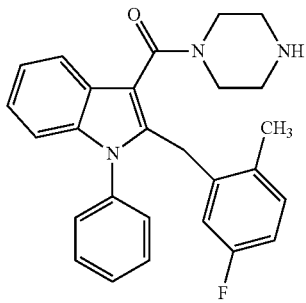

Step 1: 4-[2-(5-Fluoro-2-methyl-benzyl)-1-phenyl-1H-indole-3-carbonyl]-piperazine-1-carboxylic acid tert-butyl ester From the compound of example 16, step 1, (150 mg, 341 µmol) the title compound was prepared analogously as described in example 17, step 1, using 5-fluoro-2-methylbenzyl bromide. Yield: 9 mg.

LC/MS (method LC4): m/z=528

Step 2: [2-(5-Fluoro-2-methyl-benzyl)-1-phenyl-1H-indol-3-yl]-piperazin-1-yl-methanone From the compound of step 1 (9 mg, 17.1 µmol), the title compound was prepared analogously as described in example 13, step 7, and obtained in the form of the [2-(5-fluoro-2-methyl-benzyl)-1-phenyl-1H-indol-3-yl]-piperazin-1-yl-methanone trifluoroacetic acid salt. Yield: 8 mg.

LC/MS (method LC1): m/z=427.21; Rt=1.47 min
$^1$H-NMR: δ (ppm)=1.87 (s, 3H), 2.95 (br s, 2H), 3.22 (br s, 2H), 3.58 (br s, 2H), 3.74 (br s, 2H), 4.08 (s, 2H), 6.60 (dd, 1H), 6.84 (dt, 1H), 6.98-7.03 (m, 2H), 7.16-7.29 (m, 4H), 7.50-7.52 (m, 3H), 7.62 (d, 1H), 8.80 (br d, 2H)

EXAMPLE 19

[2-(2-Chloro-5-fluoro-benzyl)-1-phenyl-1H-indol-3-yl]-piperazin-1-yl-methanone

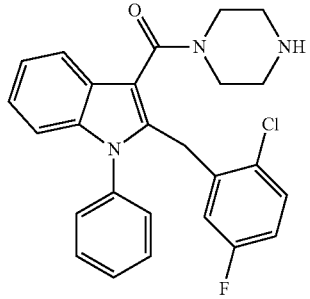

Step 1: 4-[2-(2-Chloro-5-fluoro-benzyl)-1-phenyl-1H-indole-3-carbonyl]-piperazine-1-carboxylic acid tert-butyl ester To a suspension of zinc (176 mg, 2.69 mmol) in dry THF (1 ml) in a dry flask under argon was added 1,2-dibromoethane (5.79 µl, 67.2 µmol). The mixture was heated three times to reflux with a heat-gun. After 5 min the flask was placed in an ice bath and a solution of 2-chloro-5-fluoro-benzylbromide (182 µl, 1.34 mmol) in dry THF (1.5 ml) was added slowly, so that the temperature remained at 0° C. The mixture was stirred at 0° C. for 3 h. Then the cooled suspension was added dropwise to a precooled solution (0° C.) of the compound of example 16, step 1 (59.0 mg, 134 µmol), nickel acetylacetonate (3.44 mg, 13.4 µmol) and tetrabutylammonium iodide (149 mg, 402 µmol) in THF (4 ml) and NMP (2 ml). The reaction mixture was stirred at 0° C. for 3 h and then at room temperature for 48 h. The mixture was quenched with water and extracted with EA. The organic layer was separated, dried over sodium sulfate, filtered, and evaporated under reduced pressure. The residue was purified by preparative HPLC. The eluate was lyophilized overnight to give 17 mg of the title compound.

LC/MS (method LC4): m/z=549

Step 2: [2-(2-Chloro-5-fluoro-benzyl)-1-phenyl-1H-indol-3-yl]-piperazin-1-yl-methanone From the compound of step 1 (17 mg, 31 µmol), the title compound was prepared analogously as described in example 13, step 7, and obtained in the form of the [2-(2-chloro-5-fluoro-benzyl)-1-phenyl-1H-indol-3-yl]-piperazin-1-yl-methanone trifluoroacetic acid salt. Yield: 16 mg.

LC/MS (method LC1): m/z=447.15; Rt=1.46 min $^1$H-NMR: δ (ppm)=3.02 (br s, 2H), 3.22 (br s, 2H), 3.57 (br s, 2H), 3.75 (br s, 2H), 4.22 (s, 2H), 6.80 (dd, 1H), 7.00 (d, 1H), 7.05 (dt, 1H), 7.17-7.25 (m, 2H), 7.29-7.33 (m, 3H), 7.50-7.55 (m, 3H), 7.63 (d, 1H), 8.81 (br d, 2H)

EXAMPLE 20

[2-(3-Fluoro-2-methyl-benzyl)-5-hydroxy-1-phenyl-1H-indol-3-yl]-piperazin-1-yl-methanone

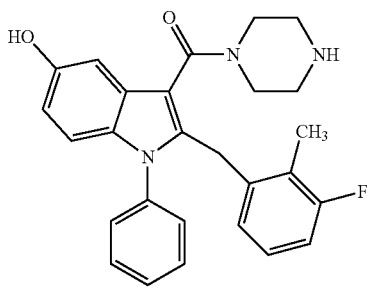

A solution of boron tribromide (87.5 µl, 87.5 µmol, 1 M in DCM) was added dropwise at −78° C. to a solution of the compound of example 13 (25.0 mg, 43.7 µmol) in DCM (1 ml). The cooling bath was removed and the mixture was stirred at room temperature overnight. The solvent was evaporated and the resulting solid was purified by preparative HPLC. The eluate was lyophilized overnight to give the title compound in the form of the [2-(3-fluoro-2-methyl-benzyl)-5-hydroxy-1-phenyl-1H-indol-3-yl]-piperazin-1-yl-methanone trifluoroacetic acid salt. Yield: 9 mg.

LC/MS (method LC1): m/z=443.20; Rt=1.37 min $^1$H-NMR: δ (ppm)=1.84 (s, 3H), 2.90 (br s, 2H), 3.17 (br s, 2H), 3.58 (br s, 2H), 3.68 (br s, 2H), 4.10 (s, 2H), 6.62 (d, 1H), 6.67 (dd, 1H), 6.81 (d, 1H), 6.87-6.92 (m, 2H), 6.98 (q, 2H), 7.25 (d, 2H), 7.46-7.51 (m, 3H), 8.81 (br d, 2H), 9.10 (s, 1H)

EXAMPLE 21

[2-(3-Fluoro-2-methyl-benzyl)-1-(4-fluoro-phenyl)-6-hydroxy-1H-indol-3-yl]-piperazin-1-yl-methanone

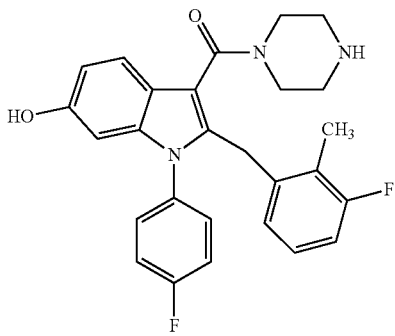

A solution of boron tribromide (153 µl, 153 µmol, 1 M in DCM) was added dropwise at −78° C. to a solution of the compound of example 14 (30.0 mg, 50.9 µmol) in DCM (1 ml). The cooling bath was removed and the reaction mixture was stirred at room temperature overnight. The mixture was again cooled to −78° C. and boron tribromide was added (153 µl, 153 µmol, 1 M in DCM). The reaction mixture was stirred at room temperature for 3 h. Then the solvent was evaporated and the resulting solid was purified by silica gel chromatography (DCM/MOH 10:1+2% aqueous ammonia). The eluate was evaporated, the residue dissolved in a small quantity of MOH, mixed with hydrochloric acid (0.1 M) and lyophilized overnight to give 18.0 mg of the title compound in the form of the [2-(3-fluoro-2-methyl-benzyl)-1-(4-fluoro-phenyl)-6-hydroxy-1H-indol-3-yl]-piperazin-1-yl-methanone hydrochloride.

LC/MS (method LC3): m/z=461.19; Rt=1.46 min $^1$H-NMR: δ (ppm)=1.86 (s, 3H), 3.93 (br s, 2H), 3.16 (br s, 2H), 3.62 (br s, 2H), 3.71 (br s, 2H), 4.06 (s, 2H), 6.31 (d, 1H), 6.61 (d, 1H); 6.72 (dd, 1H), 6.89 (t, 1H), 6.98 (q, 1H), 7.28-7.32 (m, 4H), 7.38 (d, 1H), 9.12 (br s, 2H), 9.21 (s, 1H)

EXAMPLE 22

[1-Cyclohex-2-enyl-2-(5-fluoro-2-methyl-phenoxy)-1H-indol-3-yl]-piperazin-1-yl-methanone

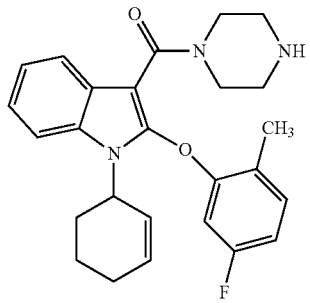

Step 1: 2-Chloro-1-cyclohex-2-enyl-1H-indole-3-carbaldehyde

To a solution of 2-chloro-1H-indole-3-carbaldehyde (2.00 g, 11.1 mmol) in DMF (15 ml) was added sodium hydride (468 mg, 11.7 mmol, 60% dispersion in mineral oil). Under an argon atmosphere, the suspension was stirred at 40° C. for 20 min and then allowed to cool to room temperature. After the addition of 3-bromocyclohexene (2.56 ml, 22.3 mmol) the reaction mixture was stirred at room temperature for 1 h. The mixture was then quenched with water and extracted with EA. The organic layer was separated, dried over sodium sulfate, filtered and evaporated. The residue was and purified by silica gel chromatography (EA/HEP 1:10). 1.13 g of the title compound were obtained.

LC/MS (method LC4): m/z=260

Step 2: 2-Chloro-1-cyclohex-2-enyl-1H-indole-3-carboxylic acid

From the compound of step 1 (1.13 g, 4.35 mmol), the title compound was prepared analogously as described in example 7, step 3. Yield: 1.61 g of crude product.

LC/MS (method LC4): m/z=276

Step 3: 4-(2-Chloro-1-cyclohex-2-enyl-1H-indole-3-carbonyl)-piperazine-1-carboxylic acid tert-butyl ester From the crude compound of step 2 (1.61 g), the title compound was prepared analogously as described in example 1, step 1. Yield: 738 mg.
LC/MS (method LC4). m/z=444

Step 4: 4-[1-Cyclohex-2-enyl-2-(5-fluoro-2-methyl-phenoxy)-1H-indole-3-carbonyl]-piperazine-1-carboxylic acid tert-butyl ester From the compound of step 3 (170 mg, 1.35 mmol), the title compound was prepared as described in example 1, step 2. The mixture was quenched with water and extracted with EA. The organic layer was separated, dried over sodium sulfate, filtered and evaporated under reduced pressure. The residue was purified by silica gel chromatography (EA/HEP). Yield: 108 mg.
LC/MS (method LC4): m/z=534

Step 5: [1-Cyclohex-2-enyl-2-(5-fluoro-2-methyl-phenoxy)-1H-indol-3-yl]-piperazin-1-yl-methanone The compound of step 4 (42.0 mg, 78.7 µmol) was reacted analogously as described in example 1, step 3. The obtained solid was purified by preparative HPLC, the eluate lyophilized overnight, the residue dissolved in a small quantity of MOH, mixed with hydrochloric acid (0.1 M) and lyophilized overnight. 24.0 mg of the title compound were obtained in the form of the [1-cyclohex-2-enyl-2-(5-fluoro-2-methyl-phenoxy)-1H-indol-3-yl]-piperazin-1-yl-methanone hydrochloride.
LC/MS (method LC5): m/z=433.22; Rt=2.11 min
$^1$H-NMR: δ (ppm)=1.68-1.76 (m, 1H), 1.85-1.88 (m, 1H), 1.93-1.97 (m, 1H), 2.01-2.18 (m, 3H), 2.32 (s, 3H), 2.94 (br s, 4H), 3.59 (br s, 4H), 5.15 (br s, 1H), 5.71 (d, 1H), 5.93-5.97 (m, 1H), 6.66 (dd, 1H), 6.89 (dt, 1H), 7.16-7.22 (m, 2H), 7.33 (t, 1H), 7.53-7.59 (m, 2H), 9.04 (br d, 2H)

EXAMPLE 23

[1-Cyclohexyl-2-(5-fluoro-2-methyl-phenoxy)-1H-indol-3-yl]-piperazin-1-yl-methanone

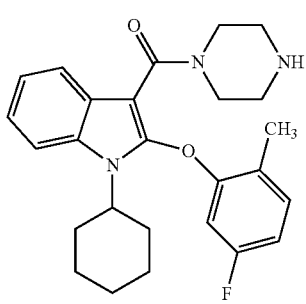

Step 1: 4-[1-Cyclohexyl-2-(5-fluoro-2-methyl-phenoxy)-1H-indole-3-carbonyl]-piperazine-1-carboxylic acid tert-butyl ester The compound of example 22, step 4 (66.0 mg, 124 µmol) was dissolved in ethanol (5 ml), and palladium on activated carbon (20 mg, 10%) was added. The mixture was hydrogenated overnight at room temperature and a hydrogen pressure of 4.5 bar. The mixture was filtered over celite and evaporated under reduced pressure to give 65.0 mg of the crude title compound.
LC/MS (method LC4): m/z=536

Step 2: [1-Cyclohexyl-2-(5-fluoro-2-methyl-phenoxy)-1H-indol-3-yl]-piperazin-1-yl-methanone The compound of step 1 (65.0 mg, 121 µmol) was reacted analogously as described in example 1, step 3. The obtained solid was purified by preparative HPLC, the eluate lyophilized overnight, the residue dissolved in a small quantity of MOH, mixed with hydrochloric acid (0.1 M) and lyophilized overnight. 43.6 mg of the title compound were obtained in the form of the [1-cyclohexyl-2-(5-fluoro-2-methyl-phenoxy)-1H-indol-3-yl]-piperazin-1-yl-methanone hydrochloride.
LC/MS (method LC6): m/z=435.23; Rt=3.04 min
$^1$H-NMR (400 MHz): δ (ppm)=1.22 (br t, 1H), 1.40 (br q, 2H), 1.66 (br d, 1H), 1.83 (br t, 4H), 2.07 (br q, 2H), 2.36 (s, 3H), 2.92 (br s, 4H), 3.58 (br s, 4H), 4.34-4.41 (m, 1H), 6.66 (dd, 1H), 6.90 (dt, 1H), 7.15-7.24 (m, 2H), 7.35 (t, 1H), 7.51 (d, 1H), 7.71 (d, 1H), 9.11 (br s, 2H)

EXAMPLE 24

(3-Hydroxymethyl-piperazin-1-yl)-(2-phenoxy-1-phenyl-1H-indol-3-yl)-methanone

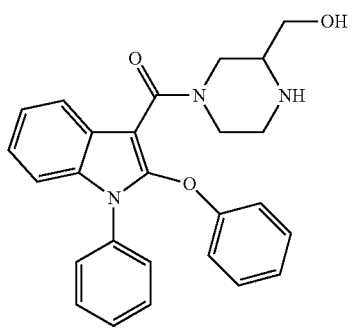

Step 1: 4-(2-Phenoxy-1-phenyl-1H-indole-3-carbonyl)-piperazine-1,2-dicarboxylic acid 1-tert-butyl ester 2-methyl ester The title compound was prepared from 2-phenoxy-1-phenyl-1H-indole-3-carboxylic acid (420 mg, 1.28 mmol) analogously as described in example 1, step 1. Yield: 564 mg.
LC/MS (method LC4): m/z=556

Step 2: (3-Hydroxymethyl-piperazin-1-yl)-(2-phenoxy-1-phenyl-1H-indol-3-yl)-methanone The compound of step 1 (100 mg, 0.18 mmol) was dissolved in THF (3.6 ml), lithium borohydride (11.8 mg, 0.54 mmol) was added, and the reaction was stirred at room temperature for 2 h. The mixture was partitioned between a saturated ammonium chloride solution and EA. The organic phase was washed with a saturated sodium hydrogencarbonate solution and water, dried over sodium sulfate and evaporated under reduced pressure. The residue was dissolved in DCM (20 ml), TFA (5 ml) was added, and the mixture was stirred at room temperature for 1 h. The solvents were evaporated and the obtained solid was purified by preparative HPLC. The eluate was lyophilized overnight, the residue dissolved in a small quantity of MOH, mixed with hydrochloric acid (0.1 M) and lyophilized overnight. 53 mg of the title compound were obtained in the form of the (3-hydroxymethyl-piperazin-1-yl)-(2-phenoxy-1-phenyl-1H-indol-3-yl)-methanone hydrochloride.

LC/MS (method LC5): m/z=427.19; Rt=1.92 min $^1$H-NMR: δ (ppm)=2.80 (m, 1H), 3.03 (m, 2H), 3.20 (m, 2H), 3.52 (m, 1H), 3.59 (m, 1H), 4.17 (m, 2H), 4.95 (m, 1H), 6.96 (m, 2H), 7.07 (m, 1H), 7.19-7.31 (m, 5H), 7.47 (m, 1H), 7.50-7.58 (m, 4H), 7.68 (m, 1H)

EXAMPLE 25

[2-(3-Fluoro-2-methyl-benzyl)-6-(2-hydroxy-ethoxy)-1-phenyl-1H-indol-3-yl]-piperazin-1-yl-methanone

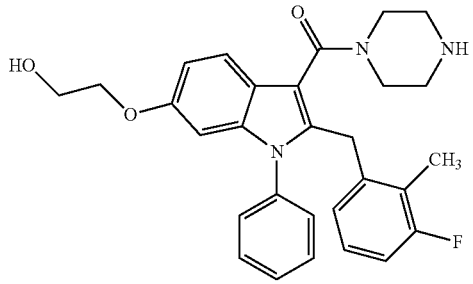

Step 1: 4-[6-(2-Benzyloxy-ethoxy)-2-(3-fluoro-2-methyl-benzyl)-1-phenyl-1H-indole-3-carbonyl]-piperazine-1-carboxylic acid tert-butyl ester The title compound was prepared analogously as described in example 12, step 1, using benzyl 2-bromo-ethyl ether. Yield: 26 mg.

LC/MS (method LC4): m/z=678

Step 2: [2-(3-Fluoro-2-methyl-benzyl)-6-(2-hydroxy-ethoxy)-1-phenyl-1H-indol-3-yl]-piperazin-1-yl-methanone The compound of step 1 (20 mg, 30 μmol) was dissolved in ethanol (5 ml), palladium on carbon (4 mg) was added, and the mixture was stirred under an atmosphere of hydrogen at a pressure of 1.5 bar at room temperature for 3 h. The mixture was filtered over a pad of celite and evaporated under reduced pressure. The residue was dissolved in DCM (20 ml), TFA (5 ml) was added, and the mixture was stirred at room temperature for 1 h. The solvents were evaporated and the obtained solid was purified by preparative HPLC. The eluate was lyophilized overnight, the residue dissolved in a small quantity of MOH, mixed with hydrochloric acid (0.1 M) and lyophilized overnight. 4 mg of the title compound were obtained in the form of the [2-(3-fluoro-2-methyl-benzyl)-6-(2-hydroxy-ethoxy)-1-phenyl-1H-indol-3-yl]-piperazin-1-yl-methanone hydrochloride.

LC/MS (method LC4): m/z=488.20; Rt=1.10 min

EXAMPLE 26

2-(5-Fluoro-2-methyl-phenoxy)-1-phenyl-3-(piperazine-1-carbonyl)-1H-indole-6-carbonitrile

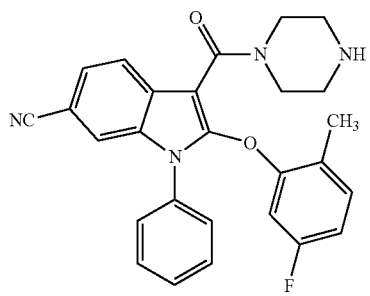

Step 1: 4-(6-Bromo-2-chloro-1-phenyl-1H-indole-3-carbonyl)-piperazine-1-carboxylic acid tert-butyl ester The title compound was prepared analogously as described in example 13, steps 1 to 5, starting with 6-bromo-1H-indole.

LC/MS (method LC4): m/z=518.84; Rt=1.95 min

Step 2: 4-[6-Bromo-2-(5-fluoro-2-methyl-phenoxy)-1-phenyl-1H-indole-3-carbonyl]-piperazine-1-carboxylic acid tert-butyl ester From the compound of step 1 (1 g, 1.93 mmol), the title compound was obtained analogously as described in example 1, step 2. Yield: 700 mg.

LC/MS (method LC4): m/z=609.20; Rt=2.10 min

Step 3: 4-[6-Cyano-2-(5-fluoro-2-methyl-phenoxy)-1-phenyl-1H-indole-3-carbonyl]-piperazine-1-carboxylic acid tert-butyl ester A mixture of the compound of step 2 (350 mg, 0.58 mmol), zinc cyanide (135 mg, 1.15 mmol) and tetrakis(triphenylphosphin)palladium(0) (133 mg, 0.12 mmol) in DMF (8 ml) was heated to 80° C. for 1 h. After cooling to room temperature, the mixture was partitioned between water and EA and the aqueous phase extracted with EA. The combined organic layers were dried over sodium sulfate, filtered and concentrated. The residue was purified by preparative HPLC and lyophilized overnight. 151 mg of the title compound were obtained.

LC/MS (method LC4): m/z=555

$^1$H-NMR: δ (ppm)=1.40 (m, 9H), 2.10 (m, 3H), 3.19 (m, 4H), 3.45 (m, 4H), 6.87 (m, 1H), 7.01 (m, 1H), 7.21 (m, 1H), 7.50-7.64 (m, 7H), 7.72 (m, 1H)

Step 4: 2-(5-Fluoro-2-methyl-phenoxy)-1-phenyl-3-(piperazine-1-carbonyl)-1H-indole-6-carbonitrile The compound of step 3 (20 mg, 36 μmol) was dissolved in DCM (6 ml), TFA (2 ml) was added, and the mixture was stirred at room temperature for 1 h. The solvents were evaporated. The residue was dissolved in a small quantity of MOH, mixed with hydrochloric acid (0.1 M) and lyophilized overnight. 11 mg of the title compound were obtained in the form of the 2-(5-fluoro-2-methyl-phenoxy)-1-phenyl-3-(piperazine-1-carbonyl)-1H-indole-6-carbonitrile hydrochloride.

LC/MS (method LC8): m/z=454.18; Rt=2.73 min $^1$H-NMR: δ (ppm)=2.13 (m, 3H), 2.99 (m, 4H), 3.68 (m, 4H), 6.88 (m, 1H), 6.98 (m, 1H), 7.21 (m, 1H), 7.52 (m, 1H), 7.56-7.67 (m, 6H), 7.80 (m, 1H)

EXAMPLE 27

2-(5-Fluoro-2-methyl-phenoxy)-1-phenyl-3-(piperazine-1-carbonyl)-1H-indole-6-carboxylic acid methyl ester

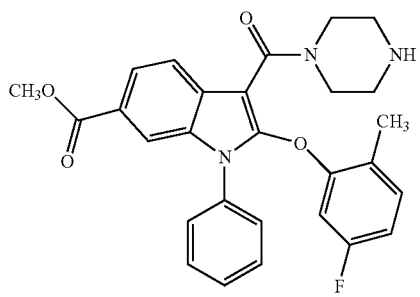

Step 1: 3-(4-tert-Butoxycarbonyl-piperazine-1-carbonyl)-2-(5-fluoro-2-methyl-phenoxy)-1-phenyl-1H-indole-6-carboxylic acid methyl ester A mixture of the compound of example 26, step 2, (100 mg, 0.16 mmol), triethylamine (166 mg, 1.6 mmol), 1,3-bis(diphenylphosphino)propane (7.4 mg, 18 μmol) and palladium(II) acetate (3.7 mg, 16 μmol) in DMF (8 ml) and MOH (2 ml) was heated to 120° C. for 2 h under an atmosphere of carbon monoxide. After cooling to room temperature, the mixture was partitioned between water and EA. The aqueous phase was extracted with EA. The combined organic layers were dried over sodium sulfate, filtered, and concentrated. The residue was purified by silica gel chromatography (EA/HEP). 30 mg of the title compound were obtained.

LC/MS (method LC4): m/z=588

Step 2: 2-(5-Fluoro-2-methyl-phenoxy)-1-phenyl-3-(piperazine-1-carbonyl)-1H-indole-6-carboxylic acid methyl ester From the compound of step 1 (10 mg, 17 μmol), the title compound was prepared analogously as described in example 26, step 4, and obtained in the form of the 2-(5-fluoro-2-methyl-phenoxy)-1-phenyl-3-(piperazine-1-carbonyl)-1H-indole-6-carboxylic acid methyl ester hydrochloride. Yield: 8.8 mg.

LC/MS (method LC7): m/z=487.19; Rt=1.50 min $^1$H-NMR: δ (ppm)=1.12 (m, 3H), 2.99 (m, 4H), 3.70 (m, 4H), 3.82 (m, 3H), 6.87 (m, 1H), 6.97 (m, 1H), 7.21 (m, 1H), 7.55 (m, 1H), 7.58-7.64 (m, 4H), 7.73 (m, 2H), 7.87 (m, 1H)

EXAMPLE 28

2-(5-Fluoro-2-methyl-phenoxy)-1-phenyl-3-(piperazine-1-carbonyl)-1H-indole-6-carboxylic acid

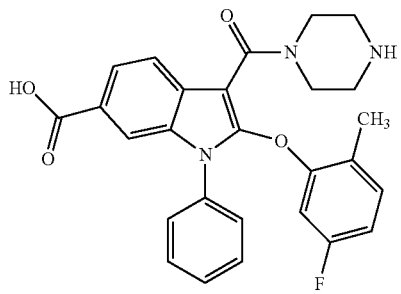

The compound of example 27, step 1 (18 mg, 30.6 μmol) was dissolved in MOH (1 ml), a 2 N sodium hydroxide solution (300 μl) was added, and the mixture was stirred at 40° C. for 3 h. The mixture was diluted with EA and washed with a saturated solution of ammonium chloride. The organic layer was dried over sodium sulfate and concentrated. The residue was dissolved in DCM (1 ml), TFA (0.3 ml) was added, and the mixture was stirred at room temperature for 1 h. The solvents were evaporated and the obtained solid residue was purified by preparative HPLC. The eluate was lyophilized overnight. The residue was dissolved in a small quantity of MOH, mixed with hydrochloric acid (0.1 M) and lyophilized overnight. 3.6 mg of the title compound were obtained in the form of the 2-(5-fluoro-2-methyl-phenoxy)-1-phenyl-3-(piperazine-1-carbonyl)-1H-indole-6-carboxylic acid hydrochloride.

LC/MS (method LC4): m/z=474.20; Rt=1.11 min $^1$H-NMR: δ (ppm)=2.14 (m, 3H), 3.12 (m, 4H), 3.86 (m, 4H), 6.69-6.80 (m, 2H), 7.15 (m, 1H), 7.48-7.60 (5H), 7.71 (m, 1H), 7.89 (m, 1H), 7.95 (m, 1H)

EXAMPLE 29

2-(5-Fluoro-2-methyl-phenoxy)-1-phenyl-3-(piperazine-1-carbonyl)-1H-indole-5-carboxylic acid amide

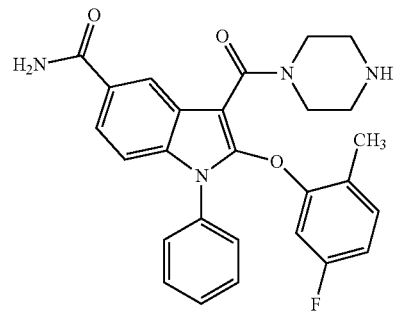

A mixture of 4-[5-cyano-2-(5-fluoro-2-methyl-phenoxy)-1-phenyl-1H-indole-3-carbonyl]-piperazine-1-carboxylic acid tert-butyl ester (70 mg, 0.126 mmol), acetamide (31.5 mg, 0.53 mmol) and palladium(II) chloride (2.2 mg, 13 μmol) in THF (4 ml) and water (1.4 ml) was stirred at room temperature for 30 h. After addition of water, the mixture was extracted with EA. The combined organic layers were dried over sodium sulfate and concentrated. The residue was dissolved in DCM (1 ml), TFA (0.3 ml) was added, and the mixture was stirred at room temperature for 1 h. The solvents were evaporated and the obtained solid was purified by preparative HPLC. The eluate was lyophilized overnight. The residue was dissolved in a small quantity of MOH, mixed with hydrochloric acid (0.1 M) and lyophilized overnight. 13.5 mg of the title compound were obtained in the form of the 2-(5-fluoro-2-methyl-phenoxy)-1-phenyl-3-(piperazine-1-carbonyl)-1H-indole-5-carboxylic acid amide hydrochloride.

LC/MS (method LC4): m/z=473.20; Rt=1.13 min $^1$H-NMR: δ (ppm)=2.15 (m, 3H), 3.17 (m, 4H), 3.88 (m, 4H), 6.67 (m, 1H), 6.74 (m, 1H), 7.13 (m, 1H), 7.28 (m, 1H), 7.45-7.58 (m, 5H), 7.80 (1), 8.25 (m, 1H)

EXAMPLE 30

[2-(5-Fluoro-2-methyl-phenoxy)-1-phenyl-3-(piperazine-1-carbonyl)-1H-indol-6-yloxy]-acetic acid

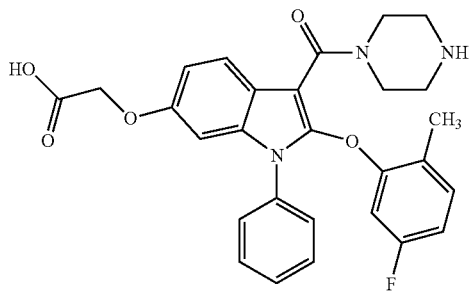

Step 1: 4-[6-tert-Butoxycarbonylmethoxy-2-(5-fluoro-2-methyl-phenoxy)-1-phenyl-1H-indole-3-carbonyl]-piperazine-1-carboxylic acid tert-butyl ester The title compound was prepared analogously as described in example 12, step 1, using tert-butyl bromoacetate.

LC/MS (method LC4): m/z=660

Step 2: [2-(5-Fluoro-2-methyl-phenoxy)-1-phenyl-3-(piperazine-1-carbonyl)-1H-indol-6-yloxy]-acetic acid The compound of step 1 (88 mg, 133 μmol) was dissolved in DCM (20 ml), TFA (5 ml) was added, and the mixture was stirred at room temperature for 1 h. The solvents were evaporated and the obtained solid was purified by preparative HPLC. The eluate was lyophilized overnight. The residue was dissolved in a small quantity of MOH, mixed with hydrochloric acid (0.1 M) and lyophilized overnight. 45 mg of the title compound were obtained in the form of the [2-(5-fluoro-2-methyl-phenoxy)-1-phenyl-3-(piperazine-1-carbonyl)-1H-indol-6-yloxy]-acetic acid hydrochloride.

LC/MS (method LC6): m/z=503.19; Rt=2.67 min $^1$H-NMR: δ (ppm)=2.09 (m, 3H), 3.03 (m, 4H), 3.18 (m, 4H), 4.13 (m, 2H), 6.66 (m, 2H), 6.79 (m, 1H), 6.93 (m, 1H), 7.16 (m, 1H), 7.43-7.60 (m, 6H), 8.92 (m, 1H)

EXAMPLE 31

[2-(5-Fluoro-2-methyl-phenoxy)-6-methanesulfonyl-1-phenyl-1H-indol-3-yl]-piperazin-1-yl-methanone

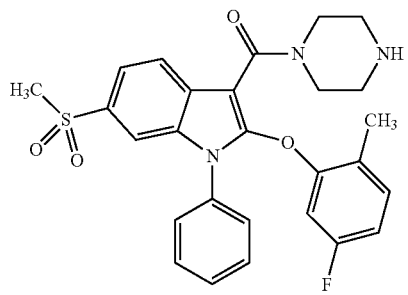

Step 1: 2-Chloro-6-methanesulfonyl-1-phenyl-1H-indole-3-carbaldehyde

The title compound was prepared analogously as described in example 13, steps 1 to 3, starting with 6-methanesulfonyl-1H-indole.

LC/MS (method LC4): m/z=472; Rt=1.40 min

Step 2: [2-(5-Fluoro-2-methyl-phenoxy)-6-methanesulfonyl-1-phenyl-1H-indol-3-yl]-piperazin-1-yl-methanone From the compound of step 1, the title compound was prepared analogously as described in example 1, step 2. Yield: 25 mg.

LC/MS (method LC4): m/z=424

Step 3: 2-(5-Fluoro-2-methyl-phenoxy)-6-methanesulfonyl-1-phenyl-1H-indole-3-carboxylic acid From the compound of step 2, the title compound was prepared analogously as described in example 7, step 3. Yield: 23 mg.

LC/MS (method LC4): m/z=440

Step 4: 4-[2-(5-Fluoro-2-methyl-phenoxy)-6-methanesulfonyl-1-phenyl-1H-indole-3-carbonyl]-piperazine-1-carboxylic acid tert-butyl ester From the compound of step 3, the title compound was prepared analogously as described in example 17, step 1. Yield: 30 mg.

LC/MS (method LC4): m/z=608

Step 5: [2-(5-Fluoro-2-methyl-phenoxy)-6-methanesulfonyl-1-phenyl-1H-indol-3-yl]-piperazin-1-yl-methanone From the compound of step 4 (30 mg, 49 μmol), the title compound was prepared analogously as described in example 26, step 4, and obtained in the form of the [2-(5-fluoro-2-methyl-phenoxy)-6-methanesulfonyl-1-phenyl-1H-indol-3-yl]-piperazin-1-yl-methanone hydrochloride. Yield: 9 mg.

LC/MS (method LC7): m/z=507.16; Rt=2.55 min
¹H-NMR: δ (ppm)=2.11 (m, 3H), 3.01 (m, 4H), 3.20 (m, 3H), 3.69 (m, 4H), 6.88 (m, 1H), 6.98 (m, 1H), 7.22 (m, 1H), 7.55 (m, 1H), 7.62 (m, 5H), 7.78 (m, 1H), 7.87 (m, 1H)

EXAMPLE 32

[1-Cyclohexyl-2-(3-fluoro-2-methyl-benzyl)-1H-indol-3-yl]-piperazin-1-yl-methanone

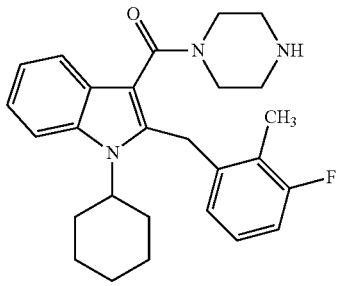

Step 1: 4-[1-Cyclohex-2-enyl-2-(3-fluoro-2-methyl-benzyl)-1H-indole-3-carbonyl]-piperazine-1-carboxylic acid tert-butyl ester From the compound of example 22, step 3, (90.0 mg, 203 µmol), the title compound was prepared analogously as described in example 13, step 6. Yield: 100 mg.
LC/MS (method LC4): m/z=532

Step 2: [1-Cyclohexyl-2-(3-fluoro-2-methyl-benzyl)-1H-indol-3-yl]-piperazin-1-yl-methanone From the compound of step 1 (90.0 mg, 169 µmol), the title compound was prepared analogously as described in example 23, steps 1 and 2, and obtained in the form of the [1-cyclohexyl-2-(3-fluoro-2-methyl-benzyl)-1H-indol-3-yl]-piperazin-1-yl-methanone hydrochloride. Yield: 30 mg.
LC/MS (method LC4): m/z=433.25; Rt=2.20 min
¹H-NMR: δ (ppm)=1.08 (m, 2H), 1.26 (m, 1H), 1.43 (m, 2H), 1.58 (m, 1H), 1.74 (m, 2H), 2.16 (m, 2H), 2.31 (m, 3H), 2.95 (m, 2H), 3.18 (m, 2H), 3.64 (m, 2H), 3.69 (m, 2H), 3.85 (m, 1H), 4.30 (m, 1H), 6.58 (m, 1H), 6.95-7.10 (m, 2H), 7.17 (m, 2H), 7.53 (m, 1H), 7.70 (m, 1H)

EXAMPLE 33

[2-(3-Fluoro-2-methyl-benzyl)-1-(tetrahydro-2H-pyran-4-yl)-1H-indol-3-yl]-piperazin-1-yl-methanone

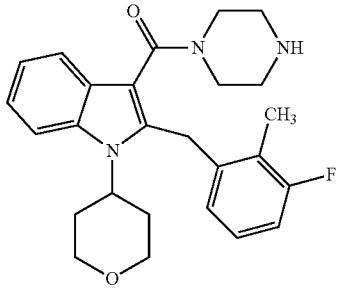

The title compound was prepared analogously as described in the examples above, starting with the reaction of 1 equivalent each of 2-chloro-1H-indole-3-carbaldehyde and 4-iodo-tetrahydro-2H-pyran in the presence of potassium carbonate as a base in DMF at 100° C. for 4 h and purification of the obtained 2-chloro-1-(tetrahydro-2H-pyran-4-yl)-1H-indole-3-carbaldehyde by preparative HPLC, and obtained in the form of the [2-(3-fluoro-2-methyl-benzyl)-1-(tetrahydro-2H-pyran-4-yl)-1H-indol-3-yl]-piperazin-1-yl-methanone trifluoroacetic acid salt.
LC/MS (method LC8): m/z=435.23; Rt=2.65 min

EXAMPLE 34

[1-Cyclopentyl-2-(3-fluoro-2-methyl-benzyl)-1H-indol-3-yl]-piperazin-1-yl-methanone

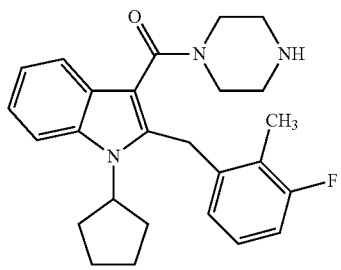

The title compound was prepared analogously as described in the examples above, starting with the reaction of 1 equivalent each of 2-chloro-1H-indole-3-carbaldehyde and iodocyclopentane in the presence of potassium carbonate as a base in DMF at 100° C. for 2 h and purification of the obtained 2-chloro-1-cyclopentyl-1H-indole-3-carbaldehyde by preparative HPLC, and obtained in the form of the [1-cyclopentyl-2-(3-fluoro-2-methyl-benzyl)-1H-indol-3-yl]-piperazin-1-yl-methanone trifluoroacetic acid salt.
LC/MS (method LC8): m/z=419.24; Rt=2.94 min Analogously as described in the examples above, the compounds of the formula Id listed in table 1 were prepared and obtained in the form of their trifluoroacetic acid salt or hydrochloride, respectively. The compounds can be named as [2-($R^{20}$-oxy)-1-$R^{30}$-(4-$R^{40}$- and/or 5-$R^{40}$- and/or 6-$R^{40}$- and/or 7-$R^{40}$)-1H-indol-3-yl]-piperazin-1-yl-methanone in case the group A is O, or [2-($R^{20}$-methyl)-1-$R^{30}$-(4-$R^{40}$- and/or 5-$R^{40}$- and/or 6-$R^{40}$- and/or 7-$R^{40}$)-1H-indol-3-yl]-piperazin-1-yl-methanone in case the group A is $CH_2$, allowing for modifications due to the rules of nomenclature such as the designation of the group $R^{20}$-methyl as benzyl group, for example.

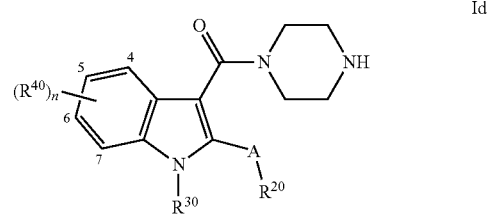

Id

TABLE 1

Example compounds of the formula Id

| Example no. | A | R$^{20}$ | R$^{30}$ | Substituents R$^{40}$ and their positions | Rt (min) | MS (m/z) | LC/MS method |
|---|---|---|---|---|---|---|---|
| 35 (1) | O | phenyl | phenyl | 6-chloro | 1.47 | 431.14 | LC1 |
| 36 (1) | O | 2-methyl-phenyl | phenyl | 6-methoxy | 1.36 | 441.21 | LC1 |
| 37 (1) | O | 5-fluoro-2-methyl-phenyl | phenyl | 6-methoxy | 1.40 | 459.20 | LC1 |
| 38 (1) | O | 3-fluoro-2-methyl-phenyl | phenyl | 6-methoxy | 1.40 | 459.20 | LC1 |
| 39 (1) | CH$_2$ | 3-fluoro-2-methyl-phenyl | phenyl | 7-fluoro | 1.65 | 445.20 | LC2 |
| 40 (1) | CH$_2$ | 3-fluoro-2-methyl-phenyl | phenyl | 6-methoxy | 1.63 | 457.22 | LC2 |
| 41 (1) | O | 3-fluoro-2-methyl-phenyl | phenyl | 7-fluoro | 1.63 | 447.18 | LC2 |
| 42 (1) | O | 5-fluoro-2-methyl-phenyl | phenyl | 7-fluoro | 1.63 | 447.18 | LC2 |
| 43 (1) | O | 3-fluoro-2-methyl-phenyl | phenyl | 5-methoxy | 1.62 | 459.20 | LC2 |
| 44 (1) | O | 5-fluoro-2-methyl-phenyl | phenyl | 5-methoxy | 1.43 | 459.20 | LC1 |
| 45 (2) | CH$_2$ | 3-fluoro-2-methyl-phenyl | phenyl | 5-hydroxy | 1.34 | 443.20 | LC1 |
| 46 (1) | O | 5-fluoro-2-methyl-phenyl | 4-fluoro-phenyl | 6-methoxy | 1.42 | 477.19 | LC1 |
| 47 (1) | O | 3-fluoro-2-methyl-phenyl | 4-fluoro-phenyl | 6-methoxy | 1.43 | 477.19 | LC1 |
| 48 (2) | O | 5-fluoro-2-methyl-phenyl | 4-fluoro-phenyl | 6-hydroxy | 1.48 | 463.17 | LC3 |
| 49 (2) | CH$_2$ | 3-fluoro-2-methyl-phenyl | phenyl | 5-hydroxy | 1.35 | 443.20 | LC1 |
| 50 (2) | CH$_2$ | 3-fluoro-2-methyl-phenyl | phenyl | 6-hydroxy | 1.29 | 443.20 | LC1 |
| 51 (2) | O | 5-fluoro-2-methyl-phenyl | phenyl | 5-hydroxy | 1.32 | 445.18 | LC1 |
| 52 (1) | O | 5-fluoro-2-methyl-phenyl | phenyl | 5,6-dimethoxy | 1.38 | 489.21 | LC1 |
| 53 (2) | O | 5-fluoro-2-methyl-phenyl | phenyl | 5-bromo | 1.50 | 507.10 | LC1 |
| 54 (2) | O | 5-fluoro-2-methyl-phenyl | phenyl | 6-methoxy | 1.40 | 459.20 | LC1 |
| 55 (2) | CH$_2$ | 3-fluoro-2-methyl-phenyl | phenyl | 4-methyl, 5-methoxy | 1.46 | 471.23 | LC1 |
| 56 (2) | CH$_2$ | 3-fluoro-2-methyl-phenyl | phenyl | 4-methyl, 5-hydroxy | 1.31 | 457.22 | LC1 |
| 57 (2) | CH$_2$ | 3-fluoro-2-methyl-phenyl | phenyl | 6-(2-phenoxy-ethoxy) | 1.64 | 563.26 | LC1 |
| 58 (2) | O | 5-fluoro-methyl-phenyl | phenyl | 6-bromo | 3.09 | 507.10 | LC6 |
| 59 (2) | O | 5-fluoro-methyl-phenyl | phenyl | 5-cyano | 2.76 | 454.18 | LC8 |
| 60 (1) | CH$_2$ | 2-chloro-6-fluoro-phenyl | phenyl | 5-hydroxy | 2.60 | 463.15 | LC5 |
| 61 (1) | CH$_2$ | 2-fluoro-6-methyl-phenyl | phenyl | 5-hydroxy | 2.60 | 443.20 | LC5 |
| 62 (1) | CH$_2$ | 3-fluoro-2-methyl-phenyl | phenyl | 5-hydroxy, 6-(3-fluoro-2-methyl-benzyl) | 3.19 | 565.25 | LC5 |
| 63 (2) | CH$_2$ | 3-fluoro-2-methyl-phenyl | phenyl | 6-methanesulfonyl | 1.13 | 506.20 | LC4 |
| 64 (1) | O | 5-fluoro-2-methyl-phenyl | phenyl | 5-hydroxy, 6-chloro | 2.78 | 479.14 | LC5 |
| 65 (2) | O | 5-fluoro-2-methyl-phenyl | phenyl | 6-carbamoyl | 2.54 | 472.19 | LC6 |
| 66 (3) | O | 5-fluoro-2-methyl-phenyl | phenyl | 6-(2-dimethyl-amino-ethoxy) | 2.40 | 516.25 | LC6 |
| 67 (1) | CH$_2$ | 2-chloro-6-methyl-phenyl | phenyl | 5-hydroxy | 2.90 | 459.17 | LC8 |
| 68 (1) | O | 2,6-dimethyl-phenyl | phenyl | 5-hydroxy, 6-chloro | 3.70 | 475.17 | LC9 |
| 69 (1) | O | 5-fluoro-2-methyl-phenyl | phenyl | 6-carboxy | 2.65 | 473.18 | LC6 |

TABLE 1-continued

Example compounds of the formula Id

| Example no. | A | $R^{20}$ | $R^{30}$ | Substituents $R^{40}$ and their positions | Rt (min) | MS (m/z) | LC/MS method |
|---|---|---|---|---|---|---|---|
| 70 (1) | O | 3-fluoro-2,6-dimethyl-phenyl | phenyl | 6-hydroxy | 2.77 | 459.20 | LC8 |

(1) Obtained in the form of the trifluoroacetic acid salt
(2) Obtained in the form of the hydrochloride
(3) Obtained in the form of the dihydrochloride Analogously as described in the examples above, the compounds of the formula Ie listed in table 2 were prepared and obtained in the form of their trifluoroacetic acid salt unless specified otherwise. The compounds can be named as [2-($R^{20}$-oxy)-1-$R^{30}$-1H-indol-3-yl]-piperazin-1-yl-methanone in case the group A is O, or [2-($R^{20}$-sulfanyl)-1-$R^{30}$-1H-indol-3-yl]-piperazin-1-yl-methanone in case the group A is S, or [2-($R^{20}$-methyl)-1-$R^{30}$-1H-indol-3-yl]-piperazin-1-yl-methanone in case the group A is $CH_2$, allowing for modifications due to the rules of nomenclature such as the designation of the group $R^{20}$-methyl as benzyl group, for example.

TABLE 2

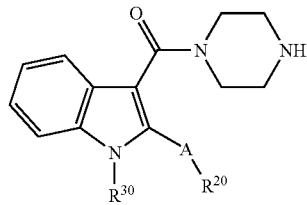

Ie

Example compound of the formula Ie

| Example no. | A | $R^{20}$ | $R^{30}$ | Rt (min) | MS (m/z) | LC/MS method |
|---|---|---|---|---|---|---|
| 71 | O | 3-methyl-phenyl | phenyl | 1.37 | 411.19 | LC1 |
| 72 | O | 3-fluoro-phenyl | phenyl | 1.35 | 415.17 | LC1 |
| 73 | O | 4-fluoro-phenyl | phenyl | 1.35 | 415.17 | LC1 |
| 74 | O | 2-fluoro-phenyl | phenyl | 1.35 | 415.17 | LC1 |
| 75 | $CH_2$ | phenyl | phenyl | 1.53 | 395.20 | LC2 |
| 76 | O | 2-ethyl-phenyl | phenyl | 1.70 | 425.21 | LC2 |
| 77 | O | 2-isopropyl-phenyl | phenyl | 1.50 | 439.23 | LC1 |
| 78 | O | 2-methoxy-phenyl | phenyl | 1.32 | 427.19 | LC1 |
| 79 | O | 2,6-dimethyl-phenyl | phenyl | 1.42 | 425.21 | LC2 |
| 80 | O | 2-chloro-phenyl | phenyl | 1.31 | 431.14 | LC1 |
| 81 | $CH_2$ | 2-methyl-phenyl | phenyl | 1.24 | 410.25 | LC4 |
| 82 | $CH_2$ | 2-fluoro-phenyl | phenyl | 1.23 | 414.20 | LC4 |
| 83 | $CH_2$ | 3-methyl-phenyl | phenyl | 1.40 | 409.22 | LC1 |
| 84 | O | 3-trifluoromethyl-phenyl | phenyl | 1.57 | 465.17 | LC3 |
| 85 | O | 3-chloro-phenyl | phenyl | 1.24 | 432.20 | LC4 |
| 86 | S | phenyl | phenyl | 1.35 | 413.16 | LC1 |
| 87 | $CH_2$ | 2,6-difluoro-phenyl | phenyl | 1.37 | 431.18 | LC1 |
| 88 | $CH_2$ | 2-chloro-phenyl | phenyl | 1.41 | 429.16 | LC1 |
| 89 | O | phenyl | 3-(3-methoxy-propoxy)-phenyl | 1.60 | 485.23 | LC2 |
| 90 | O | 2-methyl-phenyl | 3-(3-methoxy-propoxy)-phenyl | 1.65 | 499.25 | LC2 |
| 91 | O | phenyl | 4-fluoro-phenyl | 1.53 | 415.17 | LC2 |
| 92 | O | 2-methyl-phenyl | 2-methoxy-phenyl | 1.55 | 441.21 | LC2 |
| 93 | O | phenyl | 2-methoxy-phenyl | 1.49 | 427.19 | LC2 |
| 94 (1) | O | 2-methyl-phenyl | pyridin-3-yl | 1.15 | 412.19 | LC2 |
| 95 (1) | O | phenyl | pyridin-3-yl | 1.07 | 398.17 | LC2 |
| 96 | O | 2-methyl-phenyl | 4-fluoro-phenyl | 1.63 | 429.19 | LC2 |
| 97 | O | 2-methyl-phenyl | 2-(3-methoxy-propoxy)-phenyl | 1.60 | 499.25 | LC2 |
| 98 | O | phenyl | 2-(3-methoxy-propoxy)-phenyl | 1.57 | 485.23 | LC2 |
| 99 | O | 3-fluoro-2-methyl-phenyl | phenyl | 1.44 | 429.19 | LC1 |
| 100 | S | 3-fluoro-phenyl | phenyl | 1.47 | 431.15 | LC1 |
| 101 | S | 2-fluoro-phenyl | phenyl | 1.41 | 431.15 | LC1 |
| 102 | O | 2-fluoro-6-methyl-phenyl | phenyl | 1.48 | 429.19 | LC1 |
| 103 | O | 2-fluoro-phenyl | 2-(3-methoxy- | 1.36 | 504.20 | LC4 |

TABLE 2-continued

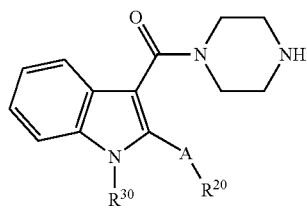

Example compound of the formula Ie

| Example no. | A | $R^{20}$ | $R^{30}$ | Rt (min) | MS (m/z) | LC/MS method |
|---|---|---|---|---|---|---|
| 104 (1) | O | 2-methyl-phenyl | propoxy)-phenyl pyridin-2-yl | 1.23 | 412.19 | LC1 |
| 105 (1) | O | phenyl | pyridin-2-yl | 1.20 | 398.17 | LC1 |
| 106 | O | 2,3-difluoro-phenyl | phenyl | 1.38 | 433.16 | LC1 |
| 107 | O | 2,5-difluoro-phenyl | phenyl | 1.38 | 433.16 | LC1 |
| 108 | S | 2-methyl-phenyl | phenyl | 1.42 | 427.17 | LC1 |
| 109 | O | 5-fluoro-2-methyl-phenyl | thiophen-3-yl | 1.41 | 435.14 | LC1 |
| 110 | O | 3,5-difluoro-2-methyl-phenyl | phenyl | 1.47 | 447.18 | LC1 |
| 111 (1) | O | 3-fluoro-2-methyl-phenyl | 6-methoxy-pyridin-3-yl | 1.37 | 460.19 | LC1 |
| 112 (1) | O | 5-fluoro-2-methyl-phenyl | 6-methoxy-pyridin-3-yl | 1.39 | 460.19 | LC1 |
| 113 | $CH_2$ | 2-methyl-phenyl | thiophen-3-yl | 1.42 | 415.17 | LC1 |
| 114 (1) | $CH_2$ | 3-fluoro-2-methyl-phenyl | 6-methoxy-pyridin-3-yl | 1.37 | 458.21 | LC1 |
| 115 | $CH_2$ | 3-fluoro-2-methyl-phenyl | 2-(2-methoxy-ethoxy)-phenyl | 1.62 | 501.24 | LC2 |
| 116 (2) | $CH_2$ | 3-fluoro-2-methyl-phenyl | 6-hydroxy-pyridin-3-yl | 1.03 | 444.20 | LC2 |
| 117 | O | 5-fluoro-2-methyl-phenyl | 3-methoxy-phenyl | 1.32 | 460.19 | LC1 |
| 118 | O | 5-fluoro-2-methyl-phenyl | 3-hydroxy-phenyl | 1.00 | 446.18 | LC1 |
| 119 | O | 5-fluoro-2-methyl-phenyl | 4-methyl-phenyl | 3.01 | 443.20 | LC6 |
| 120 | O | 5-fluoro-2-methyl-phenyl | tetrahydro-2H-pyran-4-yl | 2.57 | 437.52 | LC8 |
| 121 | O | 5-fluoro-2-methyl-phenyl | cyclopentyl | 2.96 | 421.22 | LC8 |
| 122 | O | 2,6-dimethyl-phenyl | cyclopentyl | 2.96 | 417.24 | LC8 |

(1) Obtained in the form of the bis(trifluoroacetic acid salt)
(2) Obtained in the form of the trifluoroacetic acid salt; from 6-methoxy-pyridine-3-boronic acid as starting compound through cleavage of the methoxy group.

Analogously as described in the examples above, the compounds of the formula If listed in table 3 were prepared and obtained in the form of their trifluoroacetic acid salt or hydrochloride, respectively. The compounds can be named as [2-phenoxy-1-phenyl-1H-indol-3-yl]-$R^{100}$-methanone.

TABLE 3

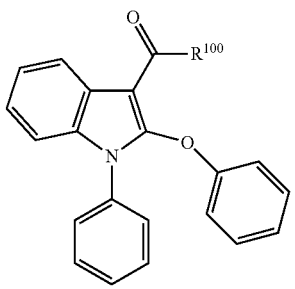

Example compounds of the formula If

| Example no. | $R^{100}$ | Rt (min) | MS (m/z) | LC/MS method |
|---|---|---|---|---|
| 123 (1) | 3-methyl-piperazin-1-yl | 1.36 | 411.19 | LC1 |

TABLE 3-continued

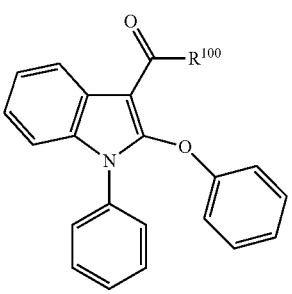

Example compounds of the formula If

| Example no. | $R^{100}$ | Rt (min) | MS (m/z) | LC/MS method |
|---|---|---|---|---|
| 124 (1) | 3,3-dimethyl-piperazin-1-yl | 2.00 | 425.21 | LC5 |
| 125 (1) | 3-butyl-piperazin-1-yl | 2.15 | 453.24 | LC5 |

TABLE 3-continued

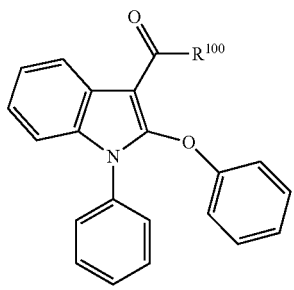

Example compounds of the formula If

| Example no. | R$^{100}$ | Rt (min) | MS (m/z) | LC/MS method |
|---|---|---|---|---|
| 126 (1) | 2-benzyl-piperazin-1-yl | 3.12 | 487.23 | LC8 |

(1) Obtained in the form of the trifluoroacetic acid salt
(2) Obtained in the form of the hydrochloride

EXAMPLE 127

[6-Chloro-2-(5-fluoro-2-methyl-phenoxy)-5-hydroxy-1-phenyl-1H-indol-3-yl]-((S)-3-methyl-piperazin-1-yl)-methanone

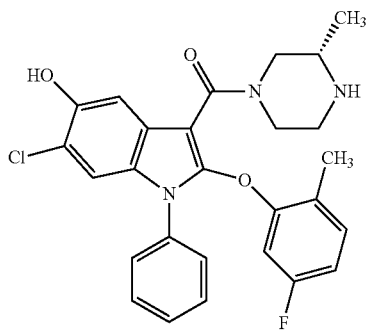

The title compound was prepared analogously as described in the examples above and obtained in the form of the [6-chloro-2-(5-fluoro-2-methyl-phenoxy)-5-hydroxy-1-phenyl-1H-indol-3-yl]-((S)-3-methyl-piperazin-1-yl)-methanone trifluoroacetic acid salt.

LC/MS (method LC6): m/z=493.16; Rt=2.93 min

Pharmacological Tests

A) Inhibition of Renin

The renin-inhibiting activity of compounds of the invention was demonstrated in an in vitro test in which a non-endogenous fluorogenic peptide substrate is cleaved by renin specifically at the Leu-Val bond which corresponds to the cleavage site of angiotensinogen.

Recombinant human renin (Cayman, no. 10006217) at a concentration of 5 nM was incubated with the test compounds at various concentrations and the synthetic substrate Dabcyl-γ-Abu-Ile-His-Pro-Phe-His-Leu-Val-Ile-His-Thr-EDANS (Bachem, no. M-2050; Dabcyl means the 4-(4-dimethylamino-phenylazo)-benzoyl group and EDANS means the amide with 5-[(2-aminoethyl)amino]-naphthalene-1-sulfonic acid) at a concentration of 10 μM for 2 h at room temperature in 0.05 M Tris buffer (pH 8) containing 0.1 M NaCl, 2.5 mM EDTA and 1.25 mg/ml bovine serum albumin. The increase in fluorescence, which is due to fluorescence resonance energy transfer, was recorded at an excitation wavelength of 330 nm and an emission wavelength of 485 nm in a microplate spectrofluorometer. Inhibitory concentrations IC$_{50}$ were calculated from the percentage of inhibition of renin activity as a function of the concentration of the test compound. In this test, the example compounds generally inhibited renin with an IC$_{50}$ value of less than about 10 micromol/l (10 μM). Representative IC$_{50}$ values, which were determined with the compounds in the form of the obtained salt indicated in the examples above, are listed in table 4.

TABLE 4

IC$_{50}$ values for inhibition of renin (fluorogenic peptide substrate)

| Compound of example no. | IC$_{50}$ (μM) |
|---|---|
| 3 | 3.2 |
| 5 | 3.4 |
| 17 | 0.018 |
| 22 | 0.0072 |
| 24 | 1.6 |
| 25 | 0.031 |
| 29 | 0.0055 |
| 30 | 0.13 |
| 32 | 0.034 |
| 33 | 0.75 |
| 35 | 0.54 |
| 39 | 0.084 |
| 40 | 0.012 |
| 48 | 0.018 |
| 56 | 0.0019 |
| 57 | 0.024 |
| 62 | 0.43 |
| 63 | 0.044 |
| 66 | 0.029 |
| 89 | 0.76 |
| 91 | 0.71 |
| 108 | 0.071 |
| 113 | 0.23 |
| 116 | 9.4 |
| 123 | 6.5 |
| 126 | 4.5 |

B) Inhibition of Renin in Human Plasma

The renin-inhibiting activity of compounds of the invention was also demonstrated in an in vitro test in the presence of human plasma. The procedure followed the procedure described in pharmacological test A except that human recombinant renin at a concentration of 30 nM was incubated with the test compounds at various concentrations and the fluorogenic substrate Dabcyl-γ-Abu-Ile-His-Pro-Phe-His-Leu-Val-Ile-His-Thr-EDANS at a concentration of 25 μM for 30 min at 37° C. and 30 min at room temperature in human plasma (Innovative Research, pooled normal human plasma collected on EDTA K3 as an anticoagulant, no. IPLA-5).

C) Antihypertensive Activity

The in vivo antihypertensive activity of compounds of the invention can be demonstrated in doubly transgenic mice overexpressing both human renin and angiotensinogen genes (dTghRenhAgt mice; cf. D. C. Merrill et al., J. Clin. Invest. 97 (1996), 1047; R. L. Davisson et al., J. Clin. Invest. 99 (1997), 1258; J. L. Lavoie et al., Acta Physiol. Scand. 81 (2004), 571; available by breeding strains carrying the human renin transgene and the human angiotensinogen transgene, respectively). Briefly, in this test the arterial pressure in freely moving male dTghRenhAgT mice is determined by telemetry monitoring. For this purpose, the catheter of a radio transmitter (model TA11PA-10, DSI) is implanted into the left carotid artery of dTghRenhAgT mice under anesthesia. Animals are kept on a 12 h light/dark cycle and have free access to food and water. After one week of recovery period, arterial pressure and heart rate are monitored over 24 h to establish the baseline values. Then animals receive orally by gavage either the daily dose of the test compound in vehicle (water containing 0.6% of methylcellulose and 0.5% of Tween® 80) or, as a control, vehicle only. Hemodynamic parameters are recorded continuously for an additional 24 h and maximal mean arterial pressure lowering effect and duration of antihypertensive activity are determined (mean arterial pressure=diastolic pressure+⅓·(systolic pressure−diastolic pressure)). Compounds are screened at various doses such as 3 mg/kg body weight and 10 mg/kg body weight per day.

What is claimed is:

1. A compound of formula I or a stereoisomeric form thereof, or a physiologically acceptable salt thereof,

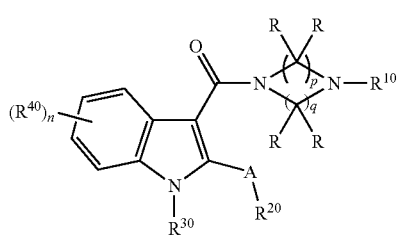

wherein

A is chosen from O, S, N(($C_1$-$C_4$)-alkyl) and C($R^a$)$_2$;

$R^a$ is chosen from hydrogen, fluorine and ($C_1$-$C_4$)-alkyl, wherein the two groups $R^a$ are independent of each other and can be identical or different, or the two groups $R^a$ together are a divalent ($C_2$-$C_8$)-alkyl group;

R is chosen from hydrogen, fluorine, ($C_1$-$C_4$)-alkyl, hydroxy-($C_1$-$C_4$)-alkyl-, ($C_1$-$C_4$)-alkyl-O—($C_1$-$C_4$)-alkyl-, phenyl-($C_1$-$C_4$)-alkyl-, heteroaryl-($C_1$-$C_4$)-alkyl-, ($C_1$-$C_4$)-alkyl-O—CO—$C_u$$H_{2u}$—, $R^1$—NH—CO—$C_u$$H_{2u}$— and ($C_1$-$C_4$)-alkyl-O—, wherein all groups R are independent of each other and can be identical or different;

$R^1$ is chosen from hydrogen, ($C_1$-$C_4$)-alkyl, hydroxy-($C_1$-$C_4$)-alkyl- and $H_2N$—CO—($C_1$-$C_4$)-alkyl-, $R^{10}$ is chosen from hydrogen, ($C_1$-$C_6$)-alkyl-O—CO— and ($C_3$-$C_7$)-cycloalkyl-$C_v$$H_{2v}$—O—CO—;

$R^{20}$ is chosen from phenyl and heteroaryl which are optionally substituted by one or more identical or different substituents chosen from halogen, ($C_1$-$C_4$)-alkyl, ($C_1$-$C_4$)-alkyl-O—, ($C_1$-$C_4$)-alkyl-S(O)$_m$—, hydroxy and cyano;

$R^{30}$ is chosen from ($C_3$-$C_7$)-cycloalkyl, ($C_5$-$C_7$)-cycloalkenyl, tetrahydropyranyl, phenyl and heteroaryl, wherein cycloalkyl and cycloalkenyl are optionally substituted by one or more identical or different substituents chosen from fluorine, ($C_1$-$C_4$)-alkyl and hydroxy, and phenyl and heteroaryl are optionally substituted by one or more identical or different substituents chosen from halogen, ($C_1$-$C_6$)-alkyl, ($C_3$-$C_7$)-cycloalkyl-$C_v$$H_{2v}$—, hydroxy-($C_1$-$C_6$)-alkyl-, ($C_1$-$C_4$)-alkyl-O—($C_1$-$C_6$)-alkyl-, ($C_3$-$C_7$)-cycloalkyl-$C_v$$H_{2v}$—O—($C_1$-$C_6$)-alkyl-, ($C_1$-$C_4$)-alkyl-CO—NH—($C_1$-$C_6$)-alkyl-, hydroxy, ($C_1$-$C_6$)-alkyl-O—, ($C_3$-$C_7$)-cycloalkyl-$C_v$$H_{2v}$—O—, hydroxy-($C_1$-$C_6$)-alkyl-O—, ($C_1$-$C_4$)-alkyl-O—($C_1$-$C_6$)-alkyl-O—, ($C_3$-$C_7$)-cycloalkyl-$C_v$$H_{2v}$—O—($C_1$-$C_6$)-alkyl-O—, ($C_1$-$C_4$)-alkyl-CO—NH—($C_1$-$C_6$)-alkyl-O—, ($C_1$-$C_6$)-alkyl-S(O)$_m$— and cyano;

$R^{40}$ is chosen from halogen, ($C_1$-$C_4$)-alkyl, ($C_3$-$C_7$)-cycloalkyl-$C_v$$H_{2v}$—, phenyl-($C_1$-$C_4$)-alkyl-, heteroaryl-($C_1$-$C_4$)-alkyl-, hydroxy-($C_1$-$C_4$)-alkyl-, ($C_1$-$C_4$)-alkyl-O—($C_1$-$C_4$)-alkyl-, ($C_3$-$C_7$)-cycloalkyl-$C_v$$H_{2v}$—O—($C_1$-$C_4$)-alkyl-, phenyl-O—($C_1$-$C_4$)-alkyl-, heteroaryl-O—($C_1$-$C_4$)-alkyl-, di(($C_1$-$C_4$)-alkyl)N—($C_1$-$C_4$)-alkyl-, HO—CO—($C_1$-$C_4$)-alkyl-, ($C_1$-$C_4$)-alkyl-O—CO—($C_1$-$C_4$)-alkyl-, $H_2N$—CO—($C_1$-$C_4$)-alkyl-, hydroxy, ($C_1$-$C_4$)-alkyl-O—, ($C_3$-$C_7$)-cycloalkyl-$C_v$$H_{2v}$—O—, phenyl-($C_1$-$C_4$)-alkyl-O—, heteroaryl-($C_1$-$C_4$)-alkyl-O—, hydroxy-($C_1$-$C_4$)-alkyl-O—, ($C_1$-$C_4$)-alkyl-O—($C_1$-$C_4$)-alkyl-O—, ($C_3$-$C_7$)-cycloalkyl-$C_v$$H_{2v}$—O—($C_1$-$C_4$)-alkyl-O—, phenyl-O—($C_1$-$C_4$)-alkyl-O—, heteroaryl-O—($C_1$-$C_4$)-alkyl-O—, di(($C_1$-$C_4$)-alkyl)N—($C_1$-$C_4$)-alkyl-O—, HO—CO—($C_1$-$C_4$)-alkyl-O—, ($C_1$-$C_4$)-alkyl-O—CO—($C_1$-$C_4$)-alkyl-O—, $H_2N$—CO—($C_1$-$C_4$)-alkyl-O—, ($C_1$-$C_4$)-alkyl-CO—O—, ($C_3$-$C_7$)-cycloalkyl-$C_v$$H_{2v}$—CO—O—, ($C_1$-$C_4$)-alkyl-NH—CO—O—, ($C_3$-$C_7$)-cycloalkyl-$C_v$$H_{2v}$—NH—CO—O—, ($C_1$-$C_4$)-alkyl-S(O)$_m$—, nitro, amino, ($C_1$-$C_4$)-alkylamino, di(($C_1$-$C_4$)-alkyl)amino, ($C_1$-$C_4$)-alkyl-CO—NH—, ($C_3$-$C_7$)-cycloalkyl-$C_v$$H_{2v}$—CO—NH—, ($C_1$-$C_4$)-alkyl-S(O)$_2$—NH—, HO—CO—, ($C_1$-$C_4$)-alkyl-O—CO—, $H_2N$—CO—, (($C_1$-$C_4$)-alkyl)-NH—CO—, di(($C_1$-$C_4$)-alkyl)N—CO—, cyano, HO—S(O)$_2$—, $H_2N$—S(O)$_2$—, (($C_1$-$C_4$)-alkyl)-NH—S(O)$_2$— and di(($C_1$-$C_4$)-alkyl)N—S(O)$_2$—, wherein all substituents $R^{40}$ are independent of each other and can be identical or different;

heteroaryl is an aromatic monocyclic, 5-membered or 6-membered, heterocyclic group which comprises 1, 2 or 3 identical or different ring heteroatoms chosen from N, O and S, wherein one of the ring nitrogen atoms can carry a hydrogen atom or a ($C_1$-$C_4$)-alkyl group, and wherein the heteroaryl group is bonded via a ring carbon atom;

m is 0, 1 or 2, wherein all numbers m are independent of each other and can be identical or different;

n is 0, 1, 2, 3 or 4;

p and q, which are independent of each other and can be identical or different, are 2 or 3;

u is 0, 1 or 2, wherein all numbers u are independent of each other and can be identical or different;

v is 0, 1 or 2, wherein all numbers v are independent of each other and can be identical or different;

wherein all alkyl groups, independently of each other, are optionally substituted by one or more fluorine atoms;

wherein all cycloalkyl groups, independently of each other, are optionally substituted by one or more identical or different substituents chosen from fluorine and ($C_1$-$C_4$)-alkyl, unless specified otherwise; and wherein all phenyl and heteroaryl groups present in R and $R^{40}$, independently of each other, are optionally substituted by one or more identical or different substituents chosen from halogen, ($C_1$-$C_4$)-alkyl, ($C_1$-$C_4$)-alkyl-O—, ($C_1$-$C_4$)-alkyl-S(O)$_2$— and cyano.

2. A compound as claimed in claim 1, wherein p is 2 and q is 2 or 3.

3. A compound as claimed in claim 1, wherein $R^{40}$ is chosen from halogen, ($C_1$-$C_4$)-alkyl, phenyl-($C_1$-$C_4$)-alkyl-, hydroxy-($C_1$-$C_4$)-alkyl-, ($C_1$-$C_4$)-alkyl-O—($C_1$-$C_4$)-alkyl-, hydroxy, ($C_1$-$C_4$)-alkyl-O—, hydroxy-($C_1$-$C_4$)-alkyl-O—, ($C_1$-$C_4$)-alkyl-O—($C_1$-$C_4$)-alkyl-O—, phenyl-O—($C_1$-$C_4$)-alkyl-O—, di(($C_1$-$C_4$)-alkyl)N—($C_1$-$C_4$)-alkyl-O—, HO—CO—($C_1$-$C_4$)-alkyl-O—, ($C_1$-$C_4$)-alkyl-O—CO—($C_1$-$C_4$)-alkyl-O—, ($C_1$-$C_4$)-alkyl-CO—O—, ($C_1$-$C_4$)-alkyl-NH—CO—O—, ($C_1$-$C_4$)-alkyl-S(O)$_m$—, HO—CO—, ($C_1$-

$C_4$)-alkyl-O—CO—, $H_2N$—CO— and cyano, wherein all substituents $R^{40}$ are independent of each other and can be identical or different.

4. A compound as claimed in claim 1, wherein
A is chosen from O, S and $C(R^a)_2$;
$R^a$ is chosen from hydrogen, fluorine and methyl, wherein the two groups $R^a$ are independent of each other and can be identical or different, or the two groups $R^a$ together are a divalent ($C_2$-$C_5$)-alkyl group;
R is chosen from hydrogen, ($C_1$-$C_4$)-alkyl, hydroxy-($C_1$-$C_4$)-alkyl-, ($C_1$-$C_4$)-alkyl-O—($C_1$-$C_4$)-alkyl-, phenyl-($C_1$-$C_4$)-alkyl-, ($C_1$-$C_4$)-alkyl-O—CO—$C_uH_{2u}$— and $R^1$—NH—CO—$C_uH_{2u}$—, wherein all groups R are independent of each other and can be identical or different;
$R^1$ is chosen from ($C_1$-$C_4$)-alkyl, hydroxy-($C_1$-$C_4$)-alkyl- and $H_2N$—CO—($C_1$-$C_4$)-alkyl-;
$R^{10}$ is chosen from hydrogen, ($C_1$-$C_6$)-alkyl-O—CO— and ($C_3$-$C_7$)-cycloalkyl-$C_vH_{2v}$—O—CO—;
$R^{20}$ is chosen from phenyl and heteroaryl which are optionally substituted by one or more identical or different substituents chosen from halogen, ($C_1$-$C_4$)-alkyl, ($C_1$-$C_4$)-alkyl-O—, ($C_1$-$C_4$)-alkyl-S(O)$_m$—, hydroxy and cyano;
$R^{30}$ is chosen from ($C_3$-$C_7$)-cycloalkyl, ($C_5$-$C_7$)-cycloalkenyl, tetrahydropyranyl, phenyl and heteroaryl, wherein cycloalkyl and cycloalkenyl are optionally substituted by one or more identical or different substituents chosen from fluorine, ($C_1$-$C_4$)-alkyl and hydroxy, and phenyl and heteroaryl are optionally substituted by one or more identical or different substituents chosen from halogen, ($C_1$-$C_6$)-alkyl, ($C_1$-$C_4$)-alkyl-O—($C_1$-$C_6$)-alkyl-, hydroxy, ($C_1$-$C_6$)-alkyl-O—, ($C_1$-$C_4$)-alkyl-O—($C_1$-$C_6$)-alkyl-O—, ($C_1$-$C_6$)-alkyl-S(O)$_m$— and cyano;
$R^{40}$ is chosen from halogen, ($C_1$-$C_4$)-alkyl, hydroxy-($C_1$-$C_4$)-alkyl-, ($C_1$-$C_4$)-alkyl-O—($C_1$-$C_4$)-alkyl-, hydroxy, ($C_1$-$C_4$)-alkyl-O—, hydroxy-($C_1$-$C_4$)-alkyl-O—, ($C_1$-$C_4$)-alkyl-O—($C_1$-$C_4$) -alkyl-O—, phenyl-O—($C_1$-$C_4$)-alkyl-O—, di(($C_1$-$C_4$)-alkyl)N—($C_1$-$C_4$)-alkyl-O—, ($C_1$-$C_4$)-alkyl -CO—O—, ($C_1$-$C_4$)-alkyl-NH—CO—O—, HO—CO—, ($C_1$-$C_4$)-alkyl-O—CO— and $H_2N$—CO—, wherein all substituents $R^{40}$ are independent of each other and can be identical or different;
heteroaryl is chosen from thiophenyl and pyridinyl;
m is 0, 1 or 2, wherein all numbers m are independent of each other and can be identical or different;
n is 0, 1 or 2;
p and q are 2;
u is 0, 1 or 2, wherein all numbers u are independent of each other and can be identical or different;
v is 0, 1 or 2;
wherein all alkyl groups, independently of each other, are optionally substituted by one or more fluorine atoms;
wherein the cycloalkyl group is optionally substituted by one or more identical or different substituents chosen from flourine and ($C_1$-$C_4$)-alkyl, unless specified otherwise; and
wherein all phenyl groups present in R and $R^{40}$, independently of each other, are optionally substituted by one or more identical of different substituents chosen from halogen, ($C_1$-$C_4$)-alkyl, ($C_1$-$C_4$)-alkyl-O—, ($C_1$-$C_4$)-alkyl-S(O)$_2$— and cyano.

5. A compound as claimed in claim 4, wherein one, two or three of the groups R, which are independent of each other and can be identical or different, are chosen from hydrogen, ($C_1$-$C_4$)-alkyl, hydroxy-($C_1$-$C_4$)-alkyl-, ($C_1$-$C_4$)-alkyl-O—($C_1$-$C_4$) -alkyl-, phenyl-($C_1$-$C_4$)-alkyl-, ($C_1$-$C_4$)-alkyl-O—CO—$C_uH_{2u}$— and $R^1$—NH—CO—$C_uH_{2u}$—, and all other groups R are hydrogen.

6. A compound as claimed in claim 5, wherein $R^{20}$ is phenyl which is optionally substituted by one or more identical or different substituents chosen from halogen, ($C_1$-$C_4$)-alkyl, ($C_1$-$C_4$)-alkyl-O—, ($C_1$-$C_4$)-alkyl-S(O)$_m$—, hydroxy and cyano.

7. A process for the preparation of a compound as claimed in claim 1, comprising reacting a compound of formula XIV with a compound of formula X to give a compound of formula XIII,

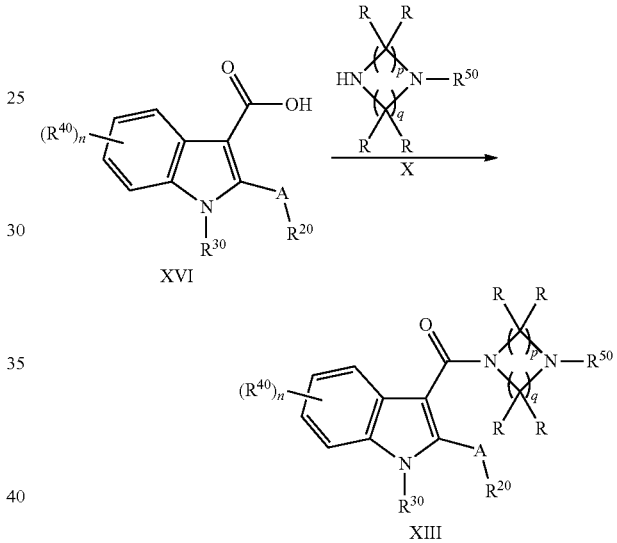

wherein A, R, $R^{20}$, $R^{30}$, $R^{40}$, n, p and q are defined as in claim 1 and, additionally, functional groups can be present in protected form or in the form of a precursor group, and $R^{50}$ is defined as $R^{10}$ in claim 1, with the exception of hydrogen, or is a protective group, and removing the protective group $R^{50}$ in the case of the preparation of a compound in which $R^{10}$ is hydrogen.

8. A pharmaceutical composition which comprises at least one compound as claimed in claim 1 and a pharmaceutically acceptable carrier.

9. A method for the treatment of hypertension comprising administering to a patient in need thereof an effective dose of a compound as claimed in claim 1.

* * * * *